United States Patent
Albrecht et al.

(10) Patent No.: US 11,040,027 B2
(45) Date of Patent: Jun. 22, 2021

(54) PROTEIN KINASE INHIBITORS FOR PROMOTING LIVER REGENERATION OR REDUCING OR PREVENTING HEPATOCYTE DEATH

(71) Applicant: HEPAREGENIX GMBH, Ulm (DE)

(72) Inventors: Wolfgang Albrecht, Ulm (DE); Stefan Laufer, Tübingen (DE); Roland Selig, Ulm (DE); Phillip Klövekorn, Pliezhausen (DE); Bent Präfke, Tübingen (DE)

(73) Assignee: Heparegenix GMBH, Ulm (DE)

( * ) Notice: Subject to any disclaimer, the term of this patent is extended or adjusted under 35 U.S.C. 154(b) by 0 days.

(21) Appl. No.: 16/478,006

(22) PCT Filed: Jan. 17, 2018

(86) PCT No.: PCT/EP2018/051110
§ 371 (c)(1),
(2) Date: Jul. 15, 2019

(87) PCT Pub. No.: WO2018/134254
PCT Pub. Date: Jul. 26, 2018

(65) Prior Publication Data
US 2019/0365723 A1    Dec. 5, 2019

(30) Foreign Application Priority Data

Jan. 17, 2017  (EP) .................................. 17151787
Nov. 30, 2017  (EP) .................................. 17204638

(51) Int. Cl.
*A61K 31/437*    (2006.01)
*A61K 31/501*    (2006.01)

(52) U.S. Cl.
CPC .......... *A61K 31/437* (2013.01); *A61K 31/501* (2013.01)

(58) Field of Classification Search
CPC ............................ A61K 31/437; A61K 31/501
See application file for complete search history.

(56) References Cited

U.S. PATENT DOCUMENTS

| | | | |
|---|---|---|---|
| 7,812,143 B2 | 10/2010 | Pratilas et al. | |
| 7,863,288 B2 * | 1/2011 | Ibrahim | A61P 31/04 514/300 |
| 8,551,479 B2 | 10/2013 | Hoey et al. | |
| 8,680,066 B2 | 3/2014 | Weisbart | |
| 9,125,899 B1 | 9/2015 | Ness et al. | |
| 9,133,460 B2 | 9/2015 | Weisbart | |
| 9,408,885 B2 | 8/2016 | Marine | |
| 9,440,969 B2 | 9/2016 | Ibrahim et al. | |
| 9,464,326 B2 | 10/2016 | Davila | |
| 9,480,744 B2 | 11/2016 | Hoey et al. | |
| 9,481,910 B2 | 11/2016 | Rosen et al. | |
| 9,624,213 B2 | 4/2017 | Ibrahim et al. | |
| 9,642,835 B2 | 5/2017 | Wandinger-Ness et al. |
| 9,717,715 B2 | 8/2017 | Lee et al. |
| 9,763,923 B2 | 9/2017 | Keum et al. |
| 9,839,687 B2 | 12/2017 | Zhao |
| 9,861,833 B1 | 1/2018 | Anderson |
| 9,873,700 B2 | 1/2018 | Zhang et al. |
| 9,945,863 B2 | 4/2018 | Sheikh et al. |
| 9,994,915 B2 | 6/2018 | Perera |
| 10,016,422 B2 | 7/2018 | Alani |
| 10,220,026 B2 | 3/2019 | Kinoh et al. |
| 2007/0105165 A1 | 5/2007 | Goolsby et al. |
| 2010/0261204 A1 | 10/2010 | Goolsby et al. |
| 2012/0095078 A1 | 4/2012 | Ronai |
| 2012/0108457 A1 | 5/2012 | Perera et al. |
| 2012/0276122 A1 | 11/2012 | Ronai |
| 2012/0321637 A1 | 12/2012 | Dong et al. |
| 2013/0210034 A1 | 8/2013 | Jacobberger et al. |
| 2013/0251702 A1 | 9/2013 | Chung et al. |
| 2013/0336889 A1 | 12/2013 | Shieh et al. |
| 2014/0031384 A1 | 1/2014 | Narita et al. |
| 2014/0045883 A1 | 2/2014 | Mahajan et al. |
| 2014/0134231 A1 | 5/2014 | Perera |
| 2014/0147411 A1 | 5/2014 | Pollack et al. |
| 2014/0243211 A1 | 8/2014 | Niculescu |
| 2014/0335077 A1 | 11/2014 | Girnita et al. |
| 2015/0056195 A1 | 2/2015 | Bertolotto-Ballotti |
| 2015/0086509 A1 | 3/2015 | Litvin et al. |
| 2015/0231069 A1 | 8/2015 | Modi |
| 2015/0269307 A1 | 9/2015 | Pal et al. |
| 2015/0335619 A1 | 11/2015 | Wandinger-Ness et al. |
| 2015/0342943 A1 | 12/2015 | Bornstein et al. |
| 2016/0215346 A1 | 7/2016 | Niculescu |
| 2016/0250292 A1 | 9/2016 | Hu et al. |
| 2017/0056327 A1 | 3/2017 | Mi et al. |
| 2017/0115275 A1 | 4/2017 | Rege et al. |
| 2017/0143845 A1 | 5/2017 | Zhao |
| 2017/0173168 A1 | 6/2017 | Zhao |
| 2017/0173176 A1 | 6/2017 | Zhao |
| 2017/0182002 A1 | 6/2017 | Wandinger-Ness et al. |
| 2017/0182012 A1 | 6/2017 | Okazawa |
| 2017/0226518 A1 | 8/2017 | Trieu |
| 2018/0015075 A1 | 1/2018 | Boscolo et al. |
| 2018/0051347 A1 | 2/2018 | Ribas et al. |
| 2018/0235951 A1 | 8/2018 | Kutlu et al. |

FOREIGN PATENT DOCUMENTS

| | | | |
|---|---|---|---|
| EP | 1977765 A1 | 10/2008 |
| EP | 1893612 B1 | 8/2011 |
| EP | 2570127 A1 | 3/2013 |
| EP | 2036990 B1 | 4/2014 |
| EP | 2815749 A1 | 12/2014 |

(Continued)

OTHER PUBLICATIONS

International Search Report, dated Apr. 11, 2018, issued in PCT/EP2018/051110.

(Continued)

*Primary Examiner* — Timothy R Rozof
(74) *Attorney, Agent, or Firm* — Viksnins Harris Padys Malen LLP

(57) ABSTRACT

The invention relates to MKK4 (mitogen-activated protein kinase 4) and their use in promoting liver regeneration or reducing or preventing hepatocyte death. The MKK4 inhibitors selectively inhibit protein kinase MKK4 over protein kinases JNK and MKK7.

15 Claims, 1 Drawing Sheet

(56) References Cited

FOREIGN PATENT DOCUMENTS

| | | |
|---|---|---|
| EP | 2519517 B1 | 3/2015 |
| EP | 2605764 B1 | 3/2015 |
| EP | 2595958 B1 | 4/2015 |
| EP | 2414356 B1 | 9/2015 |
| EP | 2622348 B1 | 9/2015 |
| EP | 2700403 B1 | 11/2015 |
| EP | 2957642 A2 | 12/2015 |
| EP | 2395004 B1 | 1/2016 |
| EP | 2714094 B1 | 2/2016 |
| EP | 3045917 A2 | 7/2016 |
| EP | 2680886 B1 | 8/2016 |
| EP | 2598657 B1 | 10/2016 |
| EP | 3088898 A1 | 11/2016 |
| EP | 3103450 A1 | 12/2016 |
| EP | 3106168 A2 | 12/2016 |
| EP | 3106173 A1 | 12/2016 |
| EP | 2790699 B1 | 4/2017 |
| EP | 2741784 B1 | 5/2017 |
| EP | 2782994 B1 | 5/2017 |
| EP | 2820041 B1 | 6/2017 |
| EP | 2879676 B1 | 6/2017 |
| EP | 2879677 B1 | 6/2017 |
| EP | 3181122 A1 | 6/2017 |
| EP | 3181127 A1 | 6/2017 |
| EP | 3181128 A1 | 6/2017 |
| EP | 2370568 B1 | 7/2017 |
| EP | 3072528 B1 | 7/2017 |
| EP | 3072529 B1 | 7/2017 |
| EP | 3195865 A1 | 7/2017 |
| EP | 3199641 A1 | 8/2017 |
| EP | 3207931 A2 | 8/2017 |
| EP | 2462116 B1 | 9/2017 |
| EP | 2694485 B1 | 11/2017 |
| EP | 2919784 B1 | 12/2017 |
| EP | 3037458 B1 | 12/2017 |
| EP | 2580322 B1 | 1/2018 |
| EP | 2955180 B1 | 1/2018 |
| EP | 3010917 B1 | 1/2018 |
| EP | 3269365 A1 | 1/2018 |
| EP | 3281675 A1 | 2/2018 |
| EP | 2937345 B1 | 3/2018 |
| EP | 2817004 B1 | 4/2018 |
| EP | 2831589 B1 | 4/2018 |
| EP | 2550266 B1 | 5/2018 |
| EP | 2958564 B1 | 5/2018 |
| EP | 2971129 B1 | 5/2018 |
| EP | 3326616 A1 | 5/2018 |
| EP | 3333259 A1 | 6/2018 |
| EP | 3333575 A1 | 6/2018 |
| EP | 2861591 B1 | 7/2018 |
| EP | 3084008 B1 | 7/2018 |
| EP | 3345624 A1 | 7/2018 |
| EP | 3346272 A1 | 7/2018 |
| EP | 2888260 B1 | 8/2018 |
| EP | 2935253 B1 | 8/2018 |
| EP | 2976333 B1 | 8/2018 |
| EP | 2983720 B1 | 8/2018 |
| EP | 3010918 B1 | 8/2018 |
| EP | 3011974 B1 | 8/2018 |
| EP | 3178943 B1 | 10/2018 |
| EP | 3088400 A1 | 11/2018 |
| EP | 3485876 A1 | 5/2019 |
| EP | 3299019 B1 | 10/2019 |
| EP | 3181136 B1 | 11/2019 |
| JP | 2016193848 A | 11/2016 |
| RU | 2572569 C1 | 1/2016 |
| WO | 2004016610 A1 | 2/2004 |
| WO | 2007002325 A1 | 1/2007 |
| WO | 2007002433 A1 | 1/2007 |
| WO | 2008082730 A2 | 7/2008 |
| WO | 2008120004 A1 | 10/2008 |
| WO | 2008120098 A2 | 10/2008 |
| WO | 2008148522 A2 | 12/2008 |
| WO | 2010006225 A1 | 1/2010 |
| WO | 2010056662 A1 | 5/2010 |
| WO | 2010068738 A1 | 6/2010 |
| WO | 2010104945 A1 | 9/2010 |
| WO | 2010111527 A1 | 9/2010 |
| WO | 2010114928 A2 | 10/2010 |
| WO | 2010129567 A1 | 11/2010 |
| WO | 2010129570 A1 | 11/2010 |
| WO | 2011015522 A2 | 2/2011 |
| WO | 2011017583 A1 | 2/2011 |
| WO | 2011022335 A1 | 2/2011 |
| WO | 2011057974 A1 | 5/2011 |
| WO | 2011060216 A1 | 5/2011 |
| WO | 2011079133 | 6/2011 |
| WO | 2011090738 A2 | 7/2011 |
| WO | 2011097594 A2 | 8/2011 |
| WO | 2011112678 A1 | 9/2011 |
| WO | 2011119894 A2 | 9/2011 |
| WO | 2011156588 A1 | 12/2011 |
| WO | 2012010538 A2 | 1/2012 |
| WO | 2012017430 A2 | 2/2012 |
| WO | 2012021778 A2 | 2/2012 |
| WO | 2012022677 A2 | 2/2012 |
| WO | 2012022724 A1 | 2/2012 |
| WO | 2012027536 A1 | 3/2012 |
| WO | 2012027716 A1 | 3/2012 |
| WO | 2012030738 A2 | 3/2012 |
| WO | 2012037000 A1 | 3/2012 |
| WO | 2012037060 A1 | 3/2012 |
| WO | 2012042009 A1 | 4/2012 |
| WO | 2012068468 A1 | 5/2012 |
| WO | 2012068562 A2 | 5/2012 |
| WO | 2012071453 A1 | 5/2012 |
| WO | 2012075324 A1 | 6/2012 |
| WO | 2012075327 A1 | 6/2012 |
| WO | 2012080151 A1 | 6/2012 |
| WO | 2012095505 A1 | 7/2012 |
| WO | 2012109075 A1 | 8/2012 |
| WO | 2012109329 A1 | 8/2012 |
| WO | 2012117396 A1 | 9/2012 |
| WO | 2012118632 A1 | 9/2012 |
| WO | 2012119095 A1 | 9/2012 |
| WO | 2012122444 A1 | 9/2012 |
| WO | 2012135750 A1 | 10/2012 |
| WO | 2012136859 A1 | 10/2012 |
| WO | 2012138783 A2 | 10/2012 |
| WO | 2012138809 A1 | 10/2012 |
| WO | 2012145503 A1 | 10/2012 |
| WO | 2012146933 A1 | 11/2012 |
| WO | 2012146936 A1 | 11/2012 |
| WO | 2012149186 A9 | 11/2012 |
| WO | 2012149547 A1 | 11/2012 |
| WO | 2012154858 A1 | 11/2012 |
| WO | 2012154879 A2 | 11/2012 |
| WO | 2012154908 A2 | 11/2012 |
| WO | 2012161776 A1 | 11/2012 |
| WO | 2012166949 A1 | 12/2012 |
| WO | 2012167173 A1 | 12/2012 |
| WO | 2012170384 A1 | 12/2012 |
| WO | 2012170715 A1 | 12/2012 |
| WO | 2012178038 A1 | 12/2012 |
| WO | 2013012477 A1 | 1/2013 |
| WO | 2013037943 A1 | 3/2013 |
| WO | 2013043232 A2 | 3/2013 |
| WO | 2013043715 A1 | 3/2013 |
| WO | 2013044169 A1 | 3/2013 |
| WO | 2013052608 A1 | 4/2013 |
| WO | 2013063001 A1 | 5/2013 |
| WO | 2013074594 A1 | 5/2013 |
| WO | 2013074874 A1 | 5/2013 |
| WO | 2013078059 A1 | 5/2013 |
| WO | 2013082499 A1 | 6/2013 |
| WO | 2013086260 A2 | 6/2013 |
| WO | 2013087546 A1 | 6/2013 |
| WO | 2013105894 A1 | 7/2013 |
| WO | 2013105895 A1 | 7/2013 |
| WO | 2013109142 A1 | 7/2013 |
| WO | 2013114367 A9 | 8/2013 |
| WO | 2013116228 A1 | 8/2013 |
| WO | 2013123463 A1 | 8/2013 |

(56) References Cited

FOREIGN PATENT DOCUMENTS

| | | |
|---|---|---|
| WO | 2013126617 A1 | 8/2013 |
| WO | 2013131019 A1 | 9/2013 |
| WO | 2013134467 A1 | 9/2013 |
| WO | 2013134647 A1 | 9/2013 |
| WO | 2013138210 A1 | 9/2013 |
| WO | 2013138371 A1 | 9/2013 |
| WO | 2013138753 A1 | 9/2013 |
| WO | 2013139724 A1 | 9/2013 |
| WO | 2013142427 A1 | 9/2013 |
| WO | 2013148100 A1 | 10/2013 |
| WO | 2013148337 A1 | 10/2013 |
| WO | 2013148537 A1 | 10/2013 |
| WO | 2013152034 A1 | 10/2013 |
| WO | 2013152038 A1 | 10/2013 |
| WO | 2013152041 A1 | 10/2013 |
| WO | 2013155077 A1 | 10/2013 |
| WO | 2013165320 A1 | 11/2013 |
| WO | 2013169858 A1 | 11/2013 |
| WO | 2013170071 A1 | 11/2013 |
| WO | 2013170159 A1 | 11/2013 |
| WO | 2013171753 A1 | 11/2013 |
| WO | 2013173500 A2 | 11/2013 |
| WO | 2013173644 A2 | 11/2013 |
| WO | 2013177092 A1 | 11/2013 |
| WO | 2013180949 A1 | 12/2013 |
| WO | 2013181415 A1 | 12/2013 |
| WO | 2013188500 A1 | 12/2013 |
| WO | 2014005089 A2 | 1/2014 |
| WO | 2014006093 A1 | 1/2014 |
| WO | 2014008270 A1 | 1/2014 |
| WO | 2014009318 A1 | 1/2014 |
| WO | 2014009319 A1 | 1/2014 |
| WO | 2014012902 A2 | 1/2014 |
| WO | 2014018862 A1 | 1/2014 |
| WO | 2014018932 A2 | 1/2014 |
| WO | 2014022116 A2 | 2/2014 |
| WO | 2014022117 A1 | 2/2014 |
| WO | 2014022128 A1 | 2/2014 |
| WO | 2014022826 A2 | 2/2014 |
| WO | 2014027056 A1 | 2/2014 |
| WO | 2014028461 A2 | 2/2014 |
| WO | 2014031856 A1 | 2/2014 |
| WO | 2014035846 A2 | 3/2014 |
| WO | 2014036562 A2 | 3/2014 |
| WO | 2014039742 A1 | 3/2014 |
| WO | 2014047342 A1 | 3/2014 |
| WO | 2014047973 A1 | 4/2014 |
| WO | 2014052613 A2 | 4/2014 |
| WO | 2014053650 A1 | 4/2014 |
| WO | 2014055775 A1 | 4/2014 |
| WO | 2014056894 A1 | 4/2014 |
| WO | 2014058317 A1 | 4/2014 |
| WO | 2014059484 A1 | 4/2014 |
| WO | 2014072357 A1 | 5/2014 |
| WO | 2014072493 A1 | 5/2014 |
| WO | 2014078211 A1 | 5/2014 |
| WO | 2014078383 A1 | 5/2014 |
| WO | 2014079709 A1 | 5/2014 |
| WO | 2014080251 A1 | 5/2014 |
| WO | 2014080290 A2 | 5/2014 |
| WO | 2014080291 A2 | 5/2014 |
| WO | 2014089280 A1 | 6/2014 |
| WO | 2014089324 A1 | 6/2014 |
| WO | 2014094182 A1 | 6/2014 |
| WO | 2014096965 A2 | 6/2014 |
| WO | 2012144463 A1 | 7/2014 |
| WO | 2014105966 A2 | 7/2014 |
| WO | 2014107718 A2 | 7/2014 |
| WO | 2014113260 A1 | 7/2014 |
| WO | 2014113792 A1 | 7/2014 |
| WO | 2014113794 A2 | 7/2014 |
| WO | 2014128235 A1 | 8/2014 |
| WO | 2014130375 A1 | 8/2014 |
| WO | 2014138279 A1 | 9/2014 |
| WO | 2014138338 A1 | 9/2014 |
| WO | 2014139326 A1 | 9/2014 |
| WO | 2014140286 A1 | 9/2014 |
| WO | 2014144121 A9 | 9/2014 |
| WO | 2014144850 A1 | 9/2014 |
| WO | 2014145254 A2 | 9/2014 |
| WO | 2014145753 A1 | 9/2014 |
| WO | 2014151304 A1 | 9/2014 |
| WO | 2014159353 A1 | 10/2014 |
| WO | 2014159500 A1 | 10/2014 |
| WO | 2014160130 A1 | 10/2014 |
| WO | 2014160358 A1 | 10/2014 |
| WO | 2014160729 A1 | 10/2014 |
| WO | 2014165412 A1 | 10/2014 |
| WO | 2014165644 A2 | 10/2014 |
| WO | 2014167126 A2 | 10/2014 |
| WO | 2014168721 A2 | 10/2014 |
| WO | 2014168975 A1 | 10/2014 |
| WO | 2014172046 A9 | 10/2014 |
| WO | 2014177038 A1 | 11/2014 |
| WO | 2014177915 A1 | 11/2014 |
| WO | 2014182643 A2 | 11/2014 |
| WO | 2014184211 A1 | 11/2014 |
| WO | 2014193647 A2 | 12/2014 |
| WO | 2014194127 A1 | 12/2014 |
| WO | 2014204856 A1 | 12/2014 |
| WO | 2015002754 A2 | 1/2015 |
| WO | 2015004533 A2 | 1/2015 |
| WO | 2015004534 A2 | 1/2015 |
| WO | 2015004636 A1 | 1/2015 |
| WO | 2015017034 A1 | 2/2015 |
| WO | 2015017546 A1 | 2/2015 |
| WO | 2015017729 A1 | 2/2015 |
| WO | 2015034519 A1 | 3/2015 |
| WO | 2015034729 A1 | 3/2015 |
| WO | 2015036499 A1 | 3/2015 |
| WO | 2015036643 A2 | 3/2015 |
| WO | 2015037005 A1 | 3/2015 |
| WO | 2015038649 A1 | 3/2015 |
| WO | 2015039107 A1 | 3/2015 |
| WO | 2015040609 A1 | 3/2015 |
| WO | 2015041533 A1 | 3/2015 |
| WO | 2015041534 A1 | 3/2015 |
| WO | 2015043492 A1 | 4/2015 |
| WO | 2015049280 A1 | 4/2015 |
| WO | 2015049377 A1 | 4/2015 |
| WO | 2015058056 A1 | 4/2015 |
| WO | 2015061256 A1 | 4/2015 |
| WO | 2015061288 A1 | 4/2015 |
| WO | 2015027915 A1 | 5/2015 |
| WO | 2015066439 A2 | 5/2015 |
| WO | 2015066452 A2 | 5/2015 |
| WO | 2015069266 A1 | 5/2015 |
| WO | 2015070020 A2 | 5/2015 |
| WO | 2015070224 A1 | 5/2015 |
| WO | 2015070280 A1 | 5/2015 |
| WO | 2015073072 A1 | 5/2015 |
| WO | 2015073109 A1 | 5/2015 |
| WO | 2015073644 A1 | 5/2015 |
| WO | 2015075483 A1 | 5/2015 |
| WO | 2015075749 A1 | 5/2015 |
| WO | 2015077717 A1 | 5/2015 |
| WO | 2015078424 A1 | 6/2015 |
| WO | 2015080867 A1 | 6/2015 |
| WO | 2015084804 A1 | 6/2015 |
| WO | 2015085229 A1 | 6/2015 |
| WO | 2015089380 A2 | 6/2015 |
| WO | 2015092707 A2 | 6/2015 |
| WO | 2015095767 A1 | 6/2015 |
| WO | 2015095819 A2 | 6/2015 |
| WO | 2015097621 A2 | 7/2015 |
| WO | 2015099094 A1 | 7/2015 |
| WO | 2015100104 A1 | 7/2015 |
| WO | 2015101996 A1 | 7/2015 |
| WO | 2015104292 A2 | 7/2015 |
| WO | 2015105860 A9 | 7/2015 |
| WO | 2015106164 A1 | 7/2015 |
| WO | 2015116868 A2 | 8/2015 |
| WO | 2015120110 A2 | 8/2015 |
| WO | 2015121649 A1 | 8/2015 |

(56) References Cited

FOREIGN PATENT DOCUMENTS

| | | |
|---|---|---|
| WO | 2015127407 A1 | 8/2015 |
| WO | 2015130554 A2 | 9/2015 |
| WO | 2015130922 A2 | 9/2015 |
| WO | 2015135094 A1 | 9/2015 |
| WO | 2015143004 A9 | 9/2015 |
| WO | 2015144934 A1 | 10/2015 |
| WO | 2015148654 A1 | 10/2015 |
| WO | 2015150472 A2 | 10/2015 |
| WO | 2015151078 A2 | 10/2015 |
| WO | 2015151079 A2 | 10/2015 |
| WO | 2015151080 A2 | 10/2015 |
| WO | 2015151081 A2 | 10/2015 |
| WO | 2015153657 A2 | 10/2015 |
| WO | 2015153978 A1 | 10/2015 |
| WO | 2015154065 A1 | 10/2015 |
| WO | 2015155753 A2 | 10/2015 |
| WO | 2015157093 A1 | 10/2015 |
| WO | 2015157125 A1 | 10/2015 |
| WO | 2015161230 A1 | 10/2015 |
| WO | 2015164161 A1 | 10/2015 |
| WO | 2015-175965 A1 | 11/2015 |
| WO | 2015168599 A1 | 11/2015 |
| WO | 2015171833 A1 | 11/2015 |
| WO | 2015173267 A1 | 11/2015 |
| WO | 2015173788 A1 | 11/2015 |
| WO | 2015178770 A1 | 11/2015 |
| WO | 2015179075 A1 | 11/2015 |
| WO | 2015179855 A1 | 11/2015 |
| WO | 2015187496 A1 | 12/2015 |
| WO | 2015187499 A1 | 12/2015 |
| WO | 2015187512 A1 | 12/2015 |
| WO | 2015187883 A1 | 12/2015 |
| WO | 2015188169 A1 | 12/2015 |
| WO | 2015191568 A2 | 12/2015 |
| WO | 2015191610 A2 | 12/2015 |
| WO | 2015191986 A1 | 12/2015 |
| WO | 2015191996 A1 | 12/2015 |
| WO | 2015193702 A1 | 12/2015 |
| WO | 2015200329 A1 | 12/2015 |
| WO | 2016000827 A1 | 1/2016 |
| WO | 2016001830 A1 | 1/2016 |
| WO | 2016005593 A1 | 1/2016 |
| WO | 2016007919 A2 | 1/2016 |
| WO | 2016008433 A1 | 1/2016 |
| WO | 2016008853 A1 | 1/2016 |
| WO | 2016011160 A1 | 1/2016 |
| WO | 2016011328 A1 | 1/2016 |
| WO | 2016011362 A1 | 1/2016 |
| WO | 2016013007 A1 | 1/2016 |
| WO | 2016015597 A1 | 2/2016 |
| WO | 2016015598 A1 | 2/2016 |
| WO | 2016015604 A1 | 2/2016 |
| WO | 2016015605 A1 | 2/2016 |
| WO | 2016016665 A1 | 2/2016 |
| WO | 2016022956 A1 | 2/2016 |
| WO | 2016024595 A1 | 2/2016 |
| WO | 2016025648 A1 | 2/2016 |
| WO | 2016025650 A1 | 2/2016 |
| WO | 2016025651 A1 | 2/2016 |
| WO | 2016028672 A1 | 2/2016 |
| WO | 2016030455 A1 | 3/2016 |
| WO | 2016036954 A1 | 3/2016 |
| WO | 2016040622 A1 | 3/2016 |
| WO | 2016044772 A1 | 3/2016 |
| WO | 2016055028 A1 | 4/2016 |
| WO | 2016057554 A1 | 4/2016 |
| WO | 2016057924 A1 | 4/2016 |
| WO | 2016059602 A2 | 4/2016 |
| WO | 2016059622 A2 | 4/2016 |
| WO | 2016061231 A1 | 4/2016 |
| WO | 2016061253 A1 | 4/2016 |
| WO | 2016066594 A1 | 5/2016 |
| WO | 2016066634 A2 | 5/2016 |
| WO | 2016069928 A1 | 5/2016 |
| WO | 2016073421 A1 | 5/2016 |
| WO | 2016073871 A1 | 5/2016 |
| WO | 2016073884 A1 | 5/2016 |
| WO | 2016075333 A1 | 5/2016 |
| WO | 2016077375 A1 | 5/2016 |
| WO | 2016077378 A1 | 5/2016 |
| WO | 2016077380 A1 | 5/2016 |
| WO | 2016081281 A1 | 5/2016 |
| WO | 2016081364 A1 | 5/2016 |
| WO | 2016083956 A1 | 6/2016 |
| WO | 2016086200 A1 | 6/2016 |
| WO | 2016087936 A1 | 6/2016 |
| WO | 2016087942 A1 | 6/2016 |
| WO | 2016089208 A2 | 6/2016 |
| WO | 2016092375 A1 | 6/2016 |
| WO | 2016097036 A1 | 6/2016 |
| WO | 2016097863 A1 | 6/2016 |
| WO | 2016097870 A1 | 6/2016 |
| WO | 2016100542 A1 | 6/2016 |
| WO | 2016100619 A2 | 6/2016 |
| WO | 2016100924 A1 | 6/2016 |
| WO | 2016102179 A1 | 6/2016 |
| WO | 2016109452 A1 | 7/2016 |
| WO | 2016112305 A1 | 7/2016 |
| WO | 2016115218 A1 | 7/2016 |
| WO | 2016115376 A1 | 7/2016 |
| WO | 2016116935 A1 | 7/2016 |
| WO | 2016118014 A2 | 7/2016 |
| WO | 2016123054 A2 | 8/2016 |
| WO | 2016123086 A2 | 8/2016 |
| WO | 2016123378 A1 | 8/2016 |
| WO | 2016123387 A1 | 8/2016 |
| WO | 2016123679 A1 | 8/2016 |
| WO | 2016125169 A1 | 8/2016 |
| WO | 2016126878 A2 | 8/2016 |
| WO | 2016130546 A1 | 8/2016 |
| WO | 2016133910 A1 | 8/2016 |
| WO | 2016138114 A1 | 9/2016 |
| WO | 2016139331 A1 | 9/2016 |
| WO | 2016139534 A2 | 9/2016 |
| WO | 2016140878 A9 | 9/2016 |
| WO | 2016140879 A9 | 9/2016 |
| WO | 2016140884 A1 | 9/2016 |
| WO | 2016141169 A1 | 9/2016 |
| WO | 2016149271 A1 | 9/2016 |
| WO | 2016151065 A1 | 9/2016 |
| WO | 2016151067 A1 | 9/2016 |
| WO | 2016153394 A1 | 9/2016 |
| WO | 2016160102 A1 | 10/2016 |
| WO | 2016160833 A1 | 10/2016 |
| WO | 2016160881 A1 | 10/2016 |
| WO | 2016164578 A1 | 10/2016 |
| WO | 2016164641 A1 | 10/2016 |
| WO | 2016165676 A1 | 10/2016 |
| WO | 2016168150 A2 | 10/2016 |
| WO | 2016168264 A1 | 10/2016 |
| WO | 2016168612 A1 | 10/2016 |
| WO | 2016168634 A1 | 10/2016 |
| WO | 2016168721 A1 | 10/2016 |
| WO | 2016172010 A1 | 10/2016 |
| WO | 2016174183 A1 | 11/2016 |
| WO | 2016179394 A1 | 11/2016 |
| WO | 2016182893 A1 | 11/2016 |
| WO | 2016183486 A1 | 11/2016 |
| WO | 2016184999 A1 | 11/2016 |
| WO | 2016187122 A1 | 11/2016 |
| WO | 2016187508 A2 | 11/2016 |
| WO | 2016190897 A1 | 12/2016 |
| WO | 2016191296 A1 | 12/2016 |
| WO | 2016193955 A1 | 12/2016 |
| WO | 2016196384 A1 | 12/2016 |
| WO | 2016197129 A1 | 12/2016 |
| WO | 2016198256 A1 | 12/2016 |
| WO | 2016200688 A1 | 12/2016 |
| WO | 2016200726 A1 | 12/2016 |
| WO | 2016200778 A1 | 12/2016 |
| WO | 2016201299 A1 | 12/2016 |
| WO | 2016201328 A1 | 12/2016 |
| WO | 2016201370 A1 | 12/2016 |
| WO | 2017004122 A1 | 1/2017 |

(56) References Cited

FOREIGN PATENT DOCUMENTS

| | | |
|---|---|---|
| WO | 2017004153 A1 | 1/2017 |
| WO | 2017004393 A1 | 1/2017 |
| WO | 2017005919 A1 | 1/2017 |
| WO | 2017008046 A1 | 1/2017 |
| WO | 2017009258 A1 | 1/2017 |
| WO | 2017009520 A1 | 1/2017 |
| WO | 2017019520 A1 | 2/2017 |
| WO | 2017019664 A1 | 2/2017 |
| WO | 2017019804 A1 | 2/2017 |
| WO | 2017021857 A1 | 2/2017 |
| WO | 2017023994 A1 | 2/2017 |
| WO | 2017024032 A2 | 2/2017 |
| WO | 2017024207 A1 | 2/2017 |
| WO | 2017027403 A1 | 2/2017 |
| WO | 2017031363 A2 | 2/2017 |
| WO | 2017031368 A1 | 2/2017 |
| WO | 2017031427 A1 | 2/2017 |
| WO | 2017037579 A1 | 3/2017 |
| WO | 2017040990 A1 | 3/2017 |
| WO | 2017053243 A1 | 3/2017 |
| WO | 2017058007 A1 | 4/2017 |
| WO | 2017059268 A1 | 4/2017 |
| WO | 2017062426 A1 | 4/2017 |
| WO | 2017066193 A1 | 4/2017 |
| WO | 2017067592 A1 | 4/2017 |
| WO | 2017068013 A9 | 4/2017 |
| WO | 2017068156 A1 | 4/2017 |
| WO | 2017070618 A1 | 4/2017 |
| WO | 2017079267 A1 | 5/2017 |
| WO | 2017079746 A2 | 5/2017 |
| WO | 2017083788 A1 | 5/2017 |
| WO | 2017083789 A1 | 5/2017 |
| WO | 2017085251 A1 | 5/2017 |
| WO | 2017087851 A1 | 5/2017 |
| WO | 2017089347 A1 | 6/2017 |
| WO | 2017091865 A1 | 6/2017 |
| WO | 2017095826 A1 | 6/2017 |
| WO | 2017098336 A1 | 6/2017 |
| WO | 2017099591 A1 | 6/2017 |
| WO | 2017100201 A1 | 6/2017 |
| WO | 2017106129 A1 | 6/2017 |
| WO | 2017106189 A1 | 6/2017 |
| WO | 2017117052 A1 | 7/2017 |
| WO | 2017117182 A1 | 7/2017 |
| WO | 2017120600 A1 | 7/2017 |
| WO | 2017121877 A1 | 7/2017 |
| WO | 2017127282 A1 | 7/2017 |
| WO | 2017129753 A1 | 8/2017 |
| WO | 2017132518 A1 | 8/2017 |
| WO | 2017133517 A1 | 8/2017 |
| WO | 2017136741 A1 | 8/2017 |
| WO | 2017136774 A1 | 8/2017 |
| WO | 2017136794 A1 | 8/2017 |
| WO | 2017138925 A1 | 8/2017 |
| WO | 2017145164 A9 | 8/2017 |
| WO | 2017145179 A1 | 8/2017 |
| WO | 2017151517 A1 | 9/2017 |
| WO | 2017151775 A9 | 9/2017 |
| WO | 2017154001 A1 | 9/2017 |
| WO | 2017161045 A1 | 9/2017 |
| WO | 2017161188 A1 | 9/2017 |
| WO | 2017162510 A1 | 9/2017 |
| WO | 2017164486 A1 | 9/2017 |
| WO | 2017176265 A1 | 10/2017 |
| WO | 2017176565 A1 | 10/2017 |
| WO | 2017180581 A1 | 10/2017 |
| WO | 2017180789 A2 | 10/2017 |
| WO | 2017180820 A1 | 10/2017 |
| WO | 2017181073 A1 | 10/2017 |
| WO | 2017181149 A1 | 10/2017 |
| WO | 2017184534 A1 | 10/2017 |
| WO | 2017188357 A1 | 11/2017 |
| WO | 2017189613 A1 | 11/2017 |
| WO | 2017189856 A1 | 11/2017 |
| WO | 2017193086 A1 | 11/2017 |
| WO | 2017194431 A1 | 11/2017 |
| WO | 2017196989 A1 | 11/2017 |
| WO | 2017200826 A1 | 11/2017 |
| WO | 2017201532 A1 | 11/2017 |
| WO | 2017204210 A1 | 11/2017 |
| WO | 2017205536 A2 | 11/2017 |
| WO | 2017205538 A1 | 11/2017 |
| WO | 2017205686 A1 | 11/2017 |
| WO | 2017205756 A1 | 11/2017 |
| WO | 2017210580 A1 | 12/2017 |
| WO | 2017212420 A1 | 12/2017 |
| WO | 2017216584 A1 | 12/2017 |
| WO | 2017218191 A1 | 12/2017 |
| WO | 2017218365 A1 | 12/2017 |
| WO | 2017222958 A1 | 12/2017 |
| WO | 2017223245 A1 | 12/2017 |
| WO | 2017223565 A1 | 12/2017 |
| WO | 2018002415 A1 | 1/2018 |
| WO | 2018005445 A9 | 1/2018 |
| WO | 2018005973 A1 | 1/2018 |
| WO | 2018007592 A1 | 1/2018 |
| WO | 2018009528 A1 | 1/2018 |
| WO | 2018009904 A2 | 1/2018 |
| WO | 2018011351 A2 | 1/2018 |
| WO | 2018023197 A1 | 2/2018 |
| WO | 2018031707 A1 | 2/2018 |
| WO | 2018034356 A1 | 2/2018 |
| WO | 2018035308 A2 | 2/2018 |
| WO | 2018045058 A1 | 3/2018 |
| WO | 2018045238 A1 | 3/2018 |
| WO | 2018045239 A1 | 3/2018 |
| WO | 2018049008 A1 | 3/2018 |
| WO | 2018049014 A1 | 3/2018 |
| WO | 2018049250 A1 | 3/2018 |
| WO | 2018051306 A1 | 3/2018 |
| WO | 2018057973 A1 | 3/2018 |
| WO | 2018064611 A1 | 4/2018 |
| WO | 2018069885 A1 | 4/2018 |
| WO | 2018071549 A1 | 4/2018 |
| WO | 2018075447 A1 | 4/2018 |
| WO | 2018075801 A1 | 4/2018 |
| WO | 2018085674 A1 | 5/2018 |
| WO | 2018086139 A1 | 5/2018 |
| WO | 2018089687 A1 | 5/2018 |
| WO | 2018091634 A1 | 5/2018 |
| WO | 2018092064 A1 | 5/2018 |
| WO | 2018093724 A1 | 5/2018 |
| WO | 2018094190 A2 | 5/2018 |
| WO | 2018095353 A1 | 5/2018 |
| WO | 2018098280 A1 | 5/2018 |
| WO | 2018102670 A2 | 6/2018 |
| WO | 2018102769 A1 | 6/2018 |
| WO | 2018107146 A1 | 6/2018 |
| WO | 2018111902 A1 | 6/2018 |
| WO | 2018114953 A1 | 6/2018 |
| WO | 2018115150 A1 | 6/2018 |
| WO | 2018115888 A1 | 6/2018 |
| WO | 2018118611 A1 | 6/2018 |
| WO | 2018119448 A1 | 6/2018 |
| WO | 2018127082 A1 | 7/2018 |
| WO | 2018127748 A1 | 7/2018 |
| WO | 2018132660 A1 | 7/2018 |
| WO | 2018134254 A1 | 7/2018 |
| WO | 2017153220 A1 | 9/2019 |

OTHER PUBLICATIONS

Written Opinion, dated Apr. 11, 2018, issued in PCT/EP2018/051110.

Deibler, et. al., "A Chemical Probe Strategy for Interrogating Inhibitor Selectivity Across the MEK Kinase Family"; ACS Chem. Biol. 2017; 12; pp. 1245-1256.

Deibler, et. al., "A Chemical Probe Strategy for Interrogating Inhibitor Selectivity Across the MEK Kinase Family"; ACS Chem. Biol. 2017; 12; Supporting Information.

Erion, et. al., "Liver-Targeted Drug Delivery Using HepDirect Prodrugs"; JPET 2005; 312; pp. 554-560.

(56) References Cited

OTHER PUBLICATIONS

Grueninger, et. al., "Novel screening cascade identifies MKK4 as key kinase regulating Tau phosphorylation of Ser422"; Mol. Cell. Biochem. 2011; 357; pp. 199-207.
Hu, et. al., "MicroRNA-145 attenuates TNF-α-driven cartilage matrix degradation in osteoarthritis via direct suppression of MKK4"; Cell Death and Disease; 2017; 8; e3140.
Ogura, et. al., "Prenylated quinolinecarboxylic acid derivative prevents neuronal cell death through inhibition of MKK4"; Biochem. Pharmacol. 2018; doi: 10.1016/j.bcp.2018.10.008.
Vin, et. al., "BRAF inhibitors suppress apoptosis through off-target inhibition of JNK signaling"; eLife; 2013; 2:e00969.
Vin, et. al., "BRAF inhibitors suppress apoptosis through off-target inhibition of JNK signaling"; eLife; 2013; 2:e00969, Supplemental information.
Willenbring, et al., "A Therapy for Liver Failure Found in the JNK Yard"; Cell. 2013; 153; pp. 283-284.
Wuestefeld, et al., "A Direct In Vivo RNAi Screen Identifies MKK4 as a Key Regulator of Liver Regeneration"; Cell. 2013; 153; pp. 389-401.

\* cited by examiner

PROTEIN KINASE INHIBITORS FOR PROMOTING LIVER REGENERATION OR REDUCING OR PREVENTING HEPATOCYTE DEATH

CROSS-REFERENCE TO RELATED APPLICATIONS

This application is the U.S. national phase, pursuant to 35 U.S.C. § 371, of PCT international application Ser. No. PCT/EP2018/051110, filed Jan. 17, 2018, designating the United States and published in English on Jul. 26, 2018 as publication WO 2018/134254 A1, which claims priority under 35 U.S.C. § 119(a) to European patent application No. 17151787.3, filed Jan. 17, 2017 and European patent application No. 17204638.5, filed Nov. 30, 2017. The entire disclosures of the aforementioned patent applications are hereby incorporated herein by reference.

The present invention relates to protein kinase inhibitors which inhibit mitogen-activated protein kinase 4 (MKK4) and in particular, selectively inhibit MKK4 over protein kinases JNK1 and MKK7.

BACKGROUND OF THE INVENTION

Liver diseases may be caused by infection, injury, exposure to toxic compounds, like alcohol or drugs, autoimmune processes, genetic defects, and other factors. Liver has a remarkable regenerative capacity which, however, may be impaired in disease state and may therefore be insufficient to compensate for the loss of hepatocytes and organ function.

WO 2007/002433 describes compounds which are protein kinase inhibitors useful to treat diseases and conditions associated with aberrant activity of protein kinases. These compounds are inhibitors of Raf protein kinase, in particular B-Raf and c-Raf and mutations thereof and are therefore useful for cancer treatment. Further, they are said to inhibit a large variety of other protein kinases, among them c-Jun N-terminal kinases (JNK) and in particular JNK1. WO 2010/002325 has a similar disclosure and WO 2012/109075 and WO 2014/194127 disclose modified compounds having Raf protein kinase inhibiting activity. H. Vin et al. refer to two compounds of WO 2007/002433 as B-Raf inhibitors that suppress apoptosis through off-target inhibition of JNK signaling. WO 2012/136859 discloses some compounds which are described as inhibitors of mitogen-activated protein kinase 4 (MKK4) and as being useful in the treatment of liver failure, for the protection of hepatocytes against apoptosis and for the regeneration of hepatocytes. Wuestefeld et al. (Cell 153:389-401, 2013) describe a functional genetic approach for the identification of gene targets that can be exploited to increase the regenerative capacity of hepatocytes. In particular, Wuestefeld et al. identify protein kinase MKK4 as a key regulator of liver regeneration and report that MKK4 suppression increased hepatocyte regeneration via compensatory upregulation of MKK7 and a JNK1-dependent activation of ATF2 and ELK1. On the basis of the findings of the prior art it has been concluded that MKK4 and JNK1 inhibitors could be useful to treat JNK1-mediated diseases. However, it has been recognized in clinical treatments that treatment of liver diseases with such compounds failed.

SUMMARY OF THE INVENTION

The problem underlying the invention was to provide useful MKK4 inhibitors, in particular MKK4 inhibitors which selectively inhibit MKK4 over MKK7 and JNK1. A further problem was to provide MKK4 inhibitors, in particular MKK4 inhibitors which selectively inhibit MKK4 over MKK7 and JNK1, which are useful for treating liver diseases and especially for promoting liver regeneration or reducing or preventing hepatocyte death.

This problem was solved by providing the MKK4 inhibitors of formula (I) and the compounds of formula (Ia).

Thus, the invention relates to a MKK4 inhibitor having formula (I)

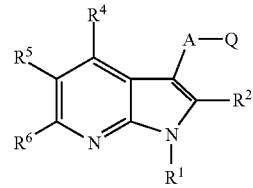

and the pharmaceutically acceptable salts, prodrugs, biologically active metabolites, solvates and stereoisomers thereof,
wherein the variables in formula (I) have the meanings as follows:
$R^1$ is H or alkyl;
$R^2$ is H, alkyl, —$CF_3$, —$CH_2$—X—$(CH_2)_n$—Y or $CH_2X^1$;
X is —$N(R^{10})$—, —S—, or —O—;
Y is H,
  phenyl, which is optionally substituted with one or two groups, which are independently selected from alkyl, halogen, alkoxy, hydroxy, and $SO_2$alkyl,
  alkoxy,
  furyl,
  thienyl, or
  pyridyl and
  wherein the group —$(CH_2)_n$— is optionally substituted by OH;
n is 1, 2 or 3;
$X^1$ is $NR^{10}SO_2$-phenyl, wherein the phenyl group is optionally substituted with one or two groups, which are independently selected from halogen, —$OCF_3$ and alkoxy, or a heterocyclic group selected from piperidinyl, piperazinyl, morpholinyl and thiomorpholinyl which group may be substituted with alkyl, hydroxyalkyl, alkoxyalkyl, hydroxy or carboxyl;
A is a bond or a linking group which is selected from
  —CO—,
  —CO—CO—,
  —S—,
  —SO—,
  —$SO_2$—,
  —O—,
  —C(=N—$NHR^{10}$)—,
  —CH=, —$CONR^{10}$—,
  —$NR^{10}CO$—,
  —$NR^{10}$—$SO_2$—,
  —$O_2S$—$NR^{10}$—,
  —CO-alkylene-,
  -alkylene-CO—,
  -alkylene-$NR^{10}CO$—,
  —$OCNR^{10}$-alkylene-,
  alkylene which is optionally substituted with 1 or 2 groups independently selected from OH and alkoxy,
  alkenylene, alkinylene,
—NR$^{10}$,
-alkylene-NR$^{10}$-alkylene-,
-alkylene-NR$^{10}$—,
—NR$^{10}$-alkylene-,
alkylene-NR$^{10}$SO$_2$—,
—SO$_2$NR$^{10}$-alkylene-,
-alkylene-NR$^{10}$SO$_2$-alkylene-,

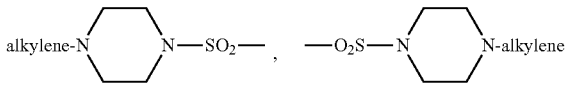

-alkylene-CONR$^{10}$-alkylene-,
-alkylene-NR$^{10}$CO-alkylene-,
-alkylene-NR$^{10}$CONR$^{10}$-alkylene-,
-alkylene-NR$^{10}$CSNR$^{10}$-alkylene-,
-alkylene-NR$^{10}$CONR$^{10}$—
—NR$^{10}$CONR$^{10}$-alkylene-,
-alkylene-NR$^{10}$CSNR$^{10}$—,
—NR$^{10}$CSNR$^{10}$-alkylene-,
-alkylene-NR$^{10}$-alkylene-NR$^0$—,
—NR$^{10}$-alkylene-NR$^{10}$-alkylene-,
—CO-alkylene-O—,
—O-alkylene-CO—;

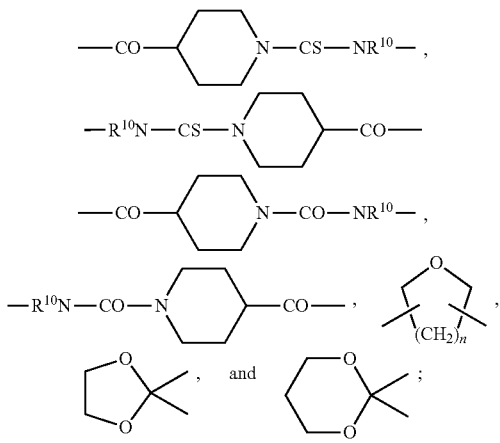

Q is an aromatic or heteroaromatic 5- or 6-membered monocyclic or aromatic or heteroaromatic 9- or 10-membered bicyclic group wherein the heteroaromatic groups have 1, 2 or 3 heteroatoms independently selected from O, N and S which group is optionally substituted with 1, 2 or 3 groups independently selected from
alkyl which is optionally substituted with 1 or 2 substituents independently selected from phenyl, halogen substituted phenyl, halogen, OH, CN, —NR$^{10}$R$^{10}$, cycloalkyl and a heteroaromatic 5- or 6-membered monocyclic group having 1, 2 or 3 heteroatoms independently selected from O, N and S;
alkenyl which is optionally substituted with —NO$_2$;
halogen;
hydroxy;
—CHO;
—COOR$^{22}$;
—NO$_2$;
alkoxy,
haloalkoxy;
cycloalkyloxy;
alkylcarbonyloxy;
alkylthio;
thienylthio
phenyl, which is optionally substituted with 1 or 2 groups independently selected from alkyl, hydroxyalkyl, alkoxy, halogen, alkylthio and NR$^{10}$R$^{10}$; phenoxy, which is optionally substituted with halogen;
—CO-alkyl which is optionally substituted with phenoxy;
—CO-phenyl which is optionally substituted with halogen or alkoxy;
a heteroaromatic or non-aromatic heterocyclic 5- or 6-membered monocyclic group having 1, 2 or 3 heteroatoms independently selected from O, N and S which is optionally substituted with 1 or 2 groups independently selected from alkyl, haloalkyl, halogen, thioalkyl and phenyl;
—NR$^{10}$R$^{11}$
—NR$^{10}$SO$_2$R$^{12}$;
—NR$^{10}$SO$_2$R$^{13}$;
—NR$^{10}$SO$_2$NHR$^{10}$;
—N=S(=O)R$^{10}$NR$^{10}$R$^{10}$;
—O-alkylene-phenyl wherein the phenyl group is optionally substituted with a group selected from alkyl, haloalkyl, halogen, —SO$_2$alkyl, imidazolyl, oxadiazolyl, and CH$_2$-piperazinyl;
—O-alkylene-R$^{14}$;
—OCH$_2$O—, (attached in neighboring positions to Q);
—OCF$_2$O— (attached in neighboring positions to Q);
—OCH$_2$CH$_2$O— (attached in neighboring positions to Q);
—O-alkylene-R$^{15}$;
—O-alkylene-phenyl, wherein the phenyl is optionally substituted with 1, 2 or 3 substituents which are independently selected from alkyl, halogen, haloalkyl, and —CH$_2$-piperazinyl which is optionally substituted with alkyl at the second nitrogen; indolyl which is optionally substituted at the nitrogen atom with alkyl, alkenyl, alkinyl, —CH$_2$—O-alkylene-phenyl, —SO$_2$-phenyl, —CONR$^{10}$R$^{16}$, or —SO$_2$NR$^{10}$R$^{10}$;
—NR$^{10}$CONR$^{10}$R$^{17}$;
—NR$^{10}$COR$^{18}$;
—NR$^{10}$COOR$^{10}$;
—CO—NR$^{10}$R$^{19}$;
-alkylene-NR$^{10}$SO$_2$R$^{20}$;
—SO$_2$R$^{21}$; and
-alkylene-NR$^{10}$COR$^{23}$;
R$^4$ is
H,
halogen,
CN,
NO$_2$,
alkyl,
phenyl which is optionally substituted with 1, 2 or 3 groups independently selected from NR$^{26}$R$^{26}$, —COR$^{24}$, alkyl, alkoxy, haloalkyl, hydroxyalkyl, alkylsulfonyl, CN, NO$_2$, alkenyl, and carboxyl-substituted alkenyl,
-alkylene-NR$^{10}$SO$_2$—R$^{27}$,
a heteroaromatic or non-aromatic heterocyclic 5- or 6-membered monocyclic or heteroaromatic 9- or 10-membered bicyclic group having 1, 2 or 3 heteroatoms independently selected from O, N and S which group is optionally substituted with 1 or 2 groups independently selected from
alkyl,
alkoxy, halogen,
cycloalkyl,
—CHO,
phenylcarbonyl,
phenylcarbonyl, wherein the phenyl group is substituted with halogen or hydroxy, haloalkylcarbonyl,
NR$^{10}$R$^{10}$
a heteroaromatic or non-aromatic heterocyclic 5- or 6-membered monocyclic group having 1, 2 or 3 heteroatoms independently selected from O, N and S which in turn may be substituted by alkyl,
-alkylenoxyphenyl,
alkylenethiophenyl,
phenylalkyl wherein the phenyl group is optionally substituted with alkyl or alkoxy,
-alkylene-COOR$^{10}$, or
alkenyl which is optionally substituted by phenyl or halogen-substituted phenyl;
R$^5$ is
H,
halogen,
alkyl, which is optionally substituted with 1 or 2 groups independently selected from alkoxy, NR$^{10}$R$^{10}$, —COOR$^{10}$, and oxadiazolyl,
alkoxy,
alkenyl,
alkinyl,
phenyl or naphthyl which phenyl or naphthyl is optionally substituted with 1, 2 or 3 groups independently selected from alkyl, halogen, haloalkyl, hydroxy, hydroxyalkyl, alkylthio, alkylsulfonyl, alkylsulfonyl-NR$^{10}$—, NRoR$^{10}$, R$^{10}$R$^{10}$NSO$_2$—, alkoxy, benzyloxy, haloalkoxy, —OCH$_2$O— (methylenedioxy attached in neighboring positions to the phenyl ring), —OCH$_2$CH$_2$O— (ethylenedioxy attached in neighboring positions to the phenyl ring), NO$_2$, —COOR$^{10}$, —CONR$^{10}$R$^{10}$, CN, alkylcarbonyl-NR$^{10}$—, alkenyl, and carboxyl-substituted alkenyl,
phenylalkenyl wherein the phenyl group is optionally substituted with 1, 2 or 3 groups independently selected from OH, alkoxy and —CONR$^{10}$R$^{19}$;
NR$^{10}$R$^{28}$
a heteroaromatic or non-aromatic heterocyclic 5- or 6-membered monocyclic or heteroaromatic 9- or 10-membered bicyclic group group having 1, 2 or 3 heteroatoms independently selected from O, N and S which is optionally substituted with 1 or 2 groups independently selected from alkyl, alkoxy, morpholinyl, piperazinyl, oxadiazolyl and phenylcarbonyl wherein the phenyl group is optionally substituted with alkyl, halogen or alkoxy;
R$^6$ is H, alkoxy, NR$^{10}$R$^{10}$, or —NR$^{10}$-phenyl wherein the phenyl group is optionally substituted with NR$^{10}$R$^{10}$, alkoxy, morpholinyl, halogen or —SO$_2$morpholinyl;
R$^{10}$ at each occurrence independently is H, alkyl, phenyl which is optionally substituted with hydroxyl or alkoxy or is phenylalkyl wherein the phenyl group is optionally substituted with halogen;
R$^{11}$ is H,
alkyl, which is optionally substituted with 1 or 2 groups independently selected from phenyl, pyridyl and cycloalkyl,
phenylalkyl wherein the phenyl group is optionally substituted with halogen, alkoxy or haloalkyl,
phenyl which is optionally substituted with benzyloxy, furyl, cycloalkylalkyl, thienyl, —CO$_2$alkyl, —CO$_2$alkylphenyl, or —COalkyl;

R$^{12}$ is alkyl, heteroalkyl having 1, 2 or 3 heteroatoms independently selected from O, N and S, or phenyl which heteroalkyl is optionally substituted with 1 or 2 groups independently selected from alkyl, alkoxy, alkoxycarbonyl, haloalkoxy, halogen, haloalkyl, CN, NO$_2$, alkylcarbonylamino, oxazolyl, —OCH$_2$O— (methylenedioxy attached in neighboring positions to the phenyl ring), and —OCH$_2$CH$_2$O— (ethylenedioxy attached in neighboring positions to the phenyl ring),
R$^{13}$ is a heteroaromatic or non-aromatic heterocyclic 5- or 6-membered group having 1, 2 or 3 heteroatoms independently selected from O, N and S which group is optionally substituted with 1 or 2 groups independently selected from alkyl, pyridyl, alkoxycarbonyl, oxazolyl and oxazolyl which is substituted with alkyl or alkoxycarbonyl;
R$^{14}$ is a heteroaromatic or non-aromatic heterocyclic 5- or 6-membered monocyclic or heteroaromatic 9- or 10-membered bicyclic group having 1, 2 or 3 heteroatoms independently selected from O, N and r S which group is optionally substituted with 1 or 2 groups independently selected from alkyl, haloalkyl, —NR$^{10}$R$^{10}$, morpholinyl, and 2-pyrrolidone;
R$^{15}$ is hydroxyl, alkoxy, haloalkoxy, alkoxyalkoxy, phenylalkoxy, pyranyloxy, NR$^{10}$R$^{10}$ morpholinyl, cycloalkyl, —CONR$^{10}$R$^{10}$, —COOR$^{10}$, —CH$_2$F, —CHF$_2$, —CF$_3$, or —CN,
R$^{16}$ is alkyl which is optionally substituted with phenyl or pyridyl,
R$^{17}$ is H,
alkyl,
haloalkyl,
alkoxyalkyl,
cycloalkyl,
a heteroaromatic 5- or 6-membered group having 1, 2 or 3 heteroatoms independently selected from O, N and S which group is optionally substituted with alkyl or alkoxy,
morpholinoalkyl,
cycloalkylalkyl,
N-benzylpyrrolidinyl,
phenyl which is optionally substituted with alkyl, alkoxy, haloalkyl, —NR$^{10}$R$^{10}$ or halogen, or
phenylalkyl wherein the phenyl group is optionally substituted with alkyl, haloalkyl or halogen, or
R$^{17}$ and R$^{10}$ together form a cycloalkyl ring which is optionally substituted with acetylamino,
R$^{18}$ is alkyl, haloalkyl, phenyl,

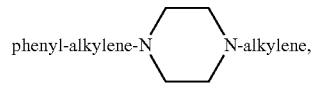

morpholinyl or pyrrolidinyl which is optionally substituted with —NR$^{10}$R$^{10}$;
R$^{19}$ is H, alkyl, phenylalkyl, phenyl, phenyl which is substituted with alkoxy, or is alkylene-SO$_2$-alkyl or

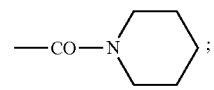

$R^{20}$ is phenyl which is optionally substituted with alkyl, phenyl or phenyl which is substituted with alkyl or hydroxyalkyl;

$R^{21}$ is $NR^{10}R^{10}$, alkyl or phenyl which is optionally substituted with halogen;

$R^{22}$ is H, alkyl or phenyl;

$R^{23}$ is phenyl or phenyl substituted with alkyl which is optionally substituted with piperazinyl or alkyl substituted piperazinyl;

$R^{24}$ is alkyl, thienyl, alkyl substituted thienyl or $NR^{25}R^{25}$;

$R^{25}$ at each occurrence independently is H or alkyl or both groups $R^{25}$ together with the nitrogen atom to which they are attached form an alkylene or oxaalkylene group;

$R^{26}$ at each occurrence independently is

H, alkyl, phenylalkyl, alkylcarbonyl, alkylsulfonyl or a heteroaromatic 5- or 6-membered monocyclic group group having 1, 2 or 3 heteroatoms independently selected from O, N and S which group is optionally substituted with alkyl or halogen, phenyl which is optionally substituted with $NR^{10}R^{10}$, halogen, alkoxy, a non-aromatic heterocyclic 5- or 6-membered monocyclic group having 1, 2 or 3 heteroatoms selected from O, N and S, alkylsulfonyl and heteroalkylsulfonyl;

$R^{27}$ is phenyl or naphthyl which phenyl or naphthyl is optionally substituted with 1 or 2 groups independently selected from halogen, alkoxy, haloalkoxy, alkyl, and haloalkyl, phenylalkyl, thienyl which is optionally substituted with 1 or 2 groups independently selected from halogen, alkyl, haloalkyl, and an aromatic heterocyclic 5- or 6-membered monocyclic group having 1, 2 or 3 heteroatoms independently selected from O, N and S, or $NR^{10}R^{10}$, $R^{28}$ is phenyl, quinolinyl, alkylsulfonyl, or phenyl, which is substituted with halogen, alkyl, $NR^{10}R^{10}$, morpholinyl or morpholinosulfonyl.

DETAILED DESCRIPTION OF THE INVENTION

Figure 1:
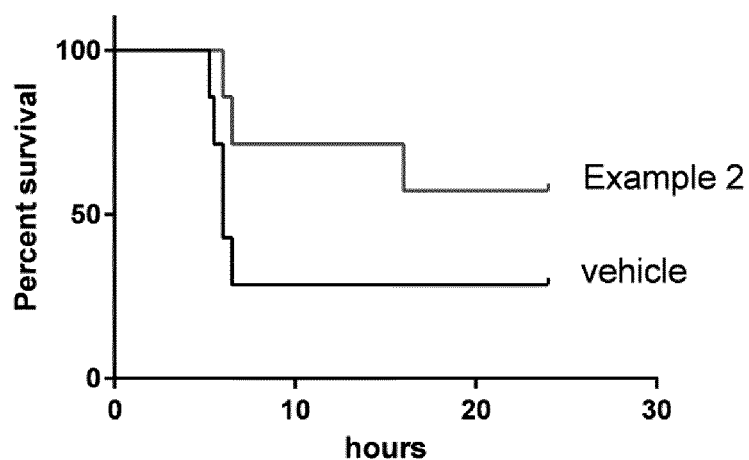
FIG. 1 is a Kaplan-Meier plot of the survival rate of a compound of the invention as compared to vehicle.

In an embodiment, $R^5$ is
H,
halogen,
alkyl, which is optionally substituted with 1 or 2 groups independently selected from alkoxy, $NR^{10}R^{10}$, —$COOR^{10}$, and oxadiazolyl,
alkoxy,
alkenyl,
alkinyl,
phenyl which is optionally substituted with 1, 2 or 3 groups independently selected from alkyl, halogen, haloalkyl, hydroxyalkyl, alkylsulfonyl, alkylsulfonyl-$NR^{10}$—, $NR^{10}R^{10}$, alkoxy, benzyloxy, haloalkoxy, $NO_2$, —$COOR^{10}$, —CO $NR^{10}R^{10}$, CN, alkylcarbonyl-$NR^{10}$—, alkenyl, and carboxyl-substituted alkenyl,
$NR^{10}R^{28}$
a heteroaromatic or non-aromatic heterocyclic 5- or 6-membered monocyclic or heteroaromatic 9- or 10-membered bicyclic group having 1, 2 or 3 heteroatoms independently selected from O, N and S which group is optionally substituted with 1 or 2 groups independently selected from alkyl, alkoxy, morpholinyl, piperazinyl, oxadiazolyl and phenylcarbonyl which is optionally substituted with alkyl, halogen and alkoxy.

In a further embodiment, $R^5$ is
halogen,
phenyl which is optionally substituted with 1, 2 or 3 groups independently selected from alkyl, halogen, haloalkyl, alkylsulfonyl, alkylsulfonyl-$NR^{10}$—, $NO_2$, —$COOR^{10}$, and
—$CONR^{10}R^{10}$, or
a heteroaromatic 5- or 6-membered monocyclic group having 1, 2 or 3 heteroatoms independently selected from O, N and S which group is optionally substituted with 1 or 2 groups independently selected from alkyl, alkoxy, morpholinyl, piperazinyl, oxadiazolyl and phenylcarbonyl wherein the phenyl group is optionally substituted with alkyl, halogen or alkoxy.

In a still further embodiment, $R^5$ is halogen, a heteroaromatic 5- or 6-membered monocyclic group having 1, 2 or 3 heteroatoms independently selected from O, N and S, or phenyl which is optionally substituted with 1 or 2 groups independently selected from halogen, alkyl, $NR^{10}R^{10}$, —$OCH_2O$—, —$OCH_2CH_2O$—, and alkoxy.

In a still further embodiment, $R^5$ is phenyl substituted with 1, 2 or 3 groups independently selected from alkyl, halogen, haloalkyl, hydroxy, hydroxyalkyl, alkylthio, $NH_2$, alkoxy, haloalkoxy, —$OCH_2O$— (methylenedioxy attached in neighboring positions to the phenyl ring), —$OCH_2CH_2O$— (ethylenedioxy attached in neighboring positions to the phenyl ring) and CN, or is naphthyl, thienyl, furyl, or quinolinyl which is optionally substituted with alkyl, halogen or alkoxy.

In a still further embodiment, $R^1$, $R^2$, $R^4$, and $R^6$, independently of each other, are H or alkyl, and in particular are H.

In a still further embodiment, $R^{10}$ at each occurrence independently is H, alkyl or phenylalkyl wherein the phenyl group is optionally substituted with halogen, and in particular $R^{10}$ at each occurrence independently is H or alkyl.

In a still further embodiment, A is —CO—, —CO—CO—, —CH(OH)—CH(OH)— or —CH=CH—.

In a still further embodiment, A is —CO—.

In a still further embodiment, Q is phenyl which is substituted as defined above.

In a still further embodiment, the invention relates to a MKK4 inhibitor and the pharmaceutically acceptable salts, solvates and optical isomers thereof, wherein the MKK4 inhibitor is of the formula I, wherein $R^1$ to $R^6$, $R^{10}$, A and Q are as defined above in any combination.

In a still further embodiment, the invention relates to a MKK4 inhibitor and the pharmaceutically acceptable salts, solvates and optical isomers thereof, wherein the MKK4 inhibitor is of the formula Ia (Ia)

wherein
$R^1$ is H or alkyl;
$R^2$ is H or alkyl;
$R^4$ is H or alkyl;
$R^6$ is H or alkyl;

$R^{10}$ is H, alkyl, or phenylalkyl;

$R^{12}$ is H, alkyl, or phenylalkyl;

$R^w$ is —NR$^{10}$SO$_2$R$^{12}$ or —N=S(=O)R$^{10}$NR$^{10}$R$^{10}$;

$R^x$ is H, halogen or alkyl;

$R^y$ is H, halogen or alkyl;

$R^5$ is phenyl substituted with 1, 2 or 3 groups independently selected from alkyl, halogen, haloalkyl, hydroxy, hydroxyalkyl, alkylthio, NH$_2$, alkoxy, haloalkoxy, —OCH$_2$O— (methylenedioxy attached in neighboring positions to the phenyl ring), —OCH$_2$CH$_2$O-(ethylenedioxy attached in neighboring positions to the phenyl ring) and CN, or $R^5$ is naphthyl, thienyl, furyl, or quinolinyl which is optionally substituted with alkyl, halogen or alkoxy.

In an embodiment of formula Ia, one of $R^x$ or $R^y$ is alkyl or halogen, and the other of $R^x$ and $R^y$ is H, halogen or alkyl, in particular alkyl or halogen. Halogen is preferably F or Cl. In particular, $R^x$ and $R^y$ are both fluorine, most preferably in o-position to the carbonyl group. In a further embodiment, $R^w$ is in 3-position relative to the carbonyl group. Preferably, $R^w$ is —NR$^{10}$SO$_2$R$^{12}$.

In a further embodiment of formula Ia, $R^{10}$ is H or alkyl.

In a further embodiment of formula Ia, $R^{12}$ is alkyl.

Further, the invention relates to the compounds of formula (Ia), in which the variables are as defined above.

In an embodiment, the following compounds are excluded from formula (Ia):

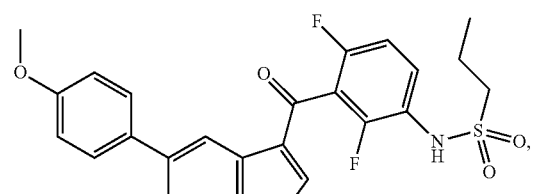

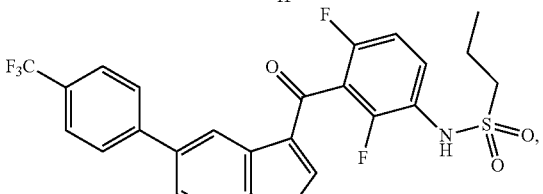

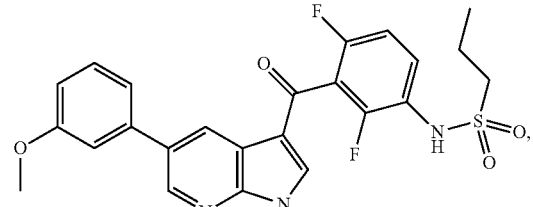

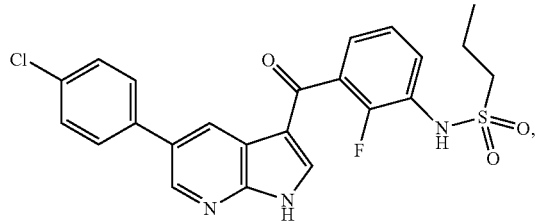

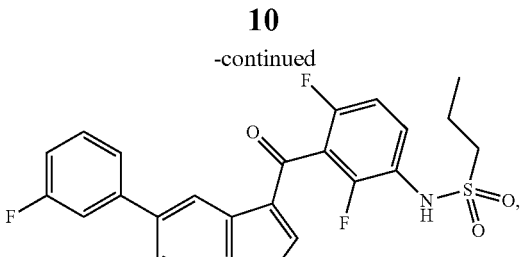

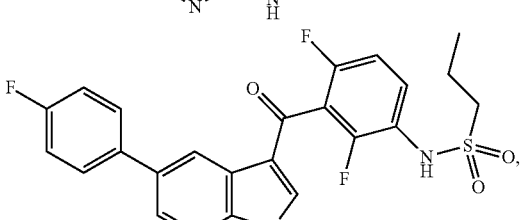

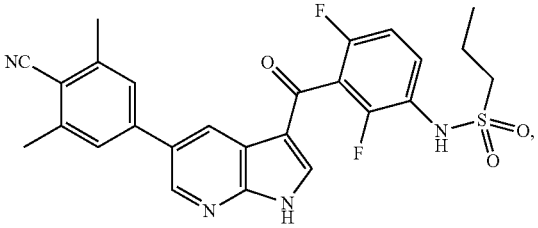

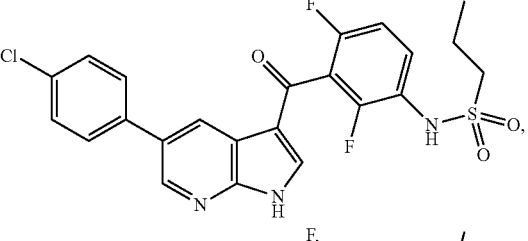

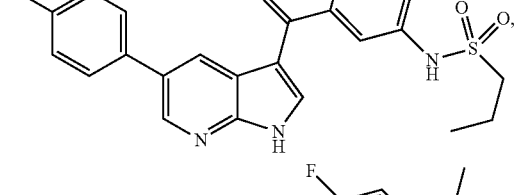

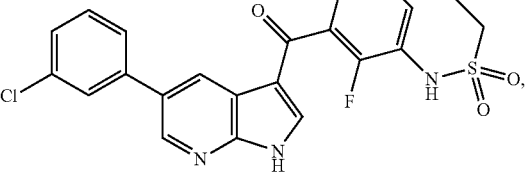

and the pharmaceutically acceptable salts, solvates and optical isomers thereof.

In an embodiment, the MKK4 inhibitors of formula (I) and (Ia) and the compounds of formula (Ia) and the pharmaceutically acceptable salts, solvates and optical isomers thereof selectively inhibit protein kinase MKK4 over protein kinases JNK1 and MKK7.

Further, the invention also relates to said compounds for use in promoting liver regeneration or reducing or preventing hepatocyte death and, at the same time, increasing hepatocyte proliferation.

In an embodiment, the invention relates to a MKK4 inhibitor and the pharmaceutically acceptable salts, solvates and optical isomers thereof which is selected from:

propane-1-sulfonic acid {3-[5-(4-chloro-phenyl)-1H-pyrrolo[2,3-b]pyridine-3-carbonyl]-2,4-difluoro-phenyl}amide;

propane-1-sulfonic acid [3-(5-chloro-1H-pyrrolo[2,3-b]pyridine-3-carbonyl]-2,4-difluoro-phenyl}amide;

propane-1-sulfonic acid [3-(5-bromo-1H-pyrrolo[2,3-b]pyridine-3-carbonyl]-2,4-difluoro-phenyl}amide;

propane-1-sulfonic acid [3-(1H-pyrrolo[2,3-b]pyridine-3-carbonyl]-2,4-difluoro-phenyl}amide; and propane-1-sulfonic acid [3-(5-chloro-1H-pyrrolo[2,3-b]pyridine-3-carbonyl)-2,4-difluoro-phenyl}-N-methylamide.

The invention also includes the pharmaceutically acceptable salts of the compounds mentioned above. The pharmaceutically acceptable salts are especially acid or base addition salts with pharmaceutically acceptable acids or bases. Examples of suitable pharmaceutically acceptable organic and inorganic acids are hydrochloric acid, hydrobromic acid, phosphoric acid, sulfuric acid, sulfamic acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966. Examples of suitable pharmaceutically acceptable organic and inorganic bases are alkali metal hydroxides, such as sodium hydroxide or potassium hydroxide, alkaline earth metal hydroxides such as calcium or magnesium hydroxide, ammonium hydroxide, organic nitrogen bases such as dimethylamine, trimethylamine, ethanolamine, diethanolamine, triethanolamine, choline, 2-amino-2-hydroxymethyl-propane-1,3-diol, meglumine, procaine etc. L-arginine, L-lysine, ethylenediamine, or hydroxyethylpyrrolidine.

The invention also includes any tautomeric, crystal and polymorphic form of the compounds and salts of the present invention and mixtures thereof.

The invention also includes solvates such as hydrates.

The compounds of the invention may contain one or more chiral centers, and exist in different optically active forms such enantiomers and diastereomers.

As used herein, the term "pro-drug" refers to an agent which is converted into the parent drug in vivo by some physiological chemical process. An example, without limitation, of a pro-drug would be a compound of the present invention in the form of an ester.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue. Exemplary pro-drugs include, but are not limited to, compounds with carboxylic acid substituents wherein the free hydrogen is replaced by ($C_1$-$C_4$)alkyl, ($C_1$-$C_{12}$)alkanoyloxy-methyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyl-oxy)ethyl having from 4 to 7 carbon atoms, 1-methyl-1-(alkoxycarbonyloxy)-ethyl having from 5 to 8 carbon atoms, N-(alkoxycarbonyl) aminomethyl having from 3 to 9 carbon atoms, 1-(N-(alkoxycarbonyl)amino)ethyl having from 4 to 10 carbon atoms, 3-phthalidyl, 4-crotono-lactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)-alkylcarbamoyl-($C_1$-$C_2$)alkyl and piperidino-, pyrrolidino- or morpholino($C_2$-$C_3$)alkyl. Other exemplary pro-drugs release an alcohol of Formula (I) wherein the free hydrogen of the hydroxyl substituent (e.g., R group contains hydroxyl) is replaced by ($C_1$-$C_6$)alkanoyloxy-methyl, 1-(($C_1$-$C_6$)alkanoyloxy)-ethyl, 1-methyl-1-(($C_1$-$C_6$)alkanoyloxy)ethyl, ($C_1$-$C_{12}$)alkoxy-carbonyloxy-methyl, N—($C_1$-$C_6$)-alkoxy-carbonylaminomethyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, P(O)(OH)$_2$, —P(O)(O($C_1$-$C_6$)alkyl)$_2$ or glycosyl (the radical resulting from detachment of the hydroxyl of the hemiacetal of a carbohydrate).

The expression MKK4 inhibitor means that, upon administration, the kinase activity of MKK4 is inhibited with an $IC_{50}$ of <10 μmol/l, preferably <1 μmol/l, and in particular <0.5 μmol/l. The expression "selectively inhibit protein kinase MKK4 over protein kinases JNK1 and MKK7" as used herein means that the ratio of MKK7 inhibiting activity to MKK4 inhibiting activity or the ratio of JNK1 inhibiting activity to MKK4 inhibiting activity, expressed as either percent of control or Kd, is ≥10, as measured with KINOMEscan™.

The expression "promoting liver regeneration or reducing or preventing hepatocyte death" as used herein means an increase in the relative number of proliferating hepatocytes by at least 30%, preferably at least 50%, as compared to the number of proliferating cells at the beginning of therapy. In particular, the expression means an increase by ≥100% when compared to the number of proliferating cells at the beginning of therapy. In this context, the experimental determination and quantification will be performed using standard methods, e.g. the quantification of the protein Ki67, which is strictly associated with cell proliferation. For quantification of proliferating hepatocytes in a tissue slide, several immunohistochemical standard methods are available, which use a primary anti-Ki67 antibody followed by visualization of anti-Ki67-binding by using, for example, a horseradish peroxidase conjugated secondary antibody. The amount of peroxidase activity, which is visualized by enzymatic conversion of chromogenic substrates, correlates with the amount of Ki67 protein and the number of proliferating cells.

In the experiments described below, hepatocyte proliferation was quantified by Ki67-staining using the primary polyclonal rabbit anti-Ki67 antibody from Abcam (article no. ab15580, Abcam, Cambridge, USA) and the fluorophore tetramethylrhodamine containing secondary goat polyclonal antibody from Invitrogen (article no. 16101, Invitrogen/ThermoFisher). Based on data obtained from several preclinical mouse models it was found that shRNA (small hairpin RNA) mediated suppression of MKK4 in a chronic CCl$_4$ (carbon tetrachloride) mediated liver damage mouse model increased hepatocyte proliferation from 13% to 27% (compared to a control shRNA) and was associated with decreased liver damage (transaminases) and decreased liver fibrosis. According to the definition in the previous chapter, the relative increase of proliferating cells was 108%. In a model of alcohol induced steatohepatitis (ASH), shRNA mediated silencing of MKK4 resulted in a hepatocyte proliferation rate of 4% as compared to 2% when a control shRNA was used (relative increase: 100%). The duplication of hepatocyte proliferation was associated with decreased steatosis (fat deposition) and decreased liver damage as measured by transaminases. Along the same lines, shRNA mediated MKK4 silencing increased hepatocyte proliferation from 16% (control shRNA) to 33% (relative increase: 106%) in a model of partial hepatectomy (48 hrs after surgical removal of two thirds of the liver). Again, increased hepatocyte proliferation was associated with improved liver regeneration and a faster restoration of liver mass.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine or chlorine.

Alkyl is a straight-chain or branched alkyl group which is preferably a $C_1$-$C_6$-alkyl group, i.e. an alkyl group having from 1 to 6 carbon atoms, and more preferably a $C_1$-$C_4$-alkyl group. Examples of an alkyl group are methyl, ethyl, n-propyl, iso-propyl, n-butyl, 2-butyl, iso-butyl, tert-butyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The definition of alkyl is likewise applicable to any group which includes an alkyl group.

Haloalkyl is a halogenated alkyl group as defined above, wherein at least one, e.g. 1, 2, 3, 4 or all of the hydrogen atoms are replaced by 1, 2, 3, 4 or a corresponding number of identical or different halogen atoms, such as trifluoromethyl, chloromethyl, bromomethyl, difluoromethyl, fluoromethyl, difluoroethyl, etc. Particular examples include the fluorinated $C_1$-$C_4$ alkyl groups as defined, such as trifluoromethyl, difluoromethyl, fluoromethyl, or difluoroethyl.

Cycloalkyl is a cycloaliphatic radical which is preferably $C_3$-$C_8$-cycloalkyl, i.e. a cycloalkyl group having from 3 to 8 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is >C=O.

Aminocarbonyl is NH$_2$C(O)—.

Alkenyl is a singly unsaturated hydrocarbon radical which is preferably a $C_2$-$C_6$-alkenyl group, i.e. an alkenyl group having 2, 3, 4, 5 or 6 carbon atoms, e.g. vinyl, allyl (2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl, 2-hexen-1-yl.

Alkinyl is a singly unsaturated hydrocarbon radical which is preferably a $C_2$-$C_6$-alkinyl group, i.e. an alkinyl group having 2, 3, 4, 5 or 6 carbon atoms, e.g. ethynyl, 2-propyn-1-yl, 1-propyn-1-yl, 2-propyn-2-yl and the like. $C_3$-$C_5$-Alkinyl is, in particular, 2-propyn-1-yl, 2-butyn-1-yl, 3-butyn-1-yl, 2-pentyn-1-yl, 3-pentyn-1-yl, 4-pentyn-1-yl.

Alkylene is straight-chain or branched alkylene group which is preferably a $C_1$-$C_8$-alkylene group, i.e. an alkylene group having from 1 to 5 carbon atoms. Examples include methylene, ethylene and 1-methylethylene. A further example is propylene. Another further example is butylene. The definition of alkylene is likewise applicable to any group which includes an alkylene group.

Heteroalkylene is a straight-chain or branched alkyl group having 1, 2 or 3 heteroatoms which are selected from oxygen, nitrogen and sulfur. Examples for heteroalkylene are alkyloxyalkyl, alkylaminoalkyl, dialkylaminoalkyl or alkylthioalkyl. Any alkyl or alkylene group is as defined above. Alkyloxyalkyl is preferred.

Alkenylene is straight-chain or branched alkenylene group which is preferably a $C_2$-$C_4$-alkenylene group, i.e. an alkenylene group having from 2 to 4 carbon atoms. Examples include vinyl and propenyl.

Alkinylene is straight-chain or branched alkinylene group which is preferably a $C_2$-$C_4$-alkinylene group, i.e. an alkinylene group having from 2 to 4 carbon atoms. Examples include propynylene.

Aryl (or aromatic group) is a 6- to 12-membered, in particular 6- to 10-membered, aromatic cyclic radical which can be a monocyclic aromatic ring, for example, phenyl etc., or a fused polycyclic aromatic ring comprising a first monocyclic aromatic ring and one or more carbocycles which are saturated, partially unsaturated or aromatic, for example, naphthyl, indenyl, tetrahydronaphthyl, indanyl.

A heteroaromatic (or heteroaryl) group is a 5- or 6-membered monocyclic or 9- or 10-membered bicyclic aromatic group having 1, 2 or 3 heteroatoms selected from O, N and S. The heteroaryl or heteroaromatic group may be bound to the neighboring group via a carbon atom (C-bound) or via a nitrogen heteroatom (N-bound). The heterocyclic radicals may be bound via a carbon atom (C-bound) or a nitrogen atom (N-bound). Preferred heteroaromatic radicals comprise 1 nitrogen atom as ring member atom and optionally 1 or 2 further heteroatoms as ring members, which are selected, independently of each other from O, S and N. Examples are:

C-bound, 5-membered, heteroaromatic rings:

2-furyl, 3-furyl, 5-furyl, 2-thienyl, 3-thienyl, 5-thienyl, pyrrol-2-yl, pyrrol-3-yl, pyrrol-5-yl, pyrazol-3-yl, pyrazol-4-yl, pyrazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, oxazol-2-yl, oxazol-4-yl, oxazol-5-yl, thiazol-2-yl, thiazol-4-yl, thiazol-5-yl, 1,2,3-oxadiazol-imidazol-4-yl,4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings:

pyridin-2-yl, pyridin-3-yl (3-pyridyl), pyridin-4-yl (4-pyridyl), pyridin-5-yl, pyridazin-3-yl, pyridazin-4-yl, pyridazin-6-yl, pyrimidin-2-yl, pyrimidin-4-yl, pyrimidin-5-yl, pyrazin-2-yl, pyrazin-5-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings:
pyrrol-1-yl, pyrazol-1-yl, imidazol-1-yl, 1,2,3-triazol-1-yl, 1,2,4-triazol-1-yl.

Bicyclic heteroaromatic groups include one of the described 5- or 6-membered heteroaromatic rings and a further anellated, saturated or unsaturated or aromatic carbocycle, such as a benzene, cyclohexane, cyclohexene or cyclohexadiene ring. Examples are quinolinyl, isoquinolinyl, indolyl, indolizinyl, isoindolyl, 4-, 5-, 6- or 7-azaindole, indazolyl, benzofuryl, benzthienyl, benzo[b]thiazolyl, benzoxazolyl, benzthiazolyl, benzimidazolyl, imidazo[b]thiazolyl, thieno[b]pyridyl, imidazo[a]pyridyl, pyrazo[a]pyridyl and pyrrol[d]pyrimidyl. Examples of 5- or 6-membered heteroaromatic compounds comprising an anellated cycloalkenyl ring include dihydroindolyl, dihydroindolizinyl, dihydroisoindolyl, dihydroquinolinyl, dihydroisoquinolinyl, dihydrobenzofuryl, chromenyl, chromanyl, dihydropyrrol[a]imidazolyl and tetrahydrobenzothiazolyl.

A non-aromatic 5- or 6-membered group (heterocyclic group) may be saturated or partially unsaturated and includes 1, 2 or 3 heteroatoms selected from O, N and S. The heterocyclic radicals may be bound via a carbon atom (C-bound) or a nitrogen atom (N-bound). Preferred heterocyclic groups comprise 1 nitrogen atom as ring member atom and optionally 1 or 2 further heteroatoms as ring members, which are selected, independently of each other from O, S and N. Examples are:

C-bound, 5-membered, saturated rings, such as
tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;
N-bound, 5-membered, saturated rings, such as tetrahydropyrrol-1-yl (pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as
piperidin-1-yl, hexahydropyrimidin-1-yl, hexahydropyrazin-1-yl (piperazin-1-yl), hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholin-1-yl), tetrahydro-1,2-oxazin-2-yl;

C-bound, 5-membered, partially unsaturated rings, such as
2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydro-pyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetra-hydropyridazin-5-yl, 1,2,5,6-tetrahydropyridazin-6-yl, 1,2,3,6-tetrahydro-pyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihdro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Any group containing heteroatoms may contain 1, 2 or 3 heteroatoms which may be the same or different.

The compounds of the invention, which means here and in the following the MKK4 inhibitors and the compounds of the invention including the pharmaceutically acceptable salts, prodrugs, biologically active metabolites, solvates and stereoisomers thereof, can be prepared as disclosed in WO 2007/002433 which is incorporated herein in its entirety by reference or according to analogous procedures. The acid or base addition salts are prepared in a customary manner by mixing the free base with a corresponding acid or by mixing the free acid with the desired base. Optionally, the reaction is carried out in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds of the invention are useful for promoting liver regeneration or reducing or preventing hepatocyte death and, at the same time, increasing hepatocyte proliferation. The compounds are therefore useful in treating, modulating, improving or preventing diseases which involve acute or chronic damages to the liver that may be caused by infection, injury, exposure to toxic compounds, an abnormal build-up of normal substances in the blood, an autoimmune process, a genetic defect or unknown causes.

Such liver diseases comprise all diseases where increased liver regeneration and reduction or prevention of hepatocyte death may be helpful to achieve a potential therapeutic effect, i.e. partial or complete restoration of liver functions. Such diseases comprise acute and chronic or acute on chronic liver diseases such as acute and chronic viral hepatitis like hepatitis B, C, E, hepatitis caused by Epstein-Barr virus, cytomegalovirus, herpes simplex virus and other viruses, all types of autoimmune hepatitis, primary sclerosing hepatitis, alcoholic hepatitis;

metabolic liver diseases such as metabolic syndrome, fatty liver like non-alcoholic fatty liver (NAFL), non-alcoholic steatohepatitis (NASH), alcoholic steatohepatitis (ASH), Morbus Wilson, Hemochromatosis, alpha1-antitrypsin deficiency, glycogen storage diseases;

all types of liver cirrhosis, such as primary biliary cirrhosis, ethyl toxic liver cirrhosis, cryptogenic cirrhosis;

acute (fulminant) or chronic liver failure such as toxic liver failure like acetaminophen (paracetamol) induced liver failure, alpha-amanitin induced liver failure, drug induced hepatotoxicity, liver failure caused, for example, by antibiotics, nonsteroidal anti-inflammatory drugs and anticonvulsants, acute liver failure induced by herbal supplements (kava, ephedra, skullcap, pennyroyal etc), liver disease and failure due to vascular diseases such as Budd-Chiari syndrome, acute liver failure of unknown origin, chronic liver disease due to right heart failure;

galactosemia, cystic fibrosis, porphyria, hepatic ischemia perfusion injury, small for size syndrome after liver transplantation, primary sclerosing cholangitis or hepatic encephalopathy.

For promoting liver regeneration or reducing or preventing hepatocyte death the compounds of the invention are administered to a patient in need thereof in a therapeutically effective amount. The presence of a liver disease can be detected by the existence of elevated enzyme levels in the blood. Blood levels of alanine aminotransferase (ALT) and aspartate aminotransferase (AST), above clinically accepted normal ranges, are known to be indicative of on-going liver damage. Blood bilirubin levels or other liver enzymes may be used as detection or diagnostic criteria. Routine monitoring of liver disease patients for blood levels of ALT and AST is used to measure progress of the liver disease while on medical treatment.

Reduction of elevated ALT and AST levels to within the accepted normal range is taken as clinical evidence reflecting a reduction in the severity of the patients liver damage.

The compounds of the invention are customarily administered in the form of pharmaceutical compositions which comprise at least one compound according to the invention, optionally together with an inert carrier (e.g. a pharmaceutically acceptable excipient) and, where appropriate, other drugs. These compositions can, for example, be administered orally, rectally, transdermally, subcutaneously, intraperitoneally, intravenously, intramuscularly or intranasally.

Examples of suitable pharmaceutical compositions are solid medicinal forms, such as powders, granules, tablets, in particular film tablets, lozenges, sachets, cachets, sugar-coated tablets, capsules, such as hard gelatin capsules and soft gelatin capsules, or suppositories, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resins; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Cantor-Verlag, 1996.

The compounds of the invention may also be suitable for combination with other therapeutic agents. The invention therefore further relates to a combination comprising a compound of the invention with one or more further therapeutic agents, in particular for use in promoting liver regeneration or reducing or preventing hepatocyte death. The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of the invention and at least one further therapeutic agent are within the scope of the current invention. In one embodiment of adjunctive therapeutic administration as described herein, a patient is typically stabilized on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

Suitable agents for use in combination with the compounds of the inventions include for example:

ACC inhibitors such as TOFA (5-(tetradecyloxy)-2-furoic acid), GS 0976, and ACC inhibitors as disclosed in WO 2016/112305, angiotensin II receptor antagonists, angiotensin converting enzyme (ACE) inhibitors, such as enalapril, caspase inhibitors, such as emricasan, cathepsin B inhibitors, such as a mixed cathepsin B/hepatitis C virus NS3 protease inhibitor. like VBY-376, CCR2 chemokine antagonists, such as a mixed CCR2/CCR5 chemokine antagonist like cenicriviroc, CCR5 chemokine antagonists, chloride channel stimulators, such as cobiprostone, cholesterol solubilizers, diacylglycerol 0-acyltransferase 1 (DGAT1) inhibitors, such as LCQ908, dipeptidyl peptidase IV (DPPIV) inhibitors, such as linagliptin, farnesoid X receptor (FXR) agonists, such as INT-747 (obeticholic acid) or GS-9674 (PX-102), FXR/TGR5 dual agonists, such as INT-767, galectin-3 inhibitors, such as GR-MD-02, glucagon-like peptide 1 (GLP1) agonists, such as liraglutide or exenatide, glutathione precursors, hepatitis C virus NS3 protease inhibitors, such as a mixed cathepsin B/hepatitis C virus NS3 protease inhibitor like VBY-376, HMG CoA reductase inhibitors, such as a statin like atorvastatin, 11ß-hydroxysteroid dehydrogenase (11ß-HSD1) inhibitors, such as R05093151, IL-1ßantagonists, IL-6 antagonists, such as a mixed IL-6/IL-1ß/TNFα ligand inhibitor like BLX-1002, IL-10 agonists, such as peg-ilodecakin, IL-17 antagonists, such as KD-025, ileal sodium bile acid cotransporter inhibitors, such as SHP-626, leptin analogs, such as metreleptin, 5-lipoxygenase inhibitors, such as a mixed 5-lipoxygenase/PDE3/PDE4/PLC inhibitor like tipelukast, LPL gene stimulators, such as alipogene tiparvovec, lysyl oxidase homolog 2 (LOXL2) inhibitors, such as an anti-LOXL2 antibody like GS-6624, PDE3 inhibitors, such as a mixed 5-lipoxygenase/PDE3/PDE4/PLC inhibitor like tipelukast, PDE4 inhibitors, such as ASP-9831 or a mixed 5-lipoxygenase/PDE3/PDE4/PLC inhibitor like tipelukast, phospholipase C (PLC) inhibitors, such as a mixed 5-lipoxygenase/PDE3/PDE4/PLC inhibitor like tipelukast, PPARα agonists, such as a mixed PPARα/δ agonist like GFT505, PPARγ agonists, such as pioglitazone, PPARδ agonists, Rho associated protein kinase 2 (ROCK2) inhibitors, such as KD-025, sodium glucose transporter-2 (SGLT2) inhibitors, such as remogliflozin etabonate, stearoyl CoA desaturase-1 inhibitors, such as aramchol or CVT-12805, thyroid hormone receptor ß agonists, such as MGL-3196, tumor necrosis factor α (TNFα) ligand inhibitors, transglutaminase inhibitors and transglutaminase inhibitor precursors, such as mercaptamine, PTPIb inhibitors, such as A119505, A220435, A321842, CPT633, ISIS-404173, JTT-551, MX-7014, MX-7091, MX-7102, NNC-521246, OTX-001, OTX-002, or TTP814 and ASK1 inhibitors such as GS4977.

In some embodiments, the one or more further therapeutic agents are selected from acetylsalicylic acid, alipogene tiparvovec, aramchol, atorvastatin, BLX-1002, cenicriviroc, cobiprostone, colesevelam, emncasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, GS-9674, remogliflozin etabonate, SHP-626, solithromycin, tipelukast, TRX-318, ursodeoxycholic acid, and VBY-376.

In some embodiments, one of the one or more further therapeutic agents is selected from acetylsalicylic acid, alipogene tiparvovec, aramchol, atorvastatin, BLX-1 002, and cenicriviroc.

The invention also relates to a method of selectively inhibiting protein kinase MKK4 over protein kinases JNK1 and MKK7, promoting liver regeneration or preventing hepatocyte death, the treatment of acute, acute-on-chronic or chronic liver disease, or for treating acute and chronic or acute on chronic liver diseases such as acute and chronic viral hepatitis like hepatitis B, C, E, hepatitis caused by Epstein-Barr virus, cytomegalovirus, herpes simplex virus and other viruses, all types of autoimmune hepatitis, primary sclerosing hepatitis, alcoholic hepatitis;

metabolic liver diseases such as metabolic syndrome, fatty liver like non-alcoholic fatty liver (NAFL), non-alcoholic steatohepatitis (NASH), alcoholic steatohepatitis (ASH), Morbus Wilson, hemochromatosis, alpha1-antitrypsin deficiency, glycogen storage diseases;

all types of liver cirrhosis, such as primary biliary cirrhosis, ethyl toxic liver cirrhosis, cryptogenic cirrhosis;

acute (fulminant) or chronic liver failure such as toxic liver failure like acetaminophen (paracetamol) induced liver failure, alpha-amanitin induced liver failure, drug induced hepatotoxicity and liver failure caused, for example, by antibiotics, nonsteroidal anti-inflammatory drugs, anticonvulsants, acute liver failure induced by herbal supplements (kava, ephedra, skullcap, pennyroyal etc.), liver disease and failure due to vascular diseases such as Budd-Chiari syndrome, acute liver failure of unknown origin, chronic liver disease due to right heart failure;

galactosemia, cystic fibrosis, porphyria, hepatic ischemia perfusion injury, small for size syndrome after liver transplantation, primary sclerosing cholangitis or hepatic encephalopathy, which comprises administering an effective amount of an MKK4 inhibitor or a compound or a composition as defined above to a subject in need thereof.

In an embodiment, the compounds of the invention are administered in a dosage of 0.2 to 15 mg/kg or 0.5 to 12 mg/kg of the subject being treated. The compounds can be administered once or several times a day. The compounds are administered over 4 to 12 weeks.

The following examples illustrate the invention without limiting it.

EXAMPLES

Abbreviations

ATP adenosintriphosphate
Boc$_2$O di-tert.-butyloxycarbonate
CDE 1,2-dimethyl-propylamine
CPME cyclopentylmethyl ether
DCE dichloroethane
DCM dichloromethane
DIPEA diisopropylethyl amine
(4-)DMAP (4-)dimethylaminopyridine
DME dimethyl ether
DMF dimethylformamide
DMSO dimethylsulfoxide
DPPA diphenylphosphoryl azide
DTT dithiothreitol
EtOAc ethyl acetate
HEPES 2-(4-(2-hydroxyethyl)-1-piperazinyl)-ethansulfonsäure
HOBt hydroxybenzotriazole
HPLC high performance liquid chromatography
IPA isopropylalcohol
LAH lithium aluminium hydride LDA lithium diisopropylamide
mCPBA m-perchlorobenzoic acid
MeCN acetonitrile
MeOH methanol
NIS N-iodosuccinimide
$Pd_2(dba)_3$ tris(dibenzylideneacetone)dipalladium(0)
$Pd(dppf)Cl_2$ [1,1'-Bis(diphenylphosphino)ferrocene]palladium(II)dichloride
PE petrolether
PMBCI p-methoxybenzyl chloride
Rt or RT room temperature
Sol. solution
TEA triethanolamine
TfOH triflic acid
THF tetrahydrofurane
TLC thin layer chromatography
Xantphos 4,5-bis(diphenylphosphino)-9,9-dimethylxanthene Example 1: Propane-1-sulfonic acid [3-(5-chloro-1H-pyrrolo[2,3-b]pyridine-3-carbonyl)-2,4-difluoro-phenyl}amide

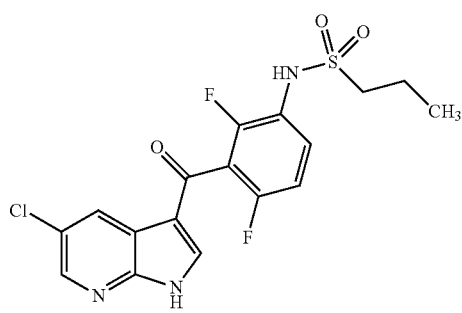 [SMILES: CCCS(=O)(=O)Nc1ccc(F)c(C(=O)c2c[nH]c3ncc(Cl)cc23)c1F]

prepared as disclosed in WO 2007/002433.

Example 2: Propane-1-sulfonic acid {3-[5-(4-chloro-phenyl)-1H-pyrrolo[2,3-b]pyridine-3-carbonyl]-2,4-difluoro-phenyl}-amide

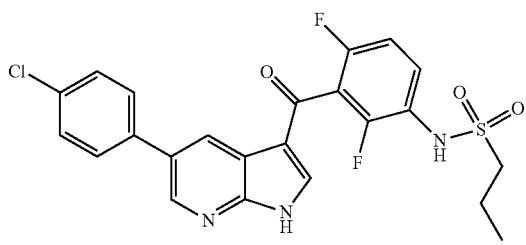 [SMILES: CCCS(=O)(=O)Nc1ccc(F)c(C(=O)c2c[nH]c3ncc(-c4ccc(Cl)cc4)cc23)c1F]

prepared as disclosed in WO 2007/002433.

For the preparation of compounds of the invention general procedures aa to ae were used:

General Procedure aa:
Oxalyl chloride (1.1 eq.) was added to a suspension of carboxylic acid (1.0 eq.) in dry DCM (0.5 m). Some drops of DMF were added and the resulting mixture was stirred at room temperature until the gas formation was complete. An excess of MeOH was added to the solution and the solvent was evaporated under reduced pressure. The residual was dried in vacuo and the product was used without further purification.

General Procedure ab:
Pd/C (0.1 eq.) was added to a solution of the nitrobenzene (1.0 eq.) in EtOH (0.2 m). The suspension was degassed with $H_2$ and the reaction was stirred at room temperature upon complete consumption of the starting material. Then, the mixture was passed through a Celite pad and the filtrate was concentrated in vacuum. The product was used without any further purification.

General Procedure ac:
A solution of aniline (1.0 eq.) and $Et_3N$ (2.2 eq.) in dry DCM (0.25 m) was cooled to 0° C. and the corresponding sulfonyl chloride was added dropwise. After complete addition the ice bath was removed and the solution was stirred at room temperature for ~1 h. The solution was then diluted with water, extracted with EtOAc and the combined organic layers were dried over $Na_2SO_4$. The solvent was removed under reduced pressure and the product was purified via flash chromatography ($SiO_2$, nHex/EtOAc 9/1).

The ester/disulfonamide was dissolved in THF/MeOH (1 m, 4:1), cooled to 0° C. and treated with $NaOH^{aq}$. (2 M, 2-3 eq.). After 10 min. the ice bath was removed and the reaction was stirred at room temperature until complete hydrolysis. THF/MeOH was removed in vacuo, the residual was treated with $HCl^{aq}$. (2 m) upon precipitating of the product. The precipitate was filtered of, dried and was used without any further purification.

General Procedure ad:
Aryl bromide (1 eq.), $K_2CO_3$ (2 eq.) and boronic acid/pinacol ester (1.2 eq.) were suspended in $DME/H_2O$ (0.15 m, 4:1) and degassed with argon for 10 min. $Pd(PPh_3)_4$ (0.05 eq.) was added and the suspension, which was then irradiated at 130° C. for 30 min (µw). The resulting mixture was passed through a Celite pad and the solvent was removed under reduced pressure. The crude mixture was purified via flash chromatography ($SiO_2$, DCM/MeOH (content of MeOH increased in 0.5%-steps from 0 to 5% (v/v)) to yield the titled compound.

General Procedure ae:
The carboxylic acid (1.1 eq.) was suspended in dry DCM (0.5 m), oxalyl chloride (1.05 eq.) and a few drops of DMF were added successively. After the gas formation stopped the resulting solution was added dropwise to a suspension of the azaindole (1 eq.) and $AlCl_3$ (5 eq.) in dry DCM (0.5 m). The mixture was stirred at room temperature for 0.5-3 h. Saturated, aqueous $NH_4Cl$ solution was added to quench the reaction. The water phase was extracted with EtOAc (3×), the combined organic layers were dried over $Na_2SO_4$ and the solvent was evaporated under reduced pressure. The product was purified via flash chromatography ($SiO_2$, nHex/EtOAc 1:1 or DCM/MeOH (content of MeOH increased in 0.5%-steps from 0 to 3% (v/v)) to yield the titled compound.

Methyl 2,6-difluoro-3-nitrobenzoate

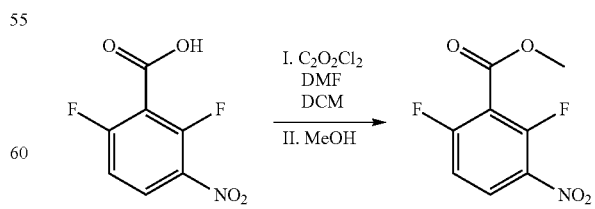

Procedure: The title compound was obtained by following GP aa.
Yield: 2.1 g, 9.4 mmol, 96% (white solid)
TLC: PE/EtOAc 3/1

¹H NMR (DMSO-d₆, 200 MHz, ppm): δ 8.45 (td, J=9.0, 5.6 Hz, 1H), 7.52 (td, J=9.4, 1.8 Hz, 1H), 3.95 (s, 3H); ¹³C NMR (DMSO-d₆, 50 Hz, ppm): δ 162.1 (dd, J=263.5, 5.7 Hz), 159.7, 153.6 (dd, J=271.1, 7.6 Hz), 134.4 (dd, J=7.5, 4.1 Hz), 130.6 (dd, J=12.0, 1.5 Hz), 113.4 (dd, J=23.8, 4.4 Hz), 112.2 (dd, J=20.3, 18.0 Hz), 53.6.

Methyl 3-amino-2,6-difluorobenzoate

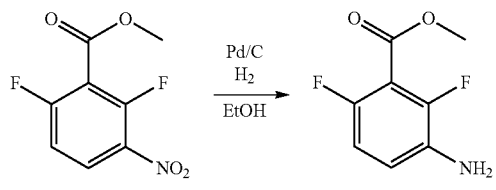

Procedure: The title compound was obtained by following GP ab.

Yield: 1.8 g, 9.7 mmol, 98%

TLC: PE/EtOAc 3:1

Methyl 2,6-difluoro-3-(N-(propylsulfonyl)propylsulfonamido)benzoate

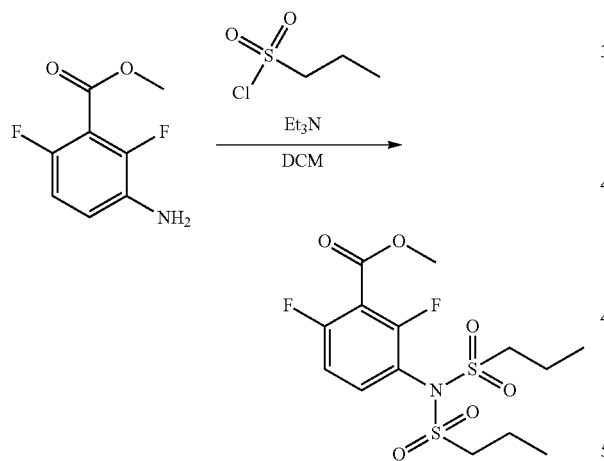

Procedure: The title compound was obtained by following the first part of GP ac.

Yield: 8.86 g, 22.2 mmol, 90%

TLC: PE/EtOAc 25%

¹H NMR (DMSO-d₆, 200 MHz, ppm): δ 7.95 (td, J=8.8, 5.8 Hz, 1H), 7.40 (t, J=8.9 Hz, 1H), 3.92 (s, 3H), 3.67 (td, J=7.3, 4.2 Hz, 4H), 1.92-1.70 (m, 4H), 1.01 (t, J=7.4 Hz, 6H); ¹³C NMR (DMSO-d₆, 50 Hz, ppm): δ 161.42 (dd, J=143.7, 6.7 Hz), 160.25 (t, J=1.3 Hz), 156.25 (dd, J=145.2, 6.7 Hz), 137.45 (d, J=11.1 Hz), 118.81 (dd, J=14.0, 4.1 Hz), 113.20 (dd, J=23.1, 4.0 Hz), 111.17 (dd, J=19.8, 17.9 Hz), 57.0, 53.3, 16.4, 12.4. TLC-MS: m/z calculated for C₁₄H₁₉F₂NO₆S₂ ([M-H]⁻): 398.4, found: 398.3.

2,6-Difluoro-3-(propylsulfonamido)benzoic acid

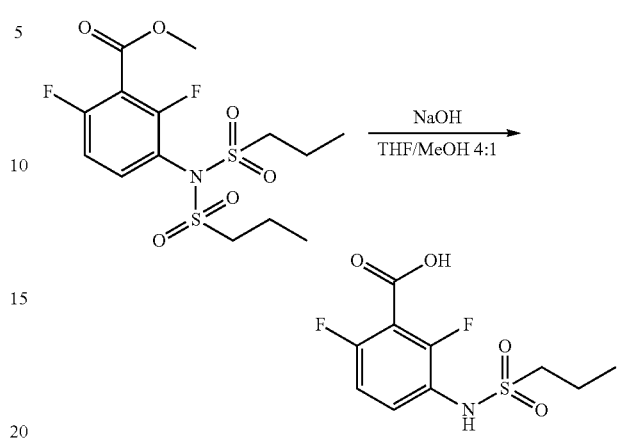

Procedure: The title compound was obtained by following the second part of GP ac.

Yield: 1.2 g, 4.2 mmol, 55%

TLC: PE/EtOAc 25%

¹H NMR (DMSO-d₆ 200 MHz, ppm): δ 14.01 (s, 1H), 9.74 (s, 1H), 7.54 (dd, J=14.8, 8.7 Hz, 1H), 7.20 (t, J=9.2 Hz, 1H), 3.15-3.02 (m, 2H), 1.85-1.63 (m, 2H), 0.97 (t, J=7.4 Hz, 3H); ¹³C NMR (DMSO-d₆, 50 Hz, ppm): δ 161.8, 157.3 (dd, J=174.8, 6.9 Hz), 152.3 (dd, J=178.1, 6.9 Hz), 129.8 (dd, J=10.2, 2.2 Hz), 122.0 (dd, J=13.5, 3.8 Hz), 112.8 (dd, J=21.3, 19.3 Hz), 112.3 (dd, J=22.6, 4.1 Hz), 53.8, 16.9, 12.6. TLC-MS: m/z calculated for C₁₀H₁₁F₂NO₄S ([M-H]⁻): 278.0, found: 278.0.

N-(3-(5-Bromo-1H-pyrrolo[2,3-b]pyridine-3-carbonyl)-2,4-difluorophenyl) propane-1-sulfonamide

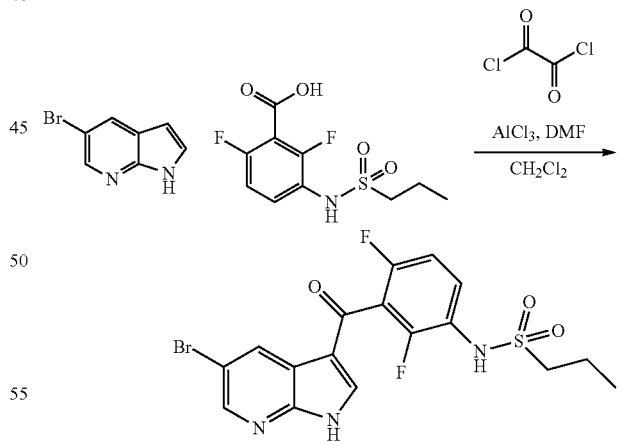

Procedure: The title compound was obtained by following GP ae.

Yield: 1.8 g, 3.9 mmol, 77%

TLC: PE/EtOAc 50%

¹H NMR (DMSO-d₆ 200 MHz, ppm): δ 13.14 (s, 1H), 9.78 (s, 1H), 8.59 (d, J=1.8 Hz, 1H), 8.51 (d, J=2.0 Hz, 1H), 8.28 (s, 1H), 7.59 (td, J=9.0, 6.4 Hz, 1H), 7.28 (t, J=8.8 Hz, 1H), 3.19-3.06 (m, 2H), 1.86-1.62 (m, 2H), 0.96 (t, J=7.3 Hz, 3H); ¹³C NMR (DMSO-d₆, 50 Hz, ppm): δ 180.6, 156.6

(dd, J=184.1, 7.6 Hz), 151.7 (dd, J=187.1, 7.7 Hz), 147.8, 145.3, 139.3, 131.1, 128.9 (dd, J=10.1, 2.1 Hz), 122.0 (dd, J=13.6, 3.8 Hz), 119.0, 117.8 (dd, J=24.3, 22.1 Hz), 114.9, 114.3, 112.4 (dd, J=22.8, 3.8 Hz), 53.5, 16.8, 12.6. TLC-MS: m/z calculated for $C_{17}H_{14}BrF_2N_3O_3S$ ([M-H]$^-$): 456.0, found: 456.1.

5-(4-Chlorophenyl)-1H-pyrrolo[2,3-b]pyridine

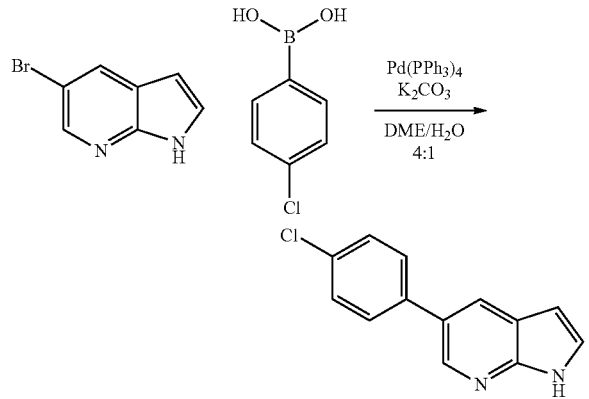

Procedure: 5-bromo-1H-pyrrolo[2,3-b]pyridine (2 g, 10.2 mmol, 1.0 eq.), $K_2CO_3$ (2.8 g, 20.3 mmol, 2 eq.) and (4-chlorphenyl)boronic acid (1.8 g, 11.2 mmol, 1.1 eq.) was suspended in DME/H$_2$O (30 ml, 4:1) and degassed with argon. Pd(PPh$_3$)$_4$ (587 mg, 508 µmol, 0.05 eq.) was added and the reaction mixture was heated under reflux until complete consumption of the starting material. The resulting solution was passed through a Celite pad, diluted with EtOAc and washed with water. The combined organic layers were dried over Na$_2$SO$_4$ and the solvent was evaporated under reduced pressure. The crude product was purified via flash chromatography (SiO$_2$, nHex/EtOAc 6:4).

Yield: 2.23 g, 9.4 mmol, 92% (white solid).

TLC: PE/EtOAc 1:1

$^1$H NMR (DMSO-d$_6$, 200 MHz, ppm): δ 11.76 (s, 1H), 8.51 (d, J=2.1 Hz, 1H), 8.20 (d, J=1.9 Hz, 1H), 7.72 (d, J=8.5 Hz, 2H), 7.57-7.43 (m, 3H), 6.50 (dd, J=3.2, 1.7 Hz, 1H); $^{13}$C NMR (DMSO-d$_6$, 50 Hz, ppm): δ 148.2, 141.4, 138.0, 131.7, 128.9, 128.6, 127.1, 126.9, 126.1, 119.7, 100.2.

Example 3: N-(2,4-Difluoro-3-(5-(4-methoxyphenyl)-1H-pyrrolo[2,3-b]pyridine-3-carbonyl) phenyl) propane-1-sulfonamide above)

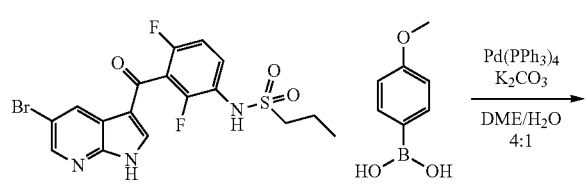

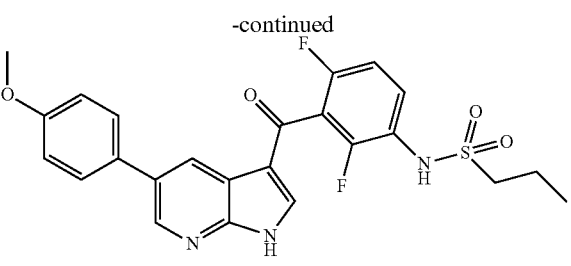

Procedure: The title compound was obtained by following GP ad.

Yield: 22.7 mg, 47 µmol, 36% (white solid)

TLC: DCM/MeOH 5%

$^1$H NMR (DMSO-d$_6$ 400 MHz, ppm): δ 12.96 (s, 1H), 9.78 (s, 1H), 8.67 (d, J=1.7 Hz, 1H), 8.57 (s, 1H), 8.21 (s, 1H), 7.68 (d, J=8.5 Hz, 2H), 7.59 (dd, J=14.8, 8.9 Hz, 1H), 7.28 (t, J=8.5 Hz, 1H), 7.08 (d, J=8.6 Hz, 2H), 3.82 (s, 3H), 3.19-3.06 (m, 2H), 1.74 (dq, J=14.7, 7.2 Hz, 2H), 0.96 (t, J=7.4 Hz, 3H); 13C NMR (DMSO-d$_6$, 101 Hz, ppm): δ 180.5, 159.0, 156.0 (dd, J=246.6, 6.9 Hz), 152.4 (dd, J=258.5, 8.9 Hz), 148.5, 143.7, 138.4, 131.3, 130.4, 128.7 (d, J=8.7 Hz), 128.2, 126.4, 121.9 (dd, J=13.1, 3.6 Hz), 118.2 (dd, J=25.0, 23.0 Hz), 117.5, 115.6, 114.6, 112.2 (dd, J=22.5, 3.3 Hz), 55.2, 53.5, 16.74, 12.5. TLC-MS: m/z calculated for $C_{24}H_{21}F_2N_3O_4S$ ([M-H]$^-$): 484.1, found: 484.2.

Example 4: N-(3-(5-(4-Cyanophenyl)-1H-pyrrolo[2,3-b]pyridine-3-carbonyl)-2,4-difluoro phenyl)propane-1-sulfonamide

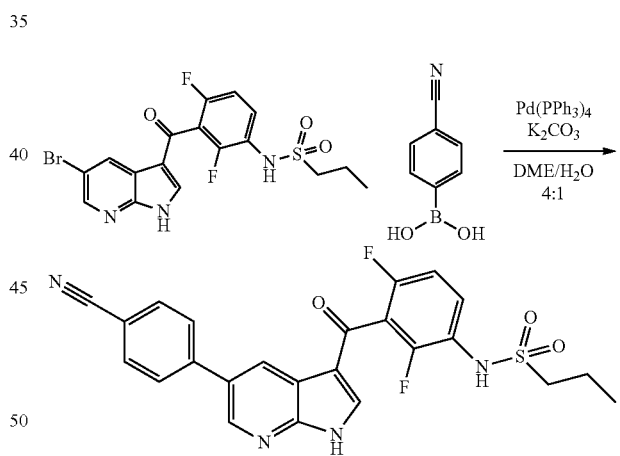

Procedure: The title compound was obtained by following GP ad.

Yield: 31 mg, 65 µmol, 49% (white solid)

TLC: DCM/MeOH 5%

$^1$H NMR (DMSO-d$_6$ 400 MHz, ppm): δ 13.10 (s, 1H), 9.79 (s, 1H), 8.80 (d, J=2.1 Hz, 1H), 8.73 (s, 1H), 8.29 (s, 1H), 8.00 (d, J=8.6 Hz, 2H), 7.97 (d, J=8.5 Hz, 2H), 7.60 (dd, J=14.8, 8.9 Hz, 1H), 7.29 (t, J=8.5 Hz, 1H), 3.17-3.09 (m, 2H), 1.81-1.68 (m, 2H), 0.97 (t, J=7.4 Hz, 3H); $^{13}$C NMR (DMSO-d$_6$, 101 Hz, ppm): δ 180.6, 156.0 (dd, J=246.8, 6.7 Hz), 152.4 (dd, J=249.8, 8.7 Hz), 149.4, 144.2, 142.8, 139.0, 132.9, 131.4 (d, J=9.6 Hz), 129.7, 128.7 (t, J=11.5 Hz), 128.0, 127.6, 121.9 (dd, J=13.2, 2.7 Hz), 118.8, 118.1 (dd, J=24.9, 22.1 Hz), 117.5, 115.8, 112.3 (dd, J=22.7, 3.6 Hz), 110.1, 53.6, 16.8, 12.5. TLC-MS: m/z calculated for $C_{24}H_{18}F_2N_4O_3S$ ([M-H]$^-$): 479.1, found: 479.2.

Example 5: N-(2,4-Difluoro-3-(5-(thiophen-2-yl)-1H-pyrrolo[2,3-b]pyridine-3-carbonyl) phenyl)propane-1-sulfonamide

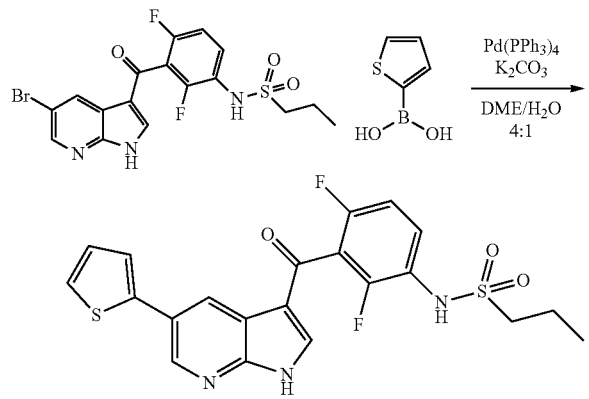

Procedure: The title compound was obtained by following GP ad.

Yield: 48 mg, 104 μmol, 79% (white solid)

TLC: DCM/MeOH 5%

$^1$H NMR (DMSO-d$_6$ 400 MHz, ppm): δ 13.04 (s, 1H), 9.79 (s, 1H), 8.78 (d, J=2.2 Hz, 1H), 8.60 (s, 1H), 8.24 (s, 1H), 7.65-7.53 (m, 3H), 7.29 (t, J=8.7 Hz, 1H), 7.20 (dd, J=5.0, 3.7 Hz, 1H), 3.16-3.08 (m, 2H), 1.80-1.68 (m, 2H), 0.96 (t, J=7.4 Hz, 3H); 13C NMR (DMSO-d$_6$, 101 Hz, ppm): δ 180.6, 156.0 (dd, J=246.4, 7.1 Hz), 152.3 (dd, J=249.6, 8.4 Hz), 148.7, 142.7, 140.7, 138.7, 128.8 (d, J=10.2 Hz), 128.7, 126.0, 125.5, 124.1, 121.9 (dd, J=13.8, 4.0 Hz), 117.5, 115.5, 112.3 (dd, J=22.6, 3.0 Hz), 53.5, 16.8, 12.5. TLC-MS: m/z calculated for $C_{21}H_{17}F_2N_3O_3S_2$ ([M-H]$^-$): 461.1, found: 461.2.

Example 6: N-(2,4-Difluoro-3-(5-(quinolin-3-yl)-1H-pyrrolo[2,3-b]pyridin-3-carbonyl) phenyl)propane-1-sulfonamide

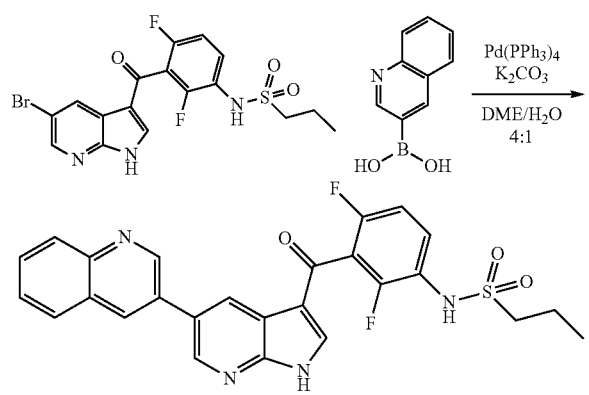

Procedure: The title compound was obtained by following GP ad.

Yield: 42 mg, 84 μmol, 64% (white solid)

TLC: DCM/MeOH 5%

$^1$H NMR (DMSO-d$_6$ 400 MHz, ppm): δ 13.10 (s, 1H), 9.80 (s, 1H), 9.34 (d, J=2.2 Hz, 1H), 8.93 (d, J=2.2 Hz, 1H), 8.86 (s, 1H), 8.79 (d, J=1.9 Hz, 1H), 8.31 (s, 1H), 8.11 (dd, J=13.0, 8.1 Hz, 2H), 7.84-7.77 (m, 1H), 7.68 (t, J=7.5 Hz, 1H), 7.60 (td, J=9.0, 6.0 Hz, 1H), 7.30 (t, J=8.7 Hz, 1H), 3.17-3.09 (m, 2H), 1.81-1.68 (m, 2H), 0.96 (t, J=7.4 Hz, 3H); $^{13}$C NMR (DMSO-d$_6$, 101 Hz, ppm): δ 180.7, 156.1 (dd, J=247.4, 6.2 Hz), 152.4 (dd, J=249.7, 8.4 Hz), 149.6, 149.2, 146.8, 144.4, 139.1, 133.5, 131.1, 129.7, 128.8 (d, J=9.7 Hz), 128.7, 128.5, 128.4, 127.7, 127.1, 122.0 (dd, J=13.8, 3.8 Hz), 118.2 (dd, J=25.6, 20.8 Hz), 117.6, 115.8, 112.4 (dd, J=22.8, 3.4 Hz), 53.5, 16.8, 12.6. TLC-MS: m/z calculated for $C_{26}H_{20}F_2N_4O_3S$ ([M-H]$^-$): 505.1, found: 505.1.

Example 7: N-(2,4-Difluoro-3-(5-(4-isopropylphenyl)-1H-pyrrolo[2,3-b]pyridine-3-carbonyl) phenyl) propane-1-sulfonamide

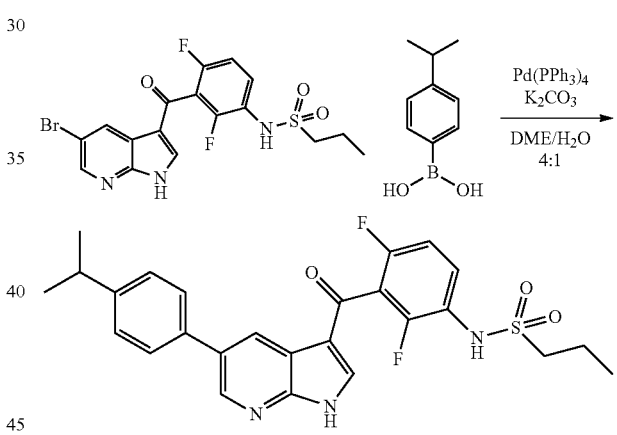

Procedure: The title compound was obtained by following GP ad.

Yield: 39 mg, 78 μmol, 60% (white solid)

TLC: DCM/MeOH 5%

$^1$H NMR (DMSO-d$_6$ 400 MHz, ppm): δ 12.99 (s, 1H), 9.79 (s, 1H), 8.69 (d, J=2.1 Hz, 1H), 8.60 (s, 1H), 8.23 (s, 1H), 7.66 (d, J=8.1 Hz, 2H), 7.59 (td, J=9.0, 6.0 Hz, 1H), 7.39 (d, J=8.2 Hz, 2H), 7.29 (t, J=8.4 Hz, 1H), 3.16-3.08 (m, 2H), 2.95 (sept, 1H), 1.80-1.68 (m, 2H), 1.25 (d, J=6.9 Hz, 6H), 0.96 (t, J=7.4 Hz, 3H); 13C NMR (DMSO-d$_6$, 101 Hz, ppm): δ 180.6, 156.0 (dd, J=246.7, 6.9 Hz), 152.3 (dd, J=250.0, 8.0 Hz), 148.7, 147.8, 143.9, 138.5, 135.6, 131.5, 128.73 (d, J=9.5 Hz), 127.1, 127.0, 126.7, 121.9 (dd, J=13.7, 3.3 Hz), 118.2 (dd, J=24.5, 22.9 Hz), 117.5, 115.6, 112.3 (dd, J=22.5, 3.1 Hz), 53.5, 33.1, 23.8, 16.8, 12.6. TLC-MS: m/z calculated for $C_{26}H_{25}F_2N_3O_3S$ ([M-H]$^-$): 496.2, found: 496.1.

Example 8: N-(2,4-Difluoro-3-(5-(4-(methylthio)phenyl)-1H-pyrrolo[2,3-b]pyridine-3-carbonyl)phenyl)propane-1-sulfonamide

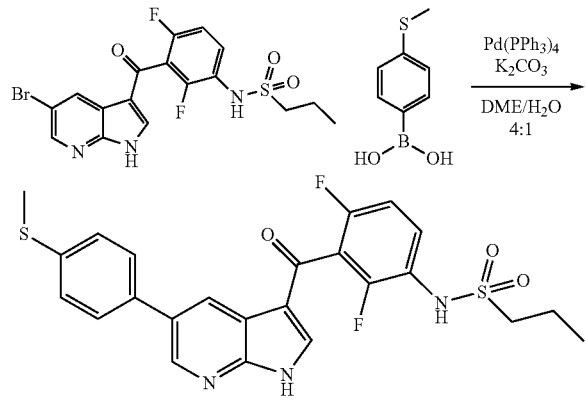

Procedure: The title compound was obtained by following GP ad.
Yield: 47 mg, 93 µmol, 71% (white solid)
TLC: DCM/MeOH 5%
$^1$H NMR (DMSO-$d_6$, 400 MHz, ppm): δ 13.00 (s, 1H), 9.78 (s, 1H), 8.70 (d, J=2.1 Hz, 1H), 8.62 (s, 1H), 8.23 (s, 1H), 7.71 (d, J=8.3 Hz, 2H), 7.63-7.56 (m, 1H), 7.40 (d, J=8.3 Hz, 2H), 7.29 (t, J=8.7 Hz, 1H), 3.16-3.09 (m, 2H), 2.53 (s, 3H), 1.80-1.69 (m, 2H), 0.96 (t, J=7.4 Hz, 3H); $^{13}$C NMR (DMSO-$d_6$, 101 MHz, ppm): δ 180.6, 156.0 (dd, J=246.7, 7.0 Hz), 152.3 (dd, J=249.8, 8.8 Hz), 148.8, 143.8, 138.6, 137.7, 134.6, 131.4 (d, J=9.8 Hz), 130.9, 128.7 (dd, J=10.9, 4.2 Hz), 127.5, 126.6, 121.92 (dd, J=13.4, 3.2 Hz), 118.2 (dd, J=24.5, 22.8 Hz), 117.5, 115.7, 112.3 (dd, J=22.5, 3.2 Hz), 53.5, 16.8, 14.7, 12.6. TLC-MS: m/z calculated for $C_{24}H_{21}F_2N_3O_3S_2$ ([M-H]$^-$): 500.1, found: 500.0.

Example 9: N-(2,4-Difluoro-3-(5-(2-hydroxyphenyl)-1H-pyrrolo[2,3-b]pyridine-3-carbonyl) phenyl)propane-1-sulfonamide

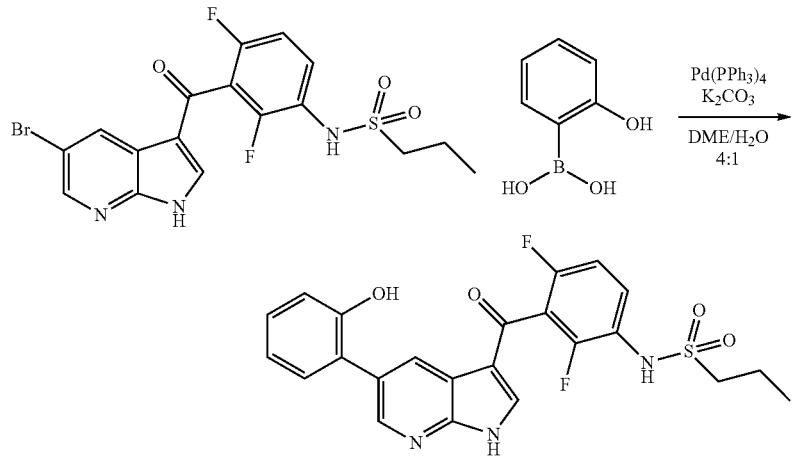

Procedure: The title compound was obtained by following GP ad.
Yield: 30 mg, 64 µmol, 49% (white solid)
TLC: DCM/MeOH 5%
$^1$H NMR (DMSO-$d_6$, 400 MHz, ppm): δ 12.91 (s, 1H), 9.77 (s, 1H), 9.69 (s, 1H), 8.62 (s, 1H), 8.54 (d, J=2.1 Hz, 1H), 8.18 (s, 1H), 7.58 (td, J=9.0, 5.9 Hz, 1H), 7.36 (dd, J=7.5, 1.2 Hz, 1H), 7.28 (t, J=8.4 Hz, 1H), 7.25-7.20 (m, 1H), 7.00 (d, J=7.7 Hz, 1H), 6.94 (t, J=7.4 Hz, 1H), 3.15-3.09 (m, 2H), 1.80-1.68 (m, 2H), 0.96 (t, J=7.4 Hz, 3H); 13C NMR (DMSO-$d_6$, 101 Hz, ppm): δ 180.5, 156.0 (dd, J=246.5, 6.9 Hz), 154.4, 152.27 (dd, J=249.5, 8.8 Hz), 148.1, 145.7, 138.1, 130.6, 129.5, 129.5, 128.8, 128.69-128.44 (m), 125.3, 121.9 (dd, J=13.2, 3.5 Hz), 119.6, 118.2 (t, J=23.8 Hz), 116.9, 116.0, 115.6, 112.2 (dd, J=23.1, 3.9 Hz), 53.5, 16.7, 12.5. TLC-MS: m/z calculated for $C_{23}H_{19}F_2N_3O_4S$ ([M-H]$^-$): 470.1, found: 470.4.

Example 10: N-(3-(5-(Benzo[d][1,3]dioxol-5-yl)-1H-pyrrolo[2,3-b]pyridine-3-carbonyl)-2,4-difluorophenyl)propane-1-sulfonamide

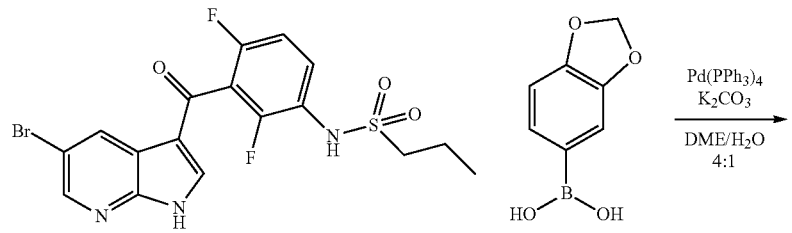

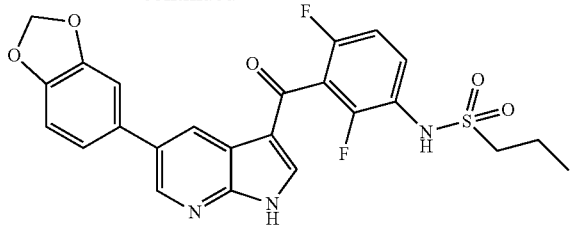

Procedure: The title compound was obtained by following GP ad.

Yield: 59 mg, 119 μmol, 91% (white solid)

TLC: DCM/MeOH 5%

$^1$H NMR (DMSO-$d_6$, 400 MHz, ppm): δ 12.96 (s, 1H), 9.77 (s, 1H), 8.64 (d, J=2.0 Hz, 1H), 8.56 (s, 1H), 8.20 (s, 1H), 7.67-7.50 (m, 1H), 7.33 (s, 1H), 7.28 (t, J=8.7 Hz, 1H), 7.20 (dd, J=8.1, 1.1 Hz, 1H), 7.05 (d, J=8.0 Hz, 1H), 6.09 (s, 2H), 3.17-3.08 (m, 2H), 1.82-1.69 (m, 2H), 0.97 (t, J=7.4 Hz, 3H); $^{13}$C NMR (DMSO-$d_6$, 101 Hz, ppm): δ 180.5, 156.0 (dd, J=246.7, 7.3 Hz), 152.3 (dd, J=249.7, 8.6 Hz), 148.6, 148.1, 147.0, 143.9, 138.4, 132.4, 131.5, 128.6 (d, J=11.8 Hz), 126.8, 122.0 (dd, J=13.8, 3.4 Hz), 120.8, 118.2 (dd, J=24.5, 22.7 Hz), 117.4, 115.7, 112.2 (dd, J=22.8, 3.4 Hz), 108.8, 107.5, 101.2, 53.6, 16.8, 12.5. TLC-MS: m/z calculated for $C_{24}H_{19}F_2N_3O_5S$ ([M-H]$^-$): 498.1, found: 498.3.

Example 11: N-(2,4-Difluoro-3-(5-(4-fluorophenyl)-1H-pyrrolo[2,3-b]pyridine-3-carbonyl) phenyl)propane-1-sulfonamide

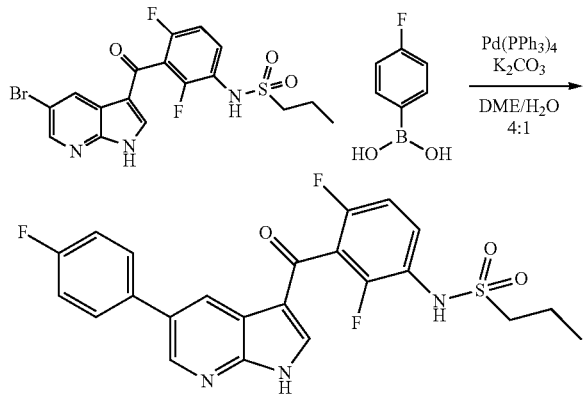

Procedure: The titled compound was yielded by following GP ad.

Yield: 55 mg, 115 μmol, 88% (white solid)

TLC: DCM/MeOH 5%

$^1$H NMR (DMSO-d6, 400 MHz, ppm): δ 12.99 (s, 1H), 9.78 (s, 1H), 8.69 (d, J=2.2 Hz, 1H), 8.62 (s, 1H), 8.25 (s, 1H), 7.80 (dd, J=8.6, 5.4 Hz, 2H), 7.59 (td, J=9.0, 5.9 Hz, 1H), 7.35 (t, J=8.8 Hz, 2H), 7.29 (t, J=8.7 Hz, 1H), 3.15-3.10 (m, 2H), 1.80-1.69 (m, 2H), 0.96 (t, J=7.4 Hz, 3H); $^{13}$C NMR (DMSO-$d_6$, 101 Hz, ppm): δ 180.6, 161.9 (d, J=244.6 Hz), 156.0 (dd, J=246.4, 6.9 Hz), 152.3 (dd, J=249.6, 8.6 Hz), 148.8, 143.9, 138.6, 134.6 (d, J=3.0 Hz), 130.6, 129.1 (d, J=8.2 Hz), 128.7 (dd, J=10.8, 4.2 Hz), 127.0, 121.9 (dd, J=13.6, 3.6 Hz), 118.1 (dd, J=24.4, 22.6 Hz), 117.4, 115.9 (d, J=21.4 Hz), 115.6, 112.2 (dd, J=22.9, 3.2 Hz), 53.5, 16.8, 12.5. TLC-MS: m/z calculated for $C_{23}H_{18}F_3N_3O_3S$ ([M-H]$^-$): 472.1, found: 472.3.

Example 12: N-(2,4-Difluoro-3-(5-(4-fluoro-2-methylphenyl)-1H-pyrrolo[2,3-b]pyridine-3-carbonyl)phenyl)propane-1-sulfonamide)

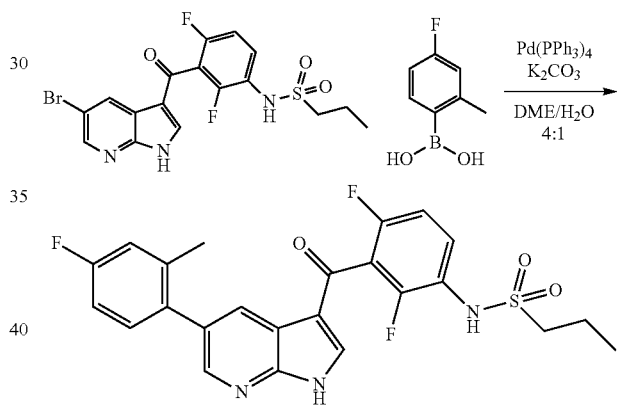

Procedure: The title compound was obtained by following GP ad.

Yield: 47 mg, 96 μmol, 73% (white solid)

TLC: DCM/MeOH 5%

$^1$H NMR (DMSO-$d_6$ 400 MHz, ppm): δ 13.02 (s, 1H), 9.78 (s, 1H), 8.37 (d, J=1.6 Hz, 1H), 8.34 (s, 1H), 8.26 (s, 1H), 7.58 (td, J=8.9, 6.1 Hz, 1H), 7.35 (dd, J=8.3, 6.2 Hz, 1H), 7.28 (t, J=8.7 Hz, 1H), 7.23 (dd, J=10.1, 2.4 Hz, 1H), 7.14 (td, J=8.5, 2.5 Hz, 1H), 3.16-3.09 (m, 2H), 2.26 (s, 3H), 1.80-1.69 (m, 2H), 0.96 (t, J=7.4 Hz, 3H); $^{13}$C NMR (DMSO-$d_6$, 101 Hz, ppm): δ 180.6, 161.6 (d, J=244.0 Hz), 156.0 (dd, J=246.4, 6.9 Hz), 152.3 (dd, J=249.5, 8.5 Hz), 148.4, 145.4, 138.5, 138.2 (d, J=8.1 Hz), 134.9 (d, J=2.9 Hz), 132.0 (d, J=8.5 Hz), 131.2, 129.3, 128.7 (d, J=9.8 Hz), 121.9 (dd, J=13.6, 3.5 Hz), 118.1 (dd, J=24.6, 22.3 Hz), 117.0, 116.73 (d, J=21.1 Hz), 115.5, 112.7 (d, J=20.9 Hz), 112.2 (dd, J=22.7, 3.5 Hz), 53.5, 20.2, 16.8, 12.5. TLC-MS: m/z calculated for $C_{24}H_{20}F_3N_3O_3S$ ([M-H]$^-$): 486.1, found: 486.3.

Example 13: N-(3-(5-(2-Chlorophenyl)-1H-pyrrolo[2,3-b]pyridine-3-carbonyl)-2,4-difluoro phenyl) propane-1-sulfonamide

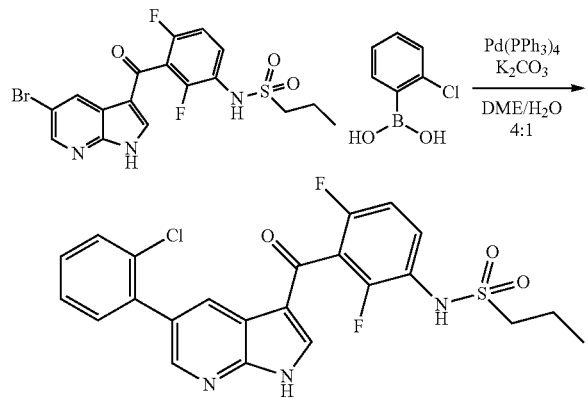

Procedure: The title compound was obtained by following GP ad.

Yield: 42 mg, 86 μmol, 66% (white solid)

TLC: DCM/MeOH 5%

$^1$H NMR (DMSO-$d_6$ 400 MHz, ppm): δ 13.07 (s, 1H), 9.78 (s, 1H), 8.49 (s, 1H), 8.46 (d, J=2.1 Hz, 1H), 8.28 (s, 1H), 7.66-7.54 (m, 3H), 7.52-7.43 (m, 2H), 7.28 (t, J=8.7 Hz, 1H), 3.16-3.08 (m, 2H), 1.80-1.68 (m, 2H), 0.96 (t, J=7.4 Hz, 3H); $^{13}$C NMR (DMSO-$d_6$, 101 Hz, ppm): δ 180.6, 156.0 (dd, J=246.6, 7.1 Hz), 152.3 (dd, J=249.6, 8.5 Hz), 148.6, 145.4, 138.7, 137.3, 132.0, 131.8, 129.8, 129.8, 129.7, 129.6, 128.7 (d, J=8.4 Hz), 127.6, 121.9 (dd, J=13.6, 3.6 Hz), 118.1 (dd, J=24.3, 22.6 Hz), 116.8, 115.6, 112.27 (dd, J=22.7, 3.6 Hz), 53.5, 16.8, 12.5. TLC-MS: m/z calculated for $C_{23}H_{18}ClF_2N_3O_3S$ ([M-H]$^-$): 488.1, found: 488.3.

Example 14: N-(3-(5-(3-Cyanophenyl)-1H-pyrrolo[2,3-b]pyridine-3-carbonyl)-2,4-difluoro phenyl) propane-1-sulfonamide

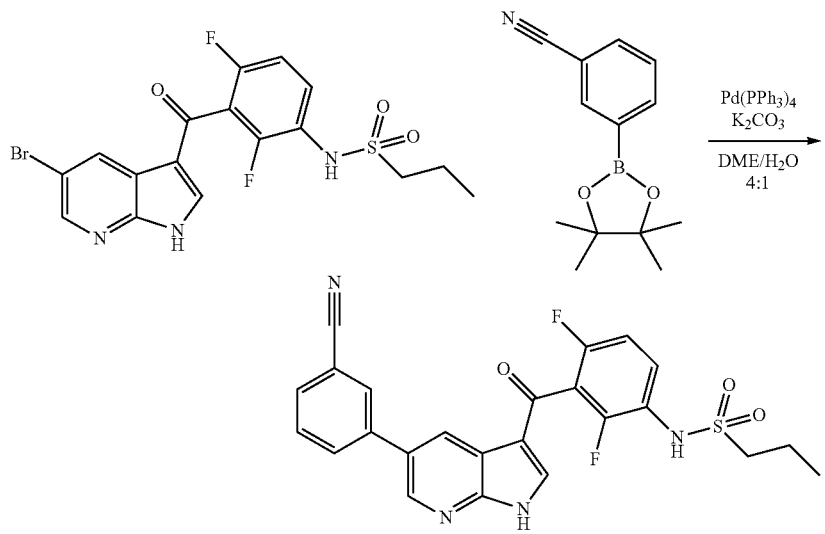

Procedure: The title compound was obtained by following GP ad.

Yield: 42 mg, 87 μmol, 67% (white solid)

TLC: DCM/MeOH 5%

$^1$H NMR (DMSO-$d_6$ 400 MHz, ppm): δ 13.06 (br. s., 1H), 9.79 (br. s, 1H), 8.78 (d, J=2.2 Hz, 1H), 8.73 (s, 1H), 8.28 (d, J=7.3 Hz, 2H), 8.12 (d, J=8.0 Hz, 1H), 7.88 (d, J=7.7 Hz, 1H), 7.72 (t, J=7.8 Hz, 1H), 7.59 (td, J=9.0, 6.0 Hz, 1H), 7.29 (t, J=8.7 Hz, 1H), 3.17-3.09 (m, 2H), 1.80-1.67 (m, 2H), 0.96 (t, J=7.4 Hz, 3H). $^{13}$C NMR (DMSO-$d_6$, 101 MHz, ppm): δ 180.6, 156.0 (dd, J=246.6, 6.9 Hz), 152.4 (dd, J=249.6, 8.2 Hz), 149.2, 144.2, 139.4, 138.9, 132.0, 131.1, 130.7, 130.2, 129.5, 128.8 (d, J=8.7 Hz), 127.6, 121.9 (dd, J=13.6, 3.4 Hz), 118.7, 118.1 (dd, J=24.6, 22.6 Hz), 117.4, 115.8, 112.3 (dd, J=22.7, 3.7 Hz), 112.2, 53.6, 16.8, 12.6. TLC-MS: m/z calculated for $C_{24}H_{18}F_2N_4O_3S$ ([M-H]$^-$): 479.1, found: 479.4.

Example 15: N-(3-(5-(2,3-Dihydrobenzo[b][1,4]dioxin-6-yl)-1H-pyrrolo[2,3-b]pyridine-3-carbonyl)-2,4-difluorophenyl)propane-1-sulfonamide

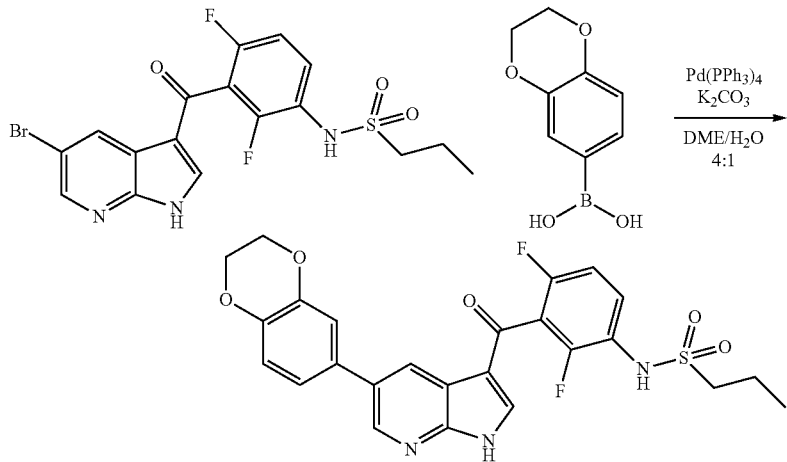

Procedure: The title compound was obtained by following GP ad.

Yield: 60 mg, 117 μmol, 89% (white solid)

TLC: DCM/MeOH 5%

$^1$H NMR (DMSO-$d_6$ 400 MHz, ppm): δ 12.97 (s, 1H), 9.79 (s, 1H), 8.64 (d, J=2.0 Hz, 1H), 8.55 (s, 1H), 8.21 (s, 1H), 7.65-7.51 (m, 2H), 7.28 (t, J=8.5 Hz, 1H), 7.24-7.16 (m, 2H), 6.99 (d, J=8.3 Hz, 1H), 4.29 (s, 4H), 3.17-3.07 (m, 2H), 1.74 (dq, J=14.9, 7.4 Hz, 2H), 0.96 (t, J=7.4 Hz, 3H). $^{13}$C NMR (DMSO-$d_6$ 101 MHz, ppm): δ 180.6, 156.0 (dd, J=246.4, 7.1 Hz), 152.4 (dd, J=249.6, 8.3 Hz), 148.6, 143.9, 143.8, 143.3, 138.5, 131.4, 131.2, 128.7 (d, J=11.8 Hz), 126.6, 122.0 (dd, J=13.7, 3.4 Hz), 120.0, 118.24 (dd, J=24.2, 22.1 Hz), 117.8, 117.5, 115.7, 115.6, 112.3 (dd, J=23.0, 3.6 Hz), 64.2, 64.2, 53.6, 16.8, 12.6. TLC-MS: m/z calculated for $C_{25}H_{21}F_2N_3O_5S$ ([M-H]$^-$): 512.1, found: 512.4.

Example 16: N-(3-(5-(3,4-Difluorophenyl)-1H-pyrrolo[2,3-b]pyridine-3-carbonyl)-2,4-difluorophenyl)propane-1-sulfonamide Procedure: The titled compound was yielded by following GP ad.

Yield: 51 mg, 104 μmol, 80% (white solid)

TLC: DCM/MeOH 5%

$^1$H NMR (DMSO-$d_6$ 400 MHz, ppm): δ 13.04 (s, 1H), 9.79 (s, 1H), 8.72 (d, J=2.1 Hz, 1H), 8.65 (s, 1H), 8.26 (s, 1H), 7.89 (ddd, J=9.7, 7.7, 1.5 Hz, 1H), 7.65-7.50 (m, 3H), 7.29 (t, J=8.4 Hz, 1H), 3.16-3.09 (m, 2H), 1.74 (dq, J=14.9, 7.4 Hz, 2H), 0.96 (t, J=7.4 Hz, 3H).

TLC-MS: m/z calculated for $C_{23}H_{17}F_4N_3O_3S$ ([M-H]$^-$): 490.1, found: 490.1.

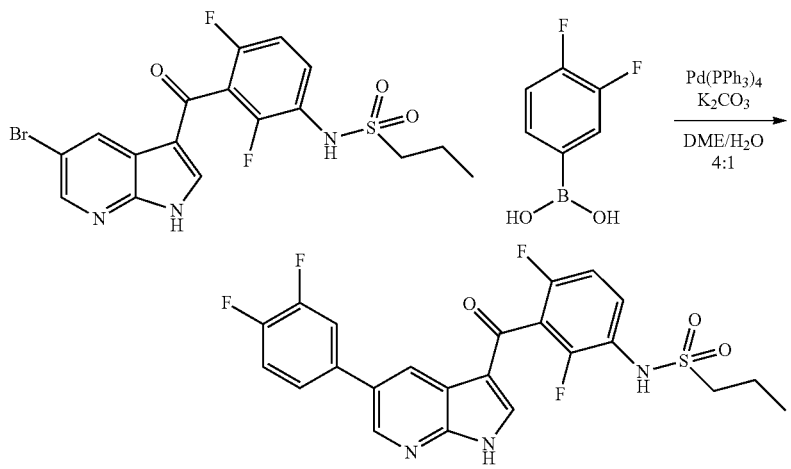

Example 17: N-(3-(5-(3,4-Difluorophenyl)-1H-pyrrolo[2,3-b]pyridine-3-carbonyl)-2,4-difluorophenyl)propane-1-sulfonamide

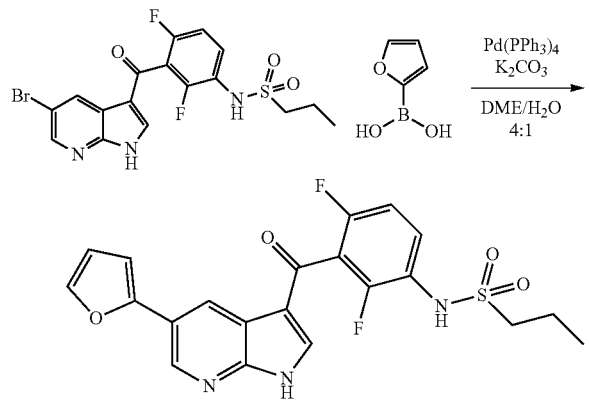

Procedure: The title compound was obtained by following GP ad.

Yield: 35 mg, 79 μmol, 60% (white solid)

TLC: DCM/MeOH 5%

$^1$H NMR (DMSO-$d_6$ 400 MHz, ppm): δ 13.02 (s, 1H), 9.79 (s, 1H), 8.83 (d, J=2.1 Hz, 1H), 8.70 (s, 1H), 8.23 (d, J=1.2 Hz, 1H), 7.82 (d, J=1.1 Hz, 1H), 7.59 (td, J=8.9, 6.0 Hz, 1H), 7.29 (t, J=8.4 Hz, 1H), 7.10 (d, J=3.2 Hz, 1H), 6.65 (dd, J=3.3, 1.8 Hz, 1H), 3.17-3.07 (m, 2H), 1.74 (dq, J=14.9, 7.4 Hz, 2H), 0.96 (t, J=7.4 Hz, 3H). $^{13}$C NMR (DMSO-$d_6$, 101 MHz, ppm): δ 180.6, 156.0 (dd, J=246.6, 6.7 Hz), 152.3 (dd, J=249.4, 8.1 Hz), 151.3, 148.5, 143.2, 141.5, 138.6, 128.8 (d, J=9.8 Hz), 123.5, 122.3, 121.9 (dd, J=13.3, 3.8 Hz), 118.5-117.8 (m), 117.3, 115.7, 112.5-112.2 (m), 112.2, 105.9, 53.5, 16.8, 12.6. TLC-MS: m/ calculated for $C_{21}H_{17}F_2N_3O_4S$ ([M-H]$^-$): 444.1, found: 444.1.

Example 18: N-(2,4-Difluoro-3-(5-(naphthalen-1-yl)-1H-pyrrolo[2,3-b]pyridine-3-carbonyl) phenyl)propane-1-sulfonamide

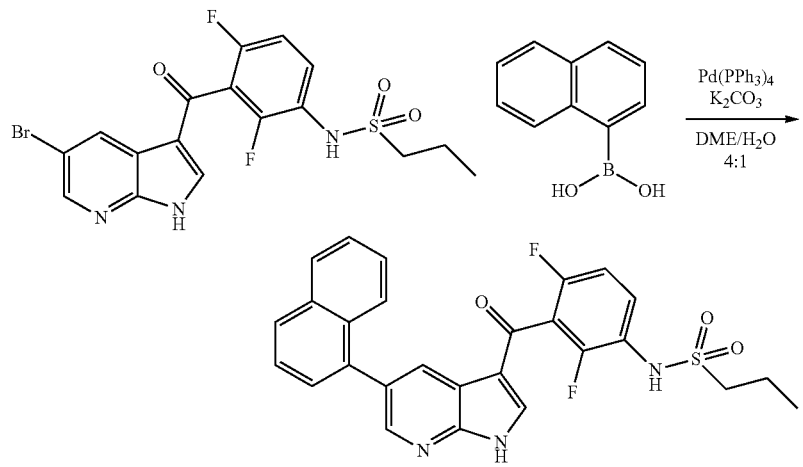

Procedure: The title compound was obtained by following GP ad.

Yield: 50 mg, 98 μmol, 75% (white solid)

TLC: DCM/MeOH 5%

$^1$H NMR (DMSO-$d_6$ 400 MHz, ppm): δ 13.11 (s, 1H), 9.80 (s, 1H), 8.52 (s, 1H), 8.51 (s, 1H), 8.30 (s, 1H), 8.03 (t, J=8.5 Hz, 2H), 7.80 (d, J=8.1 Hz, 1H), 7.66-7.50 (m, 5H), 7.28 (t, J=8.7 Hz, 1H), 3.15-3.08 (m, 2H), 1.79-1.67 (m, 2H), 0.96 (t, J=7.4 Hz, 3H). $^{13}$C NMR (DMSO-$d_6$, 101 MHz, ppm): δ 180.7, 156.1 (dd, J=246.4, 6.8 Hz), 152.4 (dd, J=249.5, 8.5 Hz), 148.8, 145.9, 138.8, 136.6, 133.5, 131.3, 131.0, 130.1, 128.8 (d, J=8.6 Hz), 128.5, 128.1, 127.9, 126.8, 126.1, 125.7, 125.0, 122.0 (dd, J=13.7, 3.4 Hz), 118.6-117.7 (m), 117.2, 115.7, 112.35 (dd, J=23.1, 3.3 Hz), 53.6, 16.8, 12.6. TLC-MS: m/z calculated for $C_{27}H_{21}F_2N_3O_3S$ ([M-H]$^-$): 504.1, found: 504.2.

Example 19: N-(3-(5-(3-Aminophenyl)-1H-pyrrolo[2,3-b]pyridine-3-carbonyl)-2,4-difluorophenyl)propane-1-sulfonamide

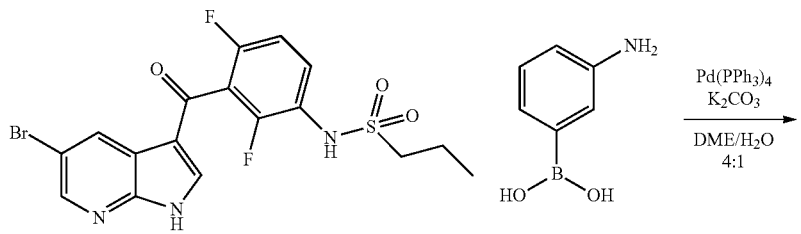

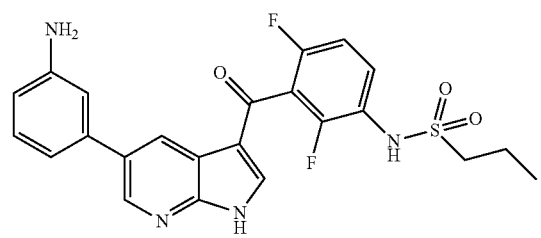

Procedure: The title compound was obtained by following GP ad.

Yield: 33 mg, 69 μmol, 53% (white solid)
TLC: DCM/MeOH 5%
$^1$H NMR (DMSO-$d_6$ 400 MHz, ppm): δ 12.97 (s, 1H), 9.79 (s, 1H), 8.62 (d, J=1.7 Hz, 1H), 8.59 (s, 1H), 8.21 (s, 1H), 7.59 (td, J=8.9, 6.1 Hz, 1H), 7.29 (t, J=8.6 Hz, 1H), 7.16 (t, J=7.8 Hz, 1H), 6.94 (s, 1H), 6.86 (d, J=7.5 Hz, 1H), 6.62 (dd, J=8.0, 1.0 Hz, 1H), 5.26 (s, 2H), 3.16-3.06 (m, 2H), 1.81-1.66 (m, 2H), 0.96 (t, J=7.4 Hz, 3H). $^{13}$C NMR (DMSO-$d_6$, 101 MHz, ppm): δ 180.6, 156.0 (dd, J=246.5, 7.2 Hz), 152.4 (dd, J=250.2, 8.1 Hz), 149.3, 148.8, 143.8, 138.7, 138.5, 132.3, 129.7, 129.0-128.5 (m), 126.7, 122.0 (dd, J=13.6, 3.5 Hz), 118.7-117.8 (m), 117.5, 115.7, 114.6, 113.3, 112.4, 112.2 (d, J=3.8 Hz), 53.6, 16.8, 12.6. TLC-MS: m/calculated for $C_{23}H_{20}F_2N_4O_3S$ ([M-H]$^-$): 469.1, found: 469.2.

Example 20

N-(3-(5-(4-Chlorophenyl)-1H-pyrrolo[2,3-b]pyridine-3-carbonyl)-2,4-difluorophenyl)ethanesulfonamide

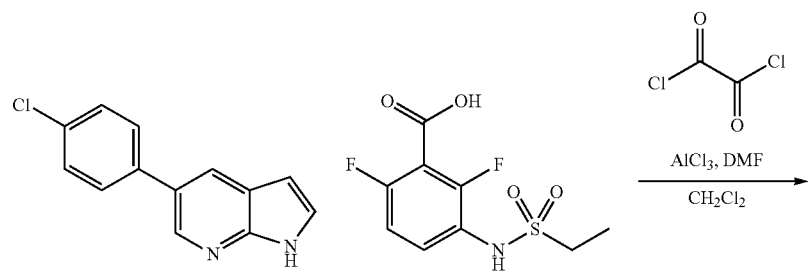

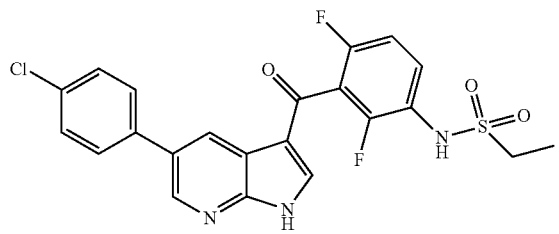

Procedure: The title compound was obtained by following GP af.

Yield: 40 mg, 85 μmol, 29% (white solid).

TLC: DCM/MeOH 5%

$^1$H NMR (DMSO-d$_6$, 200 MHz, ppm): δ 13.03 (s, 1H), 9.79 (s, 1H), 8.71 (d, J=2.0 Hz, 1H), 8.64 (s, 1H), 8.26 (s, 1H), 7.80 (d, J=8.5 Hz, 2H), 7.60 (m, 3H), 7.28 (t, J=8.5 Hz, 1H), 3.15 (q, 7.4 Hz, 2H), 1.26 (t, J=7.2 Hz, 3H). TLC-MS: m/z calculated for C$_{22}$H$_{16}$ClF$_2$N$_3$O$_3$S ([M-H]$^-$): 474.1, found: 474.1.

Example 21

N-(3-(5-(4-Chlorophenyl)-1H-pyrrolo[2,3-b]pyridine-3-carbonyl)-2,4-difluorophenyl)methanesulfonamide

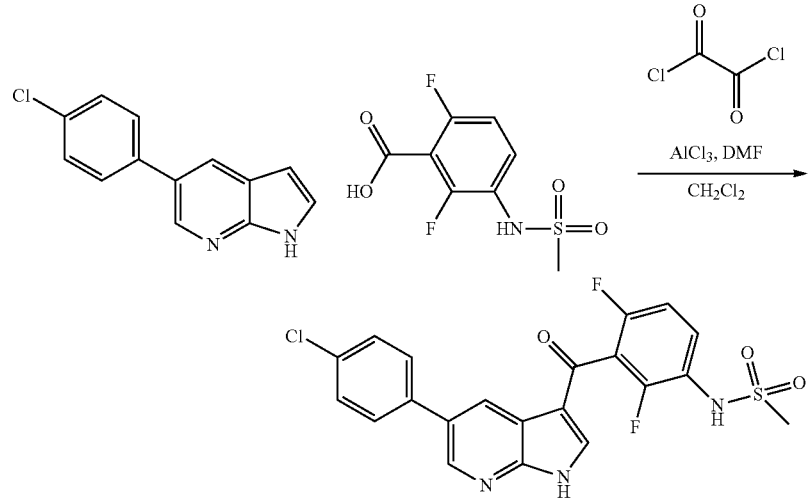

Procedure: The title compound was obtained by following GP ae.

Yield: 41 mg, 89 μmol, 30% (white solid).

TLC: DCM/MeOH 5%

$^1$H NMR (DMSO-d$_6$ 400 MHz, ppm): δ 13.03 (s, 1H), 9.76 (s, 1H), 8.71 (d, J=2.1 Hz, 1H), 8.66 (s, 1H), 8.27 (s, 1H), 7.80 (d, J=8.5 Hz, 2H), 7.63-7.54 (m, 3H), 7.30 (t, J=8.6 Hz, 1H), 3.08 (s, 3H). $^{13}$C NMR (DMSO-d$_6$, 101 Hz, ppm): δ 180.6, 156.1 (dd, J=247.3, 6.8 Hz), 152.6 (dd, J=249.8, 8.7 Hz), 149.0, 144.0, 138.9, 137.0, 132.5, 130.2, 129.0, 128.9, 127.5 (dd, J=35.1, 2.0 Hz), 127.1, 121.9 (dd, J=13.4, 3.8 Hz), 118.2 (dd, J=24.9, 22.5 Hz), 117.5, 115.7, 112.3 (dd, J=23.3, 4.0 Hz). TLC-MS: m/z calculated for C$_{21}$H$_{14}$ClF$_2$N$_3$O$_3$S ([M-H]$^-$): 460.0, found: 460.0.

Example 22

N-(3-(5-(4-Chlorophenyl)-1H-pyrrolo[2,3-b]pyridine-3-carbonyl)-2,4-difluorophenyl)butane-1-sulfonamide Step 1

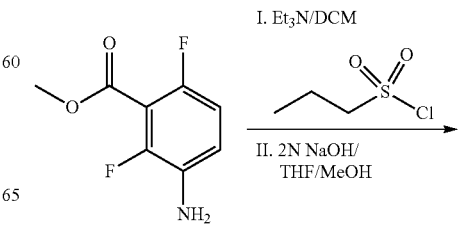

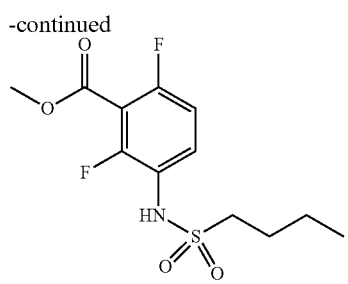

Step 2

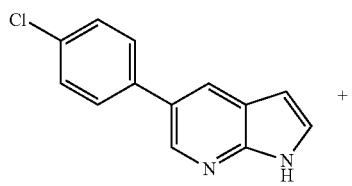

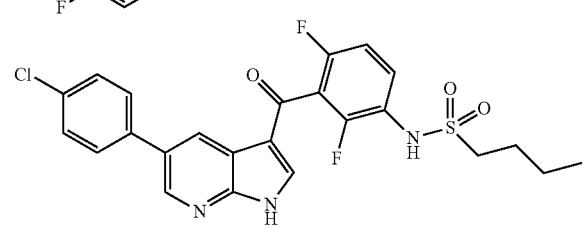

Step 1: 3-(Butylsulfonamido)-2,6-difluorobenzoic acid

Procedure: The title compound was obtained by following GP ac.

Yield: 211 mg, 720 μmol, 72% over 2 steps (off white solid).

TLC: PE/EtOAc 25%

$^1$H NMR (DMSO-$d_6$ 200 MHz, ppm): δ 14.05 (s, 1H), 9.75 (s, 1H), 7.54 (td, J=9.1, 6.3 Hz, 1H), 7.20 (t, J=9.2 Hz, 1H), 3.16-3.04 (m, 2H), 1.80-1.58 (m, 2H), 1.51-1.26 (m, 2H), 0.86 (t, J=7.2 Hz, 3H). $^{13}$C NMR (DMSO-$d_6$, 50 Hz, ppm): δ 161.8, 157.3 (dd, J=175.0, 6.8 Hz), 152.3 (dd, J=178.3, 6.9 Hz), 129.8 (dd, J=10.1, 2.2 Hz), 122.0 (dd, J=13.5, 3.8 Hz), 112.8 (dd, J=21.3, 19.3 Hz), 112.3 (dd, J=22.6, 4.1 Hz), 51.8, 25.2, 20.8, 13.5. TLC-MS: m/z calculated for $C_{11}H_{13}F_2NO_4S$ ([M-H]$^-$): 292.1, found: 292.1.

Step 2: N-(3-(5-(4-Chlorophenyl)-1H-pyrrolo[2,3-b]pyridine-3-carbonyl)-2,4-difluorophenyl)butane-1-sulfonamide Procedure: The title compound was obtained by following GP ae.

Yield: 49 mg, 97 μmol, 37% (white solid).

TLC: DCM/MeOH 5%

$^1$H NMR (DMSO-$d_6$ 400 MHz, ppm): δ 13.03 (s, 1H), 9.78 (s, 1H), 8.71 (d, J=2.1 Hz, 1H), 8.64 (s, 1H), 8.26 (s, 1H), 7.79 (d, J=8.5 Hz, 2H), 7.64-7.51 (m, 3H), 7.29 (t, J=8.6 Hz, 1H), 3.17-3.07 (m, 2H), 1.70 (dt, J=15.2, 7.6 Hz, 2H), 1.43-1.30 (m, 2H), 0.85 (t, J=7.3 Hz, 3H). $^{13}$C NMR (DMSO-$d_6$, 101 Hz, ppm): δ 180.6, 156.0 (dd, J=246.6, 7.1 Hz), 152.3 (dd, J=249.7, 8.5 Hz), 149.0, 143.9, 138.8, 137.0, 132.5, 130.2, 129.0, 128.9, 128.7 (m), 127.0, 121.9 (dd, J=13.8, 3.4 Hz), 118.51-117.74 (m), 117.4, 115.7, 112.3 (dd, J=23.1, 3.5 Hz), 51.6, 25.0, 20.7, 13.4). TLC-MS: m/z calculated for $C_{24}H_{20}ClF_2N_3O_3S$ ([M-H]$^-$): 502.1, found: 502.0.

Example 23

N-(3-(5-(4-Chlorophenyl)-1H-pyrrolo[2,3-b]pyridine-3-carbonyl)-2,4-difluorophenyl)-2-methylpropane-1-sulfonamide Step 1

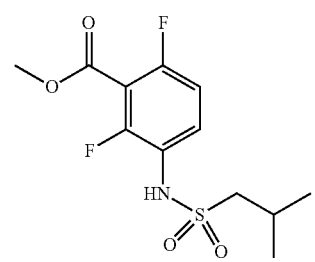

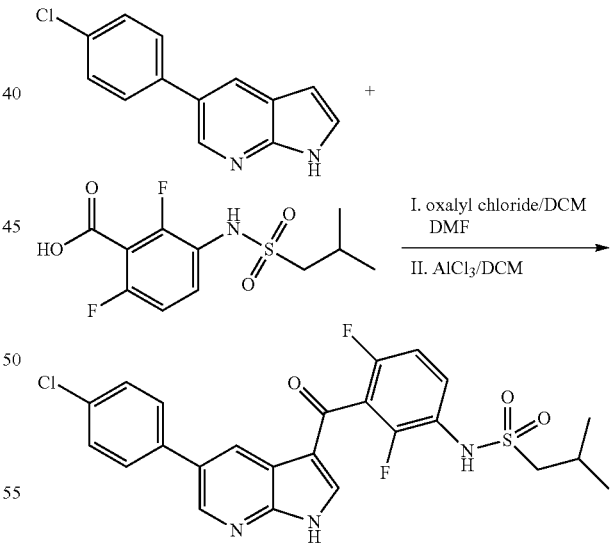

Step 1: 3-(Butylsulfonamido)-2,6-difluorobenzoic acid

Procedure: The title compound was obtained by following GP ac.

Yield: 192 mg, 655 μmol, 66% over 2 steps (off white solid).

TLC: PE/EtOAc 25%

$^1$H NMR (DMSO-d$_6$ 200 MHz, ppm): δ 14.10 (s, 1H), 9.76 (s, 1H), 7.54 (td, J=9.0, 5.9 Hz, 1H), 7.20 (td, J=9.1, 1.5 Hz, 1H), 3.01 (d, J=6.5 Hz, 2H), 2.28-2.04 (m, 1H), 1.02 (d, J=6.7 Hz, 6H). $^{13}$C NMR (DMSO-d$_6$, 50 Hz, ppm): δ 161.8, 157.3 (dd, J=177.4, 6.9 Hz), 152.2 (dd, J=180.7, 6.9 Hz), 129.7 (dd, J=10.1, 2.1 Hz), 122.0 (dd, J=13.4, 3.8 Hz), 112.8 (dd, J=21.3, 19.2 Hz), 112.3 (dd, J=22.6, 4.1 Hz), 59.6, 24.4, 22.1. TLC-MS: m/z calculated for C$_{11}$H$_{13}$F$_2$NO$_4$S ([M-H]$^-$): 292.1, found: 292.0.

Step 2: N-(3-(5-(4-Chlorophenyl)-1H-pyrrolo[2,3-b]pyridine-3-carbonyl)-2,4-difluorophenyl)-2-methyl-propane-1-sulfonamide Procedure: The title compound was obtained by following GP af.

Yield: 77 mg, 153 μmol, 58% (white solid).

TLC: DCM/MeOH 5%

$^1$H NMR (DMSO-d$_6$ 400 MHz, ppm): δ 13.03 (s, 1H), 9.79 (s, 1H), 8.71 (d, J=2.2 Hz, 1H), 8.65 (s, 1H), 8.26 (d, J=1.6 Hz, 1H), 7.79 (d, J=8.5 Hz, 1H), 7.64-7.53 (m, 1H), 7.29 (t, J=8.6 Hz, 1H), 3.05 (d, J=6.4 Hz, 1H), 2.26-2.09 (m, 1H), 1.02 (d, J=6.7 Hz, 1H). $^{13}$C NMR (DMSO-d$_6$, 101 Hz, ppm): δ 180.6, 156.0 (dd, J=246.7, 6.9 Hz), 152.2 (dd, J=249.5, 8.8 Hz), 149.0, 143.9, 138.7, 137.0, 132.5, 130.2, 129.0, 128.9, 128.6 (d, J=8.8 Hz), 127.0, 121.9 (dd, J=13.5, 2.9 Hz), 118.1 (dd, J=24.3, 22.0 Hz), 117.4, 115.7, 112.3 (dd, J=23.2, 3.1 Hz), 59.4, 24.3, 22.0. TLC-MS: m/z calculated for C$_{24}$H$_{20}$ClF$_2$N$_3$O$_3$S ([M-H]$^-$): 502.1, found: 501.9.

Example 24

N-(3-(5-(4-Chlorophenyl)-1H-pyrrolo[2,3-b]pyridine-3-carbonyl)-5-methylphenyl)propane-1-sulfonamide

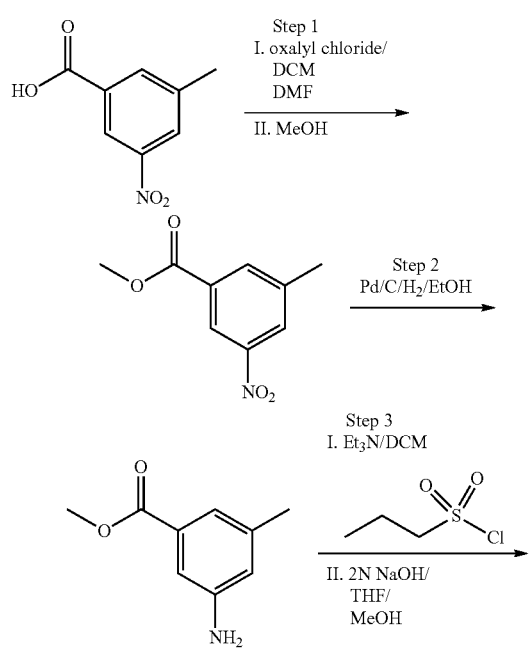

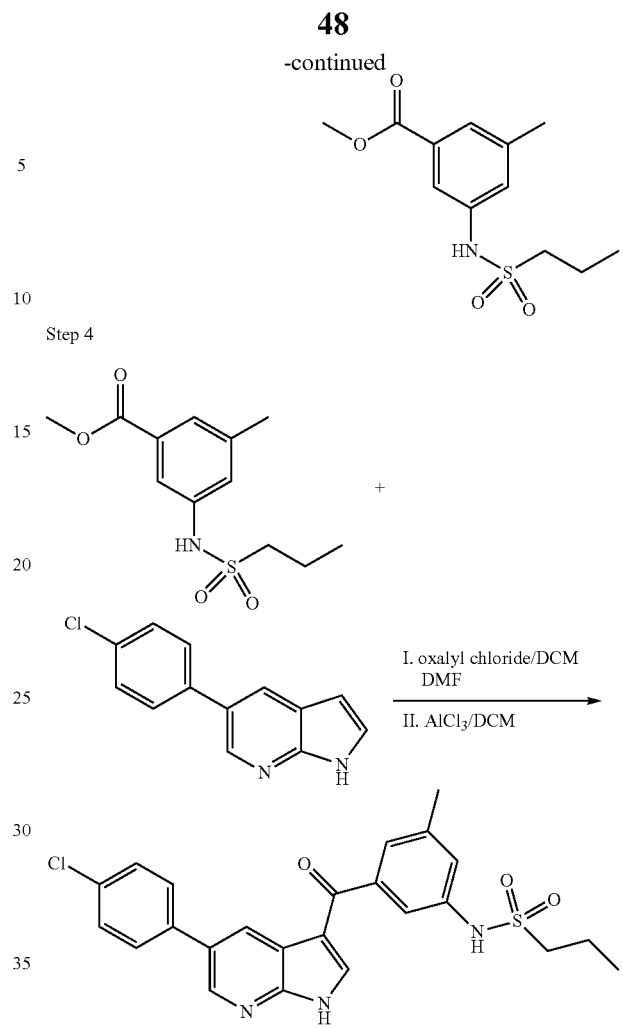

Step 1: Methyl 3-methyl-5-nitrobenzoate

Procedure: The title compound was obtained by following GP aa.

Yield: 535 mg, 2.7 mmol, 99% (beige solid).

TLC: PE/EtOAc 25%

$^1$H NMR (DMSO-d$_6$, 200 MHz, ppm): δ 8.40-8.36 (m, 1H), 8.30 (m, 1H), 8.17-8.13 (m, 1H), 3.90 (s, 3H), 2.49 (s, 3H). $^{13}$C NMR (DMSO-d$_6$, 50 Hz, ppm): δ 164.6, 147.8, 141.1, 135.6, 130.9 127.8, 120.8, 52.7, 20.4.

Step 2: Methyl 3-amino-5-methylbenzoate

Procedure: The title compound was obtained by following GP ab.

Yield: 446 mg, 2.7 mmol, 99% (dark yellow oil).

TLC: PE/EtOAc 25%

Step 3: 3-Methyl-5-(propylsulfonamido)benzoic acid

Procedure: The title compound was obtained by following GP ac. Divergent, in first step the reaction mixture was heated to reflux for at least 8 h, followed by usual work up.

Yield: 461 mg, 1.8 mmol, 65% (off white solid).

TLC: PE/EtOAc 25%

¹H NMR (DMSO-d$_6$, 200 MHz, ppm): δ 12.99 (s, 1H), 9.93 (s, 1H), 7.62 (s, 1H), 7.48 (s, 1H), 7.25 (s, 1H), 3.14-2.99 (m, 2H), 2.33 (s, 3H), 1.81-1.52 (m, 2H), 0.93 (t, J=7.5 Hz, 3H).

¹³C NMR (DMSO-d$_6$, 50 Hz, ppm): δ 167.02, 139.20, 138.69, 131.80, 125.10, 123.82, 117.14, 52.42, 21.00, 16.86, 12.54. TLC-MS: m/z calculated for C$_{11}$H$_{15}$NO$_4$S ([M-H]$^-$): 256.1, found: 256.0.

Step 4: N-(3-(5-(4-Chlorophenyl)-1H-pyrrolo[2,3-b]pyridine-3-carbonyl)-5-methylphenyl)propane-1-sulfonamide Procedure: The title compound was obtained by following GP ae.

Yield: 61 mg, 131 µmol, 50% (white solid).

TLC: DCM/MeOH 5%

¹H NMR (DMSO-d$_6$, 400 MHz, ppm): δ 12.82 (s, 1H), 9.96 (s, 1H), 8.72 (d, J=1.9 Hz, 1H), 8.68 (d, J=2.0 Hz, 1H), 8.16 (d, J=2.8 Hz, 1H), 7.77 (d, J=8.5 Hz, 2H), 7.56 (d, J=8.4 Hz, 2H), 7.49 (s, 1H), 7.37 (s, 1H), 7.27 (s, 1H), 3.20-3.04 (m, 2H), 2.39 (s, 3H), 1.71 (dq, J=14.9, 7.4 Hz, 2H), 0.95 (t, J=7.4 Hz, 3H). ¹³C NMR (DMSO-d$_6$, 101 Hz, ppm): δ 189.2, 148.7, 143.4, 140.4, 139.2, 138.5, 137.3, 136.5, 132.3, 129.6, 129.0, 128.8, 127.6, 124.2, 122.6, 118.7, 116.7, 113.8, 52.6, 21.1, 16.8, 12.5. TLC-MS: m/z calculated for C$_{24}$H$_{22}$ClN$_3$O$_3$S ([M-H]$^-$): 466.1, found: 466.0.

Example 25

N-(3-(5-(4-Chlorophenyl)-1H-pyrrolo[2,3-b]pyridine-3-carbonyl)-2-methyl phenyl)propane-1-sulfonamide

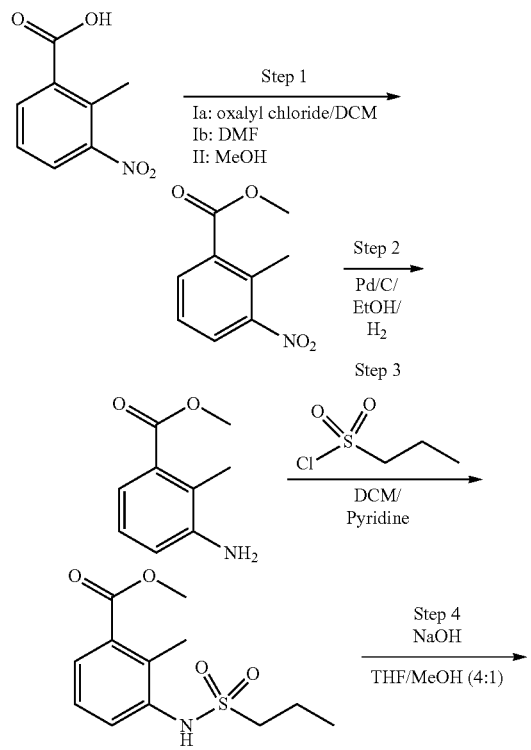

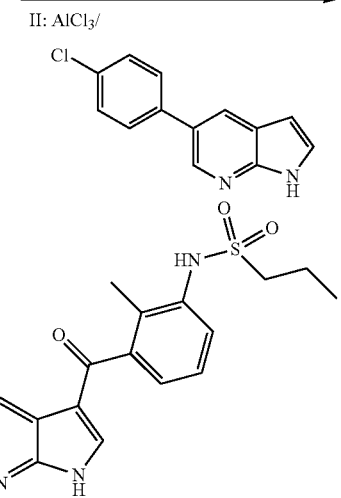

Step 1: Methyl 2-methyl-3-nitrobenzoate

Procedure: The title compound was obtained by following GP aa.

Yield: 1.1 g, 5.5 mmol, 99% (pale yellow solid).

TLC: PE/EtOAc 25%

¹H NMR (DMSO-d$_6$, 200 MHz, ppm): δ 8.03 (t, J=8.0 Hz, 2H), 7.56 (t, J=7.9 Hz, 1H), 3.89 (s, 3H), 2.49 (s, 3H). ¹³C NMR (DMSO-d$_6$, 50 Hz, ppm): δ 166.5, 151.5, 133.3, 133.1, 131.2, 127.3, 126.7, 52.7, 15.5.

Step 2: Methyl 3-amino-2-methylbenzoate

Procedure: The title compound was obtained by following GP ab.

Yield: 0.9 g, 5.3 mmol, 99% (brown oil).

TLC: PE/EtOAc 25%

Step 3: Methyl 2-methyl-3-(propylsulfonamido)benzoate

Procedure: Methyl 3-amino-2-methylbenzoate (914 mg, 5.5 mmol, 1 eq.) was dissolved in DCM (0.25 m), pyridine (980 µl, 12.2 mmol, 2.2 eq.) was added and the solution was treated with propane-1-sulfonyl chloride (1.4 ml, 12.2 mmol, 2.2 eq.). The resulting solution was refluxed overnight and then cooled to room temperature. Water was added to quench the reaction; the mixture was extracted with EtOAc and the combined organic layers were dried over Na$_2$SO$_4$. The solvent was removed under reduced pressure and the crude product was purified via flash chromatography (SiO$_2$, nHex/EtOAc 20%).

Yield: 1.4 g, 5.2 mmol, 94% (pale yellow oil).

TLC: PE/EtOAc 25%

¹H NMR (CDCl$_3$, 200 MHz, ppm): δ 7.66 (dd, J=7.9, 2.4 Hz, 2H), 7.26 (t, J=7.9 Hz, 1H), 6.50 (s, 1H), 3.90 (s, 3H), 3.13-3.00 (m, 2H), 2.51 (s, 3H), 1.97-1.75 (m, 2H), 1.03 (t, J=7.4 Hz, 3H). ¹³C NMR (CDCl$_3$, 50 Hz, ppm): δ 168.2, 136.1, 132.4, 131.5, 127.8, 126.7, 126.4, 54.4, 52.4, 17.4, 15.0, 13.1. TLC-MS: m/z calculated for C$_{12}$H$_{17}$NO$_4$S ([M-H]$^-$): 270.1, found: 269.9.

Step 4: 2-Methyl-3-(propylsulfonamido)benzoic acid

Procedure: The product was yielded by following the second part of GP ac with 2 eq. of NaOH.

Yield: 1.2 g, 4.5 mmol, 86% (white solid).

TLC: PE/EtOAc 50%

$^1$H NMR (DMSO-$d_6$ 200 MHz, ppm): δ 12.99 (s, 1H), 9.20 (s, 1H), 7.61 (d, J=7.4 Hz, 1H), 7.43 (d, J=7.9 Hz, 1H), 7.27 (t, J=7.7 Hz, 1H), 3.14-3.00 (m, 2H), 2.46 (s, 3H), 1.87-1.62 (m, 2H), 0.98 (t, J=7.4 Hz, 3H). $^{13}$C NMR (DMSO-$d_6$, 50 Hz, ppm): δ 169.0, 136.5, 134.82 (s), 133.4, 129.6, 127.5, 126.0, 53.8, 16.9, 15.6, 12.7. TLC-MS: m/z calculated for $C_{11}H_{15}NO_4S$ ([M-H]$^-$): 256.1, found: 225.9.

Step 5: N-(3-(5-(4-Chlorophenyl)-1H-pyrrolo[2,3-b]pyridine-3-carbonyl)-2-methyl phenyl)propane-1-sulfonamide Procedure: The title compound was obtained by following GP af.

Yield: 65 mg, 140 μmol, 53% (white solid).

TLC: DCM/MeOH 5%

$^1$H NMR (DMSO-$d_6$ 400 MHz, ppm): δ 12.81 (s, 1H), 9.25 (s, 1H), 8.67 (d, J=2.1 Hz, 1H), 8.54 (s, 1H), 7.85 (d, J=2.2 Hz, 1H), 7.75 (d, J=8.5 Hz, 2H), 7.55 (d, J=8.4 Hz, 2H), 7.44 (t, J=7.4 Hz, 1H), 7.38-7.24 (m, 2H), 3.15-3.09 (m, 2H), 2.25 (s, 3H), 1.76 (dq, J=15.4, 7.7 Hz, 2H), 0.99 (t, J=7.4 Hz, 3H). $^{13}$C NMR (DMSO-$d_6$, 101 Hz, ppm): δ 191.6, 168.9, 148.8, 143.4, 141.9, 137.2, 136.4, 132.4, 131.2, 129.7, 129.0, 128.8, 127.2, 127.2, 126.0, 124.9, 118.0, 115.4, 53.8, 16.9, 15.1, 12.6. TLC-MS: m/z calculated for $C_{24}H_{22}ClN_3O_3S$ ([M-H]$^-$): 466.1, found: 466.1.

Example 26

N-(3-(5-(4-Chlorophenyl)-1H-pyrrolo[2,3-b]pyridine-3-carbonyl)-4-methyl phenyl)propane-1-sulfonamide

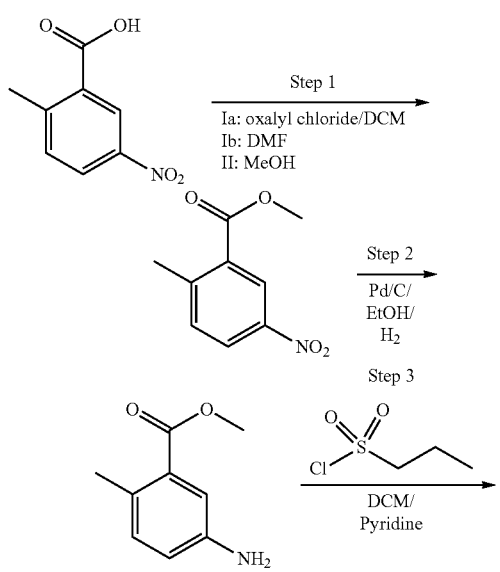

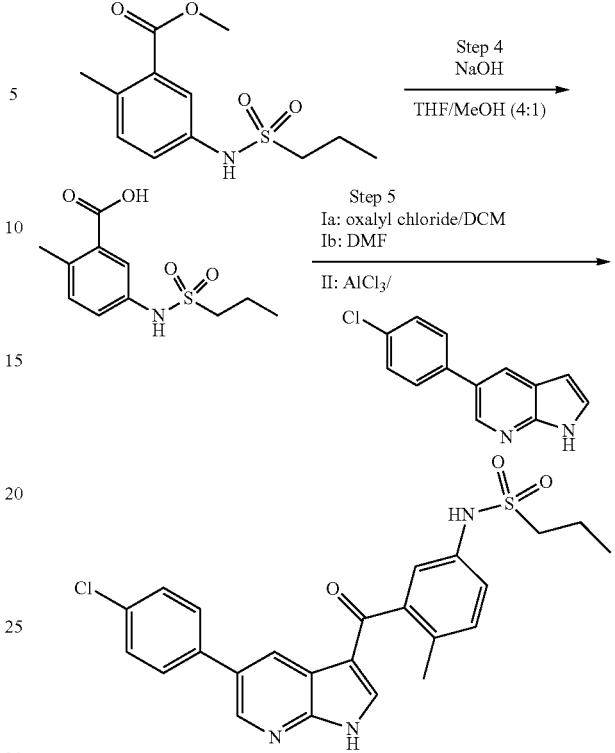

Step 1: Methyl 2-methyl-5-nitrobenzoate

Procedure: The title compound was obtained by following GP aa.

Yield: 1.0 g, 5.4 mmol, 97% (white solid).

TLC: PE/EtOAc 25%

$^1$H NMR (DMSO-$d_6$, 200 MHz, ppm): δ 8.52 (d, J=2.4 Hz, 1H), 8.29 (dd, J=8.5, 2.6 Hz, 1H), 7.62 (d, J=8.5 Hz, 1H), 3.88 (s, 3H), 2.62 (s, 3H). $^{13}$C NMR (DMSO-$d_6$, 50 Hz, ppm): δ 165.5, 147.2, 145.5, 133.2, 130.3, 126.3, 124.7, 52.5, 21.1.

Step 2: Methyl 5-amino-2-methylbenzoate

Procedure: The title compound was obtained by following GP ab.

Yield: 0.9 g, 5.3 mmol, 99% (beige oil).

TLC: PE/EtOAc 25%

Step 3: Methyl 2-methyl-5-(propylsulfonamido)benzoate

Procedure: Methyl 5-amino-2-methylbenzoate (914 mg, 5.5 mmol, 1 eq.) was dissolved in DCM (0.25 m), pyridine (980 μl, 12.2 mmol, 2.2 eq.) was added and the solution was treated with propane-1-sulfonyl chloride (1.4 ml, 12.2 mmol, 2.2 eq.). The resulting solution was refluxed overnight and then cooled to room temperature. Water was added to quench the reaction, the mixture was extracted with EtOAc and the combined organic layers were dried over $Na_2SO_4$. The solvent was removed under reduced pressure and the crude product was purified via flash chromatography ($SiO_2$, nHex/EtOAc 20%).

Yield: 1.4 g, 5.1 mmol, 93% (colorless oil).

TLC: PE/EtOAc 25%

¹H NMR (CDCl₃, 200 MHz, ppm): δ 7.74 (d, J=2.5 Hz, 1H), 7.35 (dd, J=8.2, 2.5 Hz, 1H), 7.23 (t, J=6.7 Hz, 1H), 7.09 (s, 1H), 3.89 (s, 3H), 3.11-3.00 (m, 2H), 2.55 (s, 3H), 1.96-1.74 (m, 2H), 1.00 (t, J=7.4 Hz, 3H). ¹³C NMR (CDCl₃, 50 Hz, ppm): δ 167.5, 137.2, 134.8, 133.1, 130.7, 124.5, 122.9, 53.4, 52.3, 21.2, 17.3, 13.0. TLC-MS: m/z calculated for $C_{12}H_{17}NO_4S$ ([M-H]⁻): 270.1, found: 269.8.

Step 4: 2-Methyl-5-(propylsulfonamido)benzoic acid

Procedure: The product was yielded by following the second part of GP ac with 2 eq. of NaOH.
Yield: 1.0 g, 4.0 mmol, 79% (white solid).
TLC: PE/EtOAc 50%
¹H NMR (DMSO-d₆, 200 MHz, ppm): δ 12.92 (s, 1H), 9.82 (s, 1H), 7.69 (d, J=2.0 Hz, 1H), 7.36-7.12 (m, 2H), 3.09-2.94 (m, 2H), 2.45 (s, 3H), 1.78-1.54 (m, 2H), 0.92 (t, J=7.4 Hz, 3H). ¹³C NMR (DMSO-d₆, 50 Hz, ppm): 5168.2, 136.2, 134.3, 132.5, 131.2, 122.9, 121.3, 52.3, 20.6, 16.8, 12.5. TLC-MS: m/z calculated for $C_{11}H_{15}NO_4S$ ([M-H]⁻): 256.1, found: 225.9.

Step 5: N-(3-(5-(4-Chlorophenyl)-1H-pyrrolo[2,3-b]pyridine-3-carbonyl)-4-methyl phenyl)propane-1-sulfonamide Procedure: The title compound was obtained by following GP af.
Yield: 99 mg, 211 μmol, 80% (white solid).
TLC: DCM/MeOH 5%
¹H NMR (DMSO-d₆ 400 MHz, ppm): δ 12.83 (s, 1H), 9.83 (s, 1H), 8.68 (d, J=1.9 Hz, 1H), 8.63 (s, 1H), 7.91 (d, J=2.6 Hz, 1H), 7.77 (d, J=8.4 Hz, 2H), 7.56 (d, J=8.4 Hz, 2H), 7.36-7.24 (m, 3H), 3.11-3.03 (m, 2H), 2.25 (s, 3H), 1.74-1.62 (m, 2H), 0.93 (t, J=7.4 Hz, 3H). ¹³C NMR (DMSO-d₆, 101 Hz, ppm): δ 191.2, 148.8, 143.5, 140.4, 137.2, 135.7, 132.4, 131.7, 130.6, 129.8, 129.0, 128.8, 127.4, 121.0, 119.1, 118.1, 115.1, 52.4, 18.46, 16.8, 12.5.
TLC-MS: m/z calculated for $C_{24}H_{22}ClN_3O_3S$ ([M-H]⁻): 466.1, found: 466.1.

Example 27

N-(3-(5-(4-Chlorophenyl)-1H-pyrrolo[2,3-b]pyridine-3-carbonyl)-2-fluorophenyl)propane-1-sulfonamide

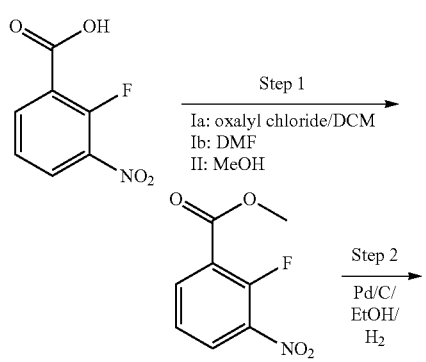

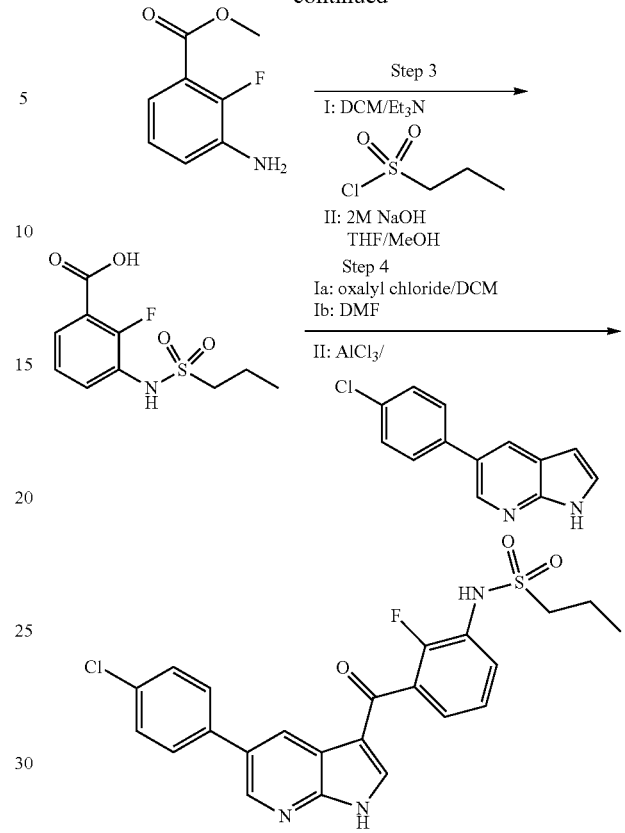

Step 1: Methyl 2-fluoro-3-nitrobenzoate

Procedure: The title compound was obtained by following GP aa.
Yield: 1.1 g, 5.4 mmol, 99% (pale yellow solid).
TLC: PE/EtOAc 25%
¹H NMR (DMSO-d₆, 200 MHz, ppm): δ 8.37 (ddd, J=8.7, 7.0, 1.8 Hz, 1H), 8.22 (ddd, J=8.2, 6.4, 1.8 Hz, 1H), 7.55 (td, J=8.2, 1.2 Hz, 1H), 3.90 (s, 3H). ¹³C NMR (DMSO-d₆, 50 Hz, ppm): δ 162.6 (d, J=3.2 Hz), 153.7 (d, J=274.1 Hz), 138.3 (d, J=8.9 Hz), 137.1 (d, J=1.8 Hz), 130.4 (d, J=2.0 Hz), 125.0 (d, J=5.4 Hz), 120.7 (d, J=9.7 Hz), 52.9.

Step 2: Methyl 3-amino-2-fluorobenzoate

Procedure: The title compound was obtained by following GP ab.
Yield: 0.9 g, 5.3 mmol, 99% (brown oil).
TLC: PE/EtOAc 25%

Step 3: 2-Fluoro-3-(propylsulfonamido)benzoic acid

Procedure: The title compound was obtained by following GP ac.
Yield: 754 mg, 2.9 mmol, 55% over 2 steps (white solid).
TLC: PE/EtOAc 25%
¹H NMR (DMSO-d₆, 200 MHz, ppm): δ 13.39 (s, 1H), 9.78 (s, 1H), 7.72-7.56 (m, 2H), 7.26 (t, J=8.0 Hz, 1H), 3.16-3.04 (m, 2H), 1.86-1.62 (m, 2H), 0.96 (t, J=7.4 Hz, 3H). ¹³C NMR (DMSO-d₆, 50 Hz, ppm): δ 164.8 (d, J=2.9 Hz), 154.5 (d, J=258.9 Hz), 130.3 (d, J=1.8 Hz), 128.3, 126.3 (d, J=13.4 Hz), 124.3 (d, J=4.9 Hz), 120.3 (d, J=9.6

Hz), 53.8, 16.9, 12.6. TLC-MS: m/z calculated for $C_{10}H_{12}FNO_4S$ ([M-H]$^-$): 260.5, found: 260.5.

Step 4: N-(3-(5-(4-Chlorophenyl)-1H-pyrrolo[2,3-b]pyridine-3-carbonyl)-2-fluorophenyl)propane-1-sulfonamide Procedure: The title compound was obtained by following GP af.
Yield: 84 mg, 178 μmol, 68% (white solid).
TLC: DCM/MeOH 5%
$^1$H NMR (DMSO-d$_6$ 400 MHz, ppm): δ 12.88 (s, 1H), 9.79 (s, 1H), 8.69 (d, J=2.2 Hz, 1H), 8.66 (d, J=2.1 Hz, 1H), 8.05 (s, 1H), 7.77 (d, J=8.5 Hz, 2H), 7.60 (td, J=7.9, 1.5 Hz, 1H), 7.56 (d, J=8.5 Hz, 2H), 7.47-7.41 (m, 1H), 7.33 (t, J=7.8 Hz, 1H), 3.15 (dd, J=8.6, 6.7 Hz, 2H), 1.83-1.69 (m, 2H), 0.97 (t, J=7.4 Hz, 3H). $^{13}$C NMR (DMSO-d$_6$, 101 Hz, ppm): δ 185.5, 152.0 (d, J=249.8 Hz), 148.8, 143.6, 137.8, 137.1, 132.4, 129.9, 129.0, 128.9, 128.8, 127.8, 127.2, 126.1 (d, J=2.0 Hz), 125.8 (d, J=13.1 Hz), 124.6 (d, J=4.0 Hz), 117.9, 114.9, 53.8, 16.8, 12.5. TLC-MS: m/z calculated for $C_{23}H_{19}ClFN_3O_3S$ ([M-H]$^-$): 470.1, found: 470.1.

Example 28

N-(3-(5-(4-Chlorophenyl)-1H-pyrrolo[2,3-b]pyridine-3-carbonyl)-4-fluorophenyl)propane-1-sulfonamide

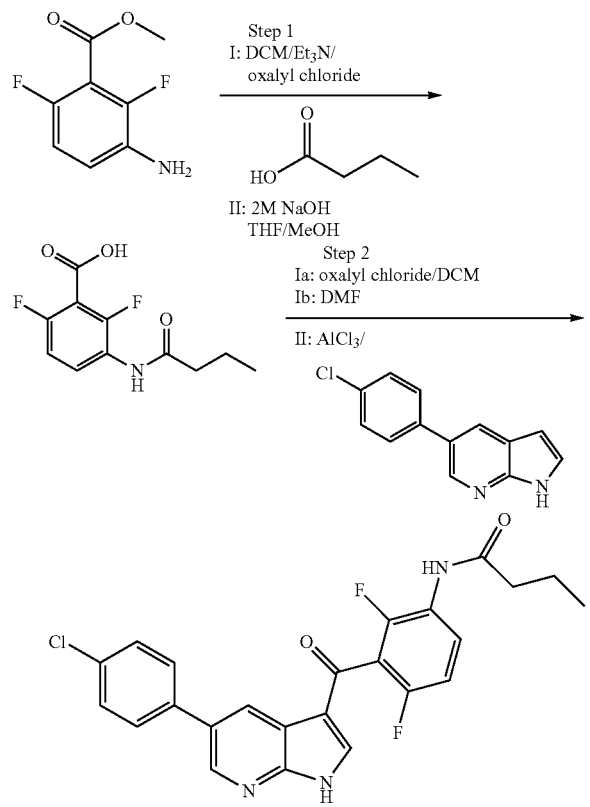

Step 1: 3-Butyramido-2,6-difluorobenzoic acid

Procedure: The title compound was obtained by following GP ac using butyric acid (1.1 eq.), oxalyl chloride (1.05 eq.) and DMF (cat.) to synthesize butyryl chloride in situ.

Yield: 646 mg, 2.7 mmol, 85% over 2 steps (beige solid).
TLC: PE/EtOAc 25%
$^1$H NMR (DMSO-d$_6$ 200 MHz, ppm): δ 13.87 (s, 1H), 9.75 (s, 1H), 7.87 (td, J=8.9, 6.1 Hz, 1H), 7.15 (td, J=9.2, 1.6 Hz, 1H), 2.33 (t, J=7.2 Hz, 2H), 1.72-1.49 (m, 2H), 0.91 (t, J=7.4 Hz, 3H). $^{13}$C NMR (DMSO-d$_6$, 50 Hz, ppm): δ 172.1, 162.4, 156.0 (dd, J=203.4, 6.6 Hz), 151.0 (dd, J=207.5, 6.6 Hz), 127.7 (dd, J=10.2, 3.2 Hz), 123.5 (dd, J=12.4, 3.8 Hz), 112.7 (dd, J=21.3, 18.9 Hz), 111.9 (dd, J=22.3, 3.9 Hz), 37.9, 18.9, 13.9.

Step 2: N-(3-(5-(4-Chlorophenyl)-1H-pyrrolo[2,3-b]pyridine-3-carbonyl)-2,4-difluorophenyl)butyramide Procedure: The title compound was obtained by following GP ae.
Yield: 46 mg, 100 μmol, 38% (white solid).
TLC: DCM/MeOH 5%
$^1$H NMR (DMSO-d$_6$ 400 MHz, ppm): δ 13.01 (s, 1H), 9.80 (s, 1H), 8.71 (d, J=1.7 Hz, 1H), 8.65 (s, 1H), 8.21 (s, 1H), 7.99 (dd, J=14.8, 8.6 Hz, 1H), 7.79 (d, J=8.4 Hz, 2H), 7.56 (d, J=8.4 Hz, 2H), 7.23 (t, J=8.7 Hz, 1H), 2.36 (t, J=7.2 Hz, 2H), 1.67-1.55 (m, 2H), 0.91 (t, J=7.3 Hz, 3H). $^{13}$C NMR (DMSO-d$_6$, 101 Hz, ppm): δ 180.9, 171.6, 154.61 (dd, J=244.8, 5.5 Hz), 150.4 (dd, J=249.4, 6.5 Hz), 148.9, 143.8, 138.6, 137.0, 132.5, 130.2, 129.0, 128.9, 127.1, 126.1 (dd, J=6.4, 2.6 Hz), 123.2 (dd, J=12.4, 3.4 Hz), 117.7 (dd, J=19.8, 17.6 Hz), 117.5, 115.7, 111.5 (dd, J=22.1, 2.6 Hz), 37.5, 18.5, 13.5. TLC-MS: m/z calculated for $C_{24}H_{18}ClF_2N_3O_2$ ([M-H]$^-$): 452.1, found: 452.1.

Example 29

N-(3-(5-(4-Chlorophenyl)-1H-pyrrolo[2,3-b]pyridine-3-carbonyl)-4-fluorophenyl)propane-1-sulfonamide

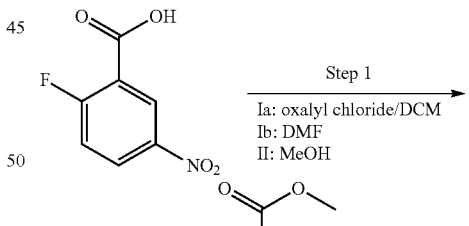

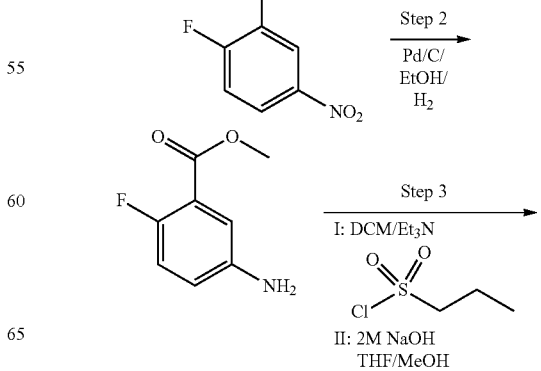

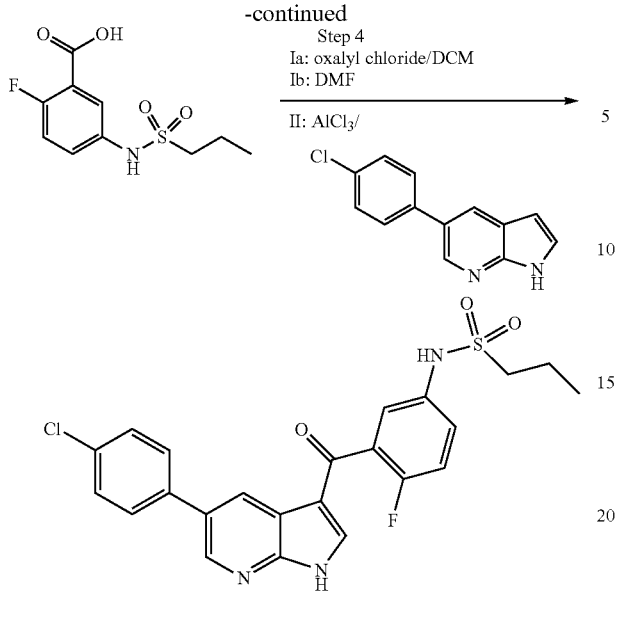

Step 1: Methyl 2-fluoro-5-nitrobenzoate

Procedure: The title compound was obtained by following GP aa.

Yield: 1.1 g, 5.4 mmol, 99% (pale yellow solid).
TLC: PE/EtOAc 25%
$^1$H NMR (DMSO-$d_6$, 200 MHz, ppm): δ 8.63-8.57 (m, 1H), 8.57-8.47 (m, 1H), 7.73-7.59 (m, 1H), 3.91 (s, 3H). $^{13}$C NMR (DMSO-$d_6$, 50 Hz, ppm): δ 164.2 (d, J=267.8 Hz), 162.2 (d, J=4.0 Hz), 143.7 (d, J=3.3 Hz), 130.3 (d, J=11.6 Hz), 127.4 (d, J=3.2 Hz), 119.2 (d, J=12.5 Hz), 119.1 (d, J=25.0 Hz), 53.0.

Step 2: Methyl 5-amino-2-fluorobenzoate

Procedure: The title compound was obtained by following GP ab.

Yield: 0.9 g, 5.3 mmol, 99% (brown oil).
TLC: PE/EtOAc 25%

Step 3: 2-Fluoro-5-(propylsulfonamido)benzoic acid

Procedure: The title compound was obtained by following GP ac.

Yield: 777 mg, 3.4 mmol, 55% over 2 steps (white solid).
TLC: PE/EtOAc 25%
$^1$H NMR (DMSO-$d_6$, 200 MHz, ppm): δ 13.38 (s, 1H), 9.94 (s, 1H), 7.70 (dd, J=6.2, 2.5 Hz, 1H), 7.49-7.37 (m, 1H), 7.28 (t, J=9.5 Hz, 1H), 3.12-2.96 (m, 2H), 1.78-1.54 (m, 2H), 0.92 (t, J=7.3 Hz, 3H). $^{13}$C NMR (DMSO-$d_6$, 50 Hz, ppm): δ 164.7 (d, J=3.4 Hz), 157.7 (d, J=253.8 Hz), 134.5 (d, J=3.1 Hz), 125.9 (d, J=9.0 Hz), 122.6, 119.8 (d, J=11.6 Hz), 118.0 (d, J=24.1 Hz), 52.4, 16.8, 12.5. TLC-MS: m/z calculated for $C_{10}H_{12}FNO_4S$ ([M-H]$^-$): 260.1, found: 260.1.

Step 4: N-(3-(5-(4-Chlorophenyl)-1H-pyrrolo[2,3-b]pyridine-3-carbonyl)-4-fluoro phenyl)propane-1-sulfonamide Procedure: The title compound was obtained by following GP af.
Yield: 88 mg, 186 μmol, 71% (white solid).
TLC: DCM/MeOH 5%
$^1$H NMR (DMSO-$d_6$ 400 MHz, ppm): δ 12.92 (d, J=1.5 Hz, 1H), 9.96 (s, 1H), 8.69 (s, 1H), 8.68 (s, 1H), 8.12 (s, 1H), 7.78 (d, J=8.5 Hz, 2H), 7.57 (d, J=8.4 Hz, 2H), 7.46-7.33 (m, 3H), 3.15-3.07 (m, 2H), 1.76-1.63 (m, 2H), 0.95 (t, J=7.4 Hz, 3H). $^{13}$C NMR (DMSO-$d_6$, 101 Hz, ppm): δ 185.5, 155.3 (d, J=245.2 Hz), 148.8, 143.6, 137.9, 137.1, 134.6, 132.4, 130.0, 129.0, 128.8, 128.5 (d, J=17.4 Hz), 127.3, 123.7 (d, J=8.1 Hz), 121.0 (d, J=3.1 Hz), 118.0, 117.3 (d, J=23.4 Hz), 114.8, 52.5, 16.8, 12.5. TLC-MS: m/z calculated for $C_{23}H_{19}ClFN_3O_3S$ ([M-H]$^-$): 470.1, found: 470.0.

Example 30

N-(3-(5-(4-Chlorophenyl)-1H-pyrrolo[2,3-b]pyridine-3-carbonyl)-2,4-difluorophenyl)hexane-1-sulfonamide

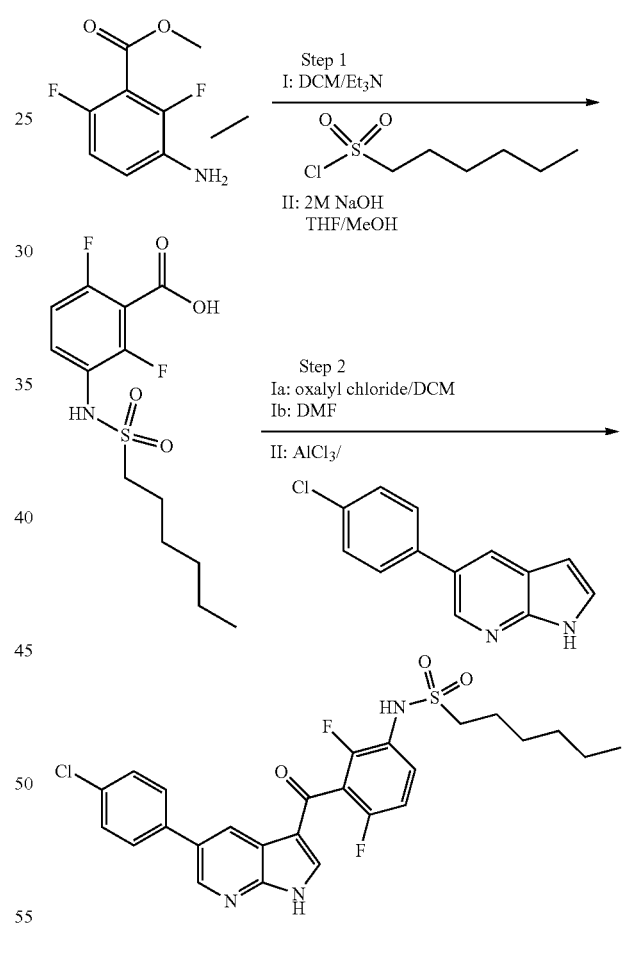

Step 1: 2,6-Difluoro-3-(hexylsulfonamido)benzoic acid

Procedure: The title compound was obtained by following GP ac.

Yield: 237 mg, 738 μmol, 70% over 2 steps (off white solid).

TLC: PE/EtOAc 25% TLC-MS: m/z calculated for $C_{12}H_{16}F_2NO_2S'$ ([M-CHO$_2$]$^{1-}$): 276.1, found: 275.9.

Step 2: N-(3-(5-(4-Chlorophenyl)-1H-pyrrolo[2,3-b]pyridine-3-carbonyl)-2,4-difluoro phenyl)hexane-1-sulfonamide Procedure: The title compound was obtained by following GP ae.

Yield: 88 mg, 165 µmol, 63% (white solid).

TLC: DCM/MeOH 5%

$^1$H NMR (DMSO-$d_6$ 400 MHz, ppm): δ 13.04 (s, 1H), 9.78 (s, 1H), 8.71 (d, J=2.1 Hz, 1H), 8.63 (s, 1H), 8.25 (d, J=1.8 Hz, 1H), 7.79 (d, J=8.4 Hz, 2H), 7.66-7.50 (m, 3H), 7.29 (t, J=8.7 Hz, 1H), 3.18-3.07 (m, 2H), 1.76-1.63 (m, 2H), 1.40-1.27 (m, 2H), 1.26-1.15 (m, 4H), 0.79 (t, J=6.7 Hz, 3H). $^{13}$C NMR (DMSO-$d_6$, 101 Hz, ppm): δ 180.6, 156.0 (dd, J=247.0, 6.9 Hz), 152.3 (dd, J=249.9, 8.3 Hz), 149.0, 143.9, 138.7, 137.0, 132.5, 130.2, 129.1, 128.9, 128.7 (m), 127.0, 121.9 (dd, J=13.8, 3.5 Hz), 118.1 (dd, J=36.3, 12.7 Hz), 117.5, 115.7, 112.3 (dd, J=22.8, 3.5 Hz), 51.9, 30.6, 27.0, 23.0, 21.7, 13.7. TLC-MS: m/z calculated for $C_{26}H_{24}ClF_2N_3O_3S$ ([M-H]$^-$): 530.1, found: 530.0.

Example 31

N-(3-(5-(4-Chlorophenyl)-1H-pyrrolo[2,3-b]pyridine-3-carbonyl)-2,4-difluorophenyl)-3-methylbutane-1-sulfonamide

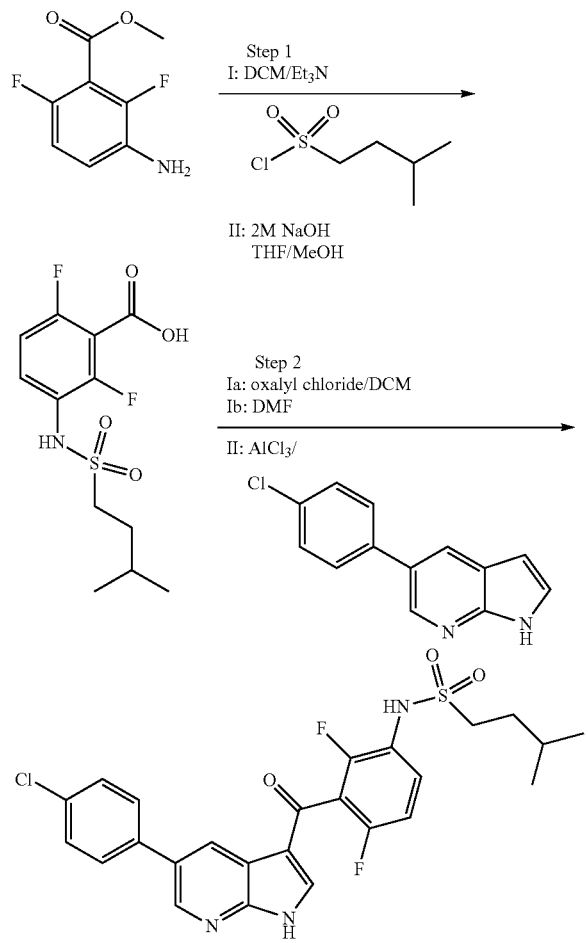

Step 1: 2,6-Difluoro-3-((3-methylbutyl)sulfonamido)benzoic acid

Procedure: The title compound was obtained by following GP ac.

Yield: 171 mg, 556 µmol, 53% over 2 steps (off white solid).

TLC: PE/EtOAc 25%

$^1$H NMR (DMSO-$d_6$, 400 MHz, ppm): δ 9.76 (s, 1H), 7.54 (td, J=8.9, 5.9 Hz, 1H), 7.20 (td, J=9.0, 0.9 Hz, 1H), 3.12-3.05 (m, 2H), 1.70-1.56 (m, 3H), 0.86 (d, J=6.2 Hz, 6H). $^{13}$C NMR (DMSO-$d_6$, 101 Hz, ppm): δ 161.7, 156.5 (dd, J=250.9, 6.1 Hz), 153.0 (dd, J=254.2, 7.5 Hz), 129.7 (d, J=10.1 Hz), 121.9 (dd, J=13.4, 3.6 Hz), 113.0-112.5 (m), 112.2 (dd, J=22.7, 3.8 Hz), 50.4, 31.7, 26.4, 21.9. TLC-MS: m/z calculated for $C_{12}H_{15}F_2NO_4S$ ([M-H]$^-$): 306.1, found: 306.0.

Step 2: N-(3-(5-(4-Chlorophenyl)-1H-pyrrolo[2,3-b]pyridine-3-carbonyl)-2,4-difluoro phenyl)-3-methylbutane-1-sulfonamide Procedure: The title compound was obtained by following GP ae.

Yield: 77 mg, 149 µmol, 57% (white solid).

TLC: DCM/MeOH 5%

$^1$H NMR (DMSO-$d_6$ 400 MHz, ppm): δ 13.03 (s, 1H), 9.79 (s, 1H), 8.71 (d, J=1.9 Hz, 1H), 8.64 (s, 1H), 8.26 (s, 1H), 7.79 (d, J=8.4 Hz, 2H), 7.67-7.47 (m, 3H), 7.29 (t, J=8.6 Hz, 1H), 3.23-3.02 (m, 2H), 1.69-1.51 (m, 3H), 0.83 (d, J=5.7 Hz, 6H). $^{13}$C NMR (DMSO-$d_6$, 101 Hz, ppm): δ 180.6, 156.0 (dd, J=246.6, 6.9 Hz), 152.3 (dd, J=249.2, 8.6 Hz), 149.0, 143.9, 138.8, 137.0, 132.5, 130.2, 129.0, 128.9, 128.7 (d, J=11.9 Hz), 127.0, 121.9 (dd, J=12.9, 3.1 Hz), 118.1 (dd, J=24.8, 23.0 Hz), 117.4, 115.7, 112.3 (dd, J=23.0, 3.1 Hz), 50.2, 31.6, 26.4, 21.9. TLC-MS: m/z calculated for $C_{25}H_{22}ClF_2N_3O_3S$ ([M-H]$^-$): 516.1, found: 516.0.

Example 32

N-(3-(5-(4-Chlorophenyl)-1H-pyrrolo[2,3-b]pyridine-3-carbonyl)-2,4-difluorophenyl)-2-methoxyethane-1-sulfonamide

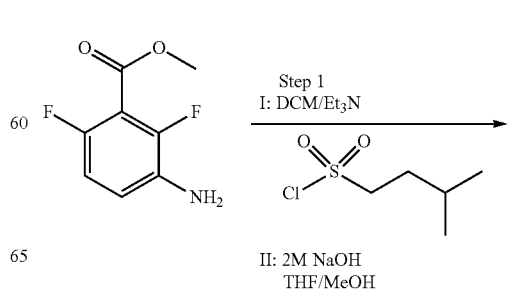

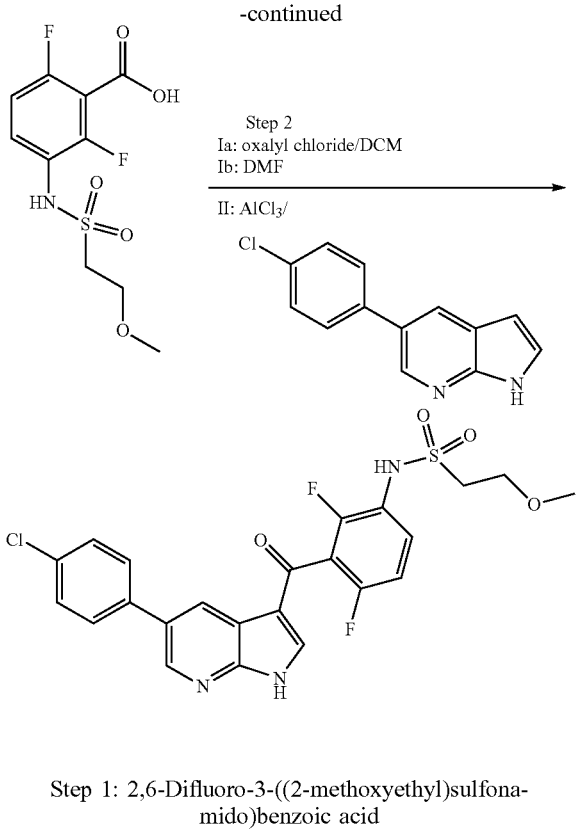

Step 1: 2,6-Difluoro-3-((2-methoxyethyl)sulfonamido)benzoic acid

Procedure: The titled compound was yielded by following GP ac.
Yield: 79 mg, 268 μmol, 25% over 2 steps (white solid).
TLC: PE/EtOAc 25%
$^1$H NMR (DMSO-d$_6$, 400 MHz, ppm): δ 9.78 (s, 1H), 7.55 (td, J=8.8, 6.0 Hz, 1H), 7.20 (t, J=9.0 Hz, 1H), 3.68 (t, J=6.0 Hz, 2H), 3.40 (t, J=6.0 Hz, 2H), 3.19 (s, 3H). $^{13}$C NMR (DMSO-d$_6$, 101 Hz, ppm): δ 161.8, 156.4 (dd, J=251.0, 6.2 Hz), 152.9 (dd, J=254.4, 7.5 Hz), 129.3 (dd, J=10.1, 1.8 Hz), 121.9 (dd, J=13.3, 3.7 Hz), 112.7 (dd, J=21.3, 19.4 Hz), 112.1 (dd, J=22.5, 3.9 Hz), 65.7, 57.9, 52.1. TLC-MS: m/z calculated for C$_{10}$H$_{11}$F$_2$NO$_5$S ([M-H]$^-$): 295.0, found: 295.0.

Step 2: N-(3-(5-(4-Chlorophenyl)-1H-pyrrolo[2,3-b]pyridine-3-carbonyl)-2,4-difluoro phenyl)-2-methoxyethane-1-sulfonamide Procedure: The title compound was obtained by following GP ae.
Yield: 59 mg, 117 μmol, 67% (white solid).
TLC: DCM/MeOH 5%
$^1$H NMR (DMSO-d$_6$ 400 MHz, ppm): δ 13.03 (s, 1H), 9.83 (s, 1H), 8.71 (d, J=2.2 Hz, 1H), 8.65 (s, 1H), 8.24 (s, 1H), 7.79 (d, J=8.5 Hz, 2H), 7.65-7.52 (m, 3H), 7.28 (t, J=8.7 Hz, 1H), 3.70 (t, J=6.1 Hz, 2H), 3.45 (t, J=6.1 Hz, 2H), 3.20 (s, 3H). $^{13}$C NMR (DMSO-d$_6$, 101 Hz, ppm): δ 180.6, 155.9 (dd, J=246.3, 7.1 Hz), 152.2 (dd, J=249.0, 7.7 Hz), 149.0, 144.0, 138.7, 137.0, 132.5, 130.2, 129.0, 128.9, 128.3 (d, J=8.7 Hz), 127.0, 121.9 (dd, J=13.5, 3.5 Hz), 118.1 (dd, J=24.2, 22.3 Hz), 117.5, 115.7, 112.2 (dd, J=22.6, 3.5 Hz), 65.7, 57.9, 51.8. TLC-MS: m/z calculated for C$_{23}$H$_{18}$ClF$_2$N$_3$O$_4$S ([M-H]$^-$): 504.1, found: 503.9.

Example 33

N-(3-(5-(4-Chlorophenyl)-1H-pyrrolo[2,3-b]pyridine-3-carbonyl)-2,4-difluorophenyl)pentane-1-sulfonamide

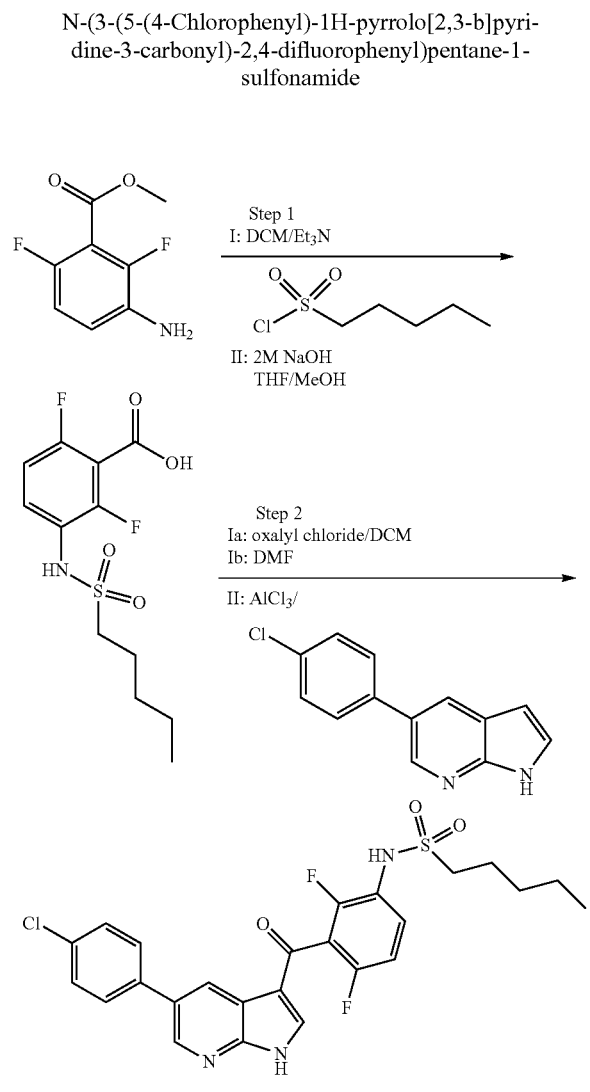

Step 1: 2,6-Difluoro-3-(pentylsulfonamido)benzoic acid

Procedure: The title compound was obtained by following GP ac.
Yield: 236 mg, 768 μmol, 73% over 2 steps (white solid).
TLC: PE/EtOAc 25%
TLC-MS: m/z calculated for C$_{12}$H$_{15}$F$_2$NO$_4$S ([M-H]$^-$): 306.1, found: 306.0.

Step 2: N-(3-(5-(4-Chlorophenyl)-1H-pyrrolo[2,3-b]pyridine-3-carbonyl)-2,4-difluorophenyl)pentane-1-sulfonamide Procedure: The title compound was obtained by following GP af.
Yield: 73 mg, 141 μmol, 54% (white solid).
TLC: DCM/MeOH 5%
$^1$H NMR (DMSO-d$_6$ 400 MHz, ppm): δ 13.03 (s, 1H), 9.78 (s, 1H), 8.71 (d, J=1.8 Hz, 1H), 8.63 (s, 1H), 8.25 (s, 1H), 7.79 (d, J=8.4 Hz, 2H), 7.62-7.55 (m, 3H), 7.29 (t, J=8.7 Hz, 1H), 3.17-3.09 (m, 2H), 1.71 (dt, J=15.1, 7.5 Hz, 2H), 1.40-1.20 (m, 4H), 0.81 (t, J=7.1 Hz, 3H). $^{13}$C NMR (DMSO-d$_6$, 101 Hz, ppm): δ 180.6, 156.0 (dd, J=246.6, 6.8 Hz), 152.3 (dd, J=249.6, 8.4 Hz), 149.0, 143.9, 138.7, 137.0, 132.5, 130.2, 129.0, 128.9, 128.9-128.5 (m), 127.0, 121.9 (dd, J=13.6, 3.4 Hz), 118.5-117.8 (m), 117.5, 115.7, 112.3 (dd, J=22.9, 3.5 Hz), 51.8, 29.5, 22.7, 21.5, 13.5. TLC-MS: m/z calculated for C$_{25}$H$_{22}$ClF$_2$N$_3$O$_3$S ([M-H]$^-$): 516.1, found: 516.2.

Example 34

N-(3-(5-(Benzo[d][1,3]dioxol-5-yl)-1H-pyrrolo[2,3-b]pyridine-3-carbonyl)-2,4-difluorophenyl)methanesulfonamide

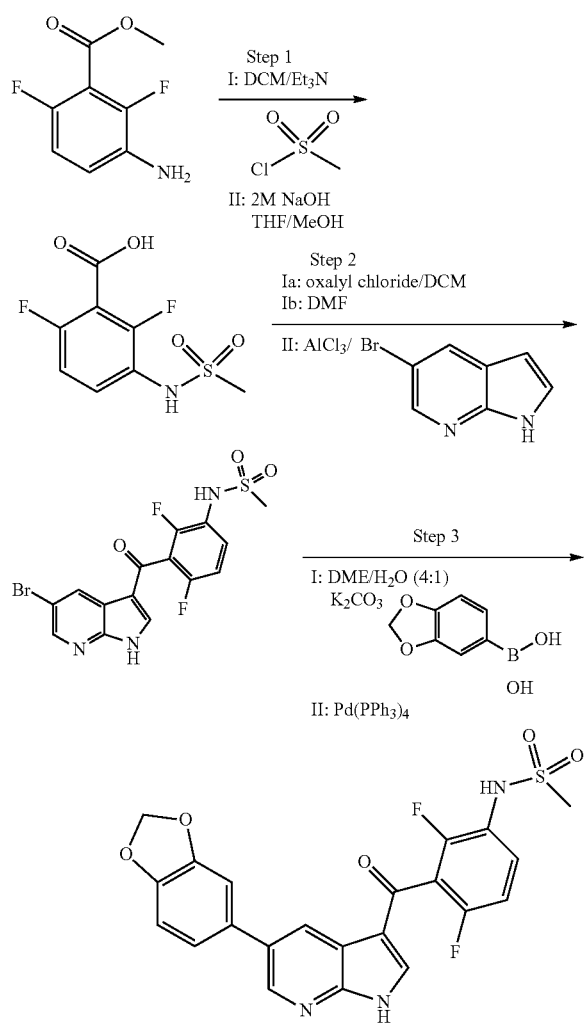

Step 1: 2-Fluoro-3-(methylsulfonamido)benzoic acid

Procedure: The title compound was obtained by following GP ac.

Yield: 1.82 g, 7.8 mmol, 72% over 2 steps (white solid).

TLC: PE/EtOAc 25%

$^1$H NMR (DMSO-d$_6$, 200 MHz, ppm): δ 13.36 (s, 1H), 9.76 (s, 1H), 7.65 (ddd, J=15.0, 8.2, 1.2 Hz, 2H), 7.27 (t, J=8.0 Hz, 1H), 3.05 (s, 3H). $^{13}$C NMR (DMSO-d$_6$, 50 Hz, ppm): δ 164.8 (d, J=2.8 Hz), 154.7 (d, J=259.4 Hz), 130.5, 128.6, 126.3 (d, J=13.4 Hz), 124.4 (d, J=4.8 Hz), 120.4 (d, J=9.5 Hz), 40.5 (d, J=1.0 Hz). TLC-MS: m/z calculated for C$_8$H$_8$FNO$_4$S ([M-H]$^-$): 232.0, found: 231.9.

Step 2: N-(3-(5-Bromo-1H-pyrrolo[2,3-b]pyridine-3-carbonyl)-2-fluorophenyl) methanesulfonamide Procedure: The title compound was obtained by following GP ae.

Yield: 1.19 g, 2.9 mmol, 82% (white solid).

TLC: DCM/MeOH 5%

$^1$H NMR (DMSO-d$_6$, 200 MHz, ppm): δ 12.98 (s, 1H), 9.77 (s, 1H), 8.61 (d, J=2.1 Hz, 1H), 8.47 (d, J=2.1 Hz, 1H), 8.09 (s, 1H), 7.60 (dd, J=7.9, 6.4 Hz, 1H), 7.51-7.25 (m, 2H), 3.10 (s, 3H). $^{13}$C NMR (DMSO-d$_6$, 50 Hz, ppm): δ 185.5, 152.2 (d, J=250.5 Hz), 147.6, 145.0, 138.5 (d, J=1.5 Hz), 131.3, 128.7 (d, J=15.1 Hz), 128.1, 126.4 (d, J=2.7 Hz), 125.8 (d, J=13.4 Hz), 124.7 (d, J=4.3 Hz), 119.6, 114.2, 114.0. TLC-MS: m/z calculated for C$_{15}$H$_{11}$BrFN$_3$O$_3$S ([M-H]$^-$): 410.0, found: 409.9.

Step 3: N-(3-(5-(Benzo[d][1,3]dioxol-5-yl)-1H-pyrrolo[2,3-b]pyridine-3-carbonyl)-2-fluorophenyl)methanesulfonamide Procedure: The title compound was obtained by following GP ad.

Yield: 42 mg, 93 μmol, 45% (white solid).

TLC: DCM/MeOH 5%

$^1$H NMR (DMSO-d$_6$ 400 MHz, ppm): δ 12.81 (s, 1H), 9.79 (s, 1H), 8.61 (d, J=2.0 Hz, 1H), 8.58 (d, J=1.9 Hz, 1H), 8.02 (s, 1H), 7.59 (t, J=7.2 Hz, 1H), 7.44 (t, J=6.1 Hz, 1H), 7.34 (t, J=7.8 Hz, 1H), 7.30 (d, J=1.3 Hz, 1H), 7.18 (dd, J=8.0, 1.5 Hz, 1H), 7.04 (d, J=8.0 Hz, 1H), 6.08 (s, 2H), 3.09 (s, 3H). TLC-MS: m/z calculated for C$_{22}$H$_{16}$FN$_3$O$_5$S ([M-H]$^-$): 452.1, found: 452.1.

Example 35

N-(3-(5-(4-Chlorophenyl)-1H-pyrrolo[2,3-b]pyridine-3-carbonyl)-2-fluoro phenyl)methanesulfonamide

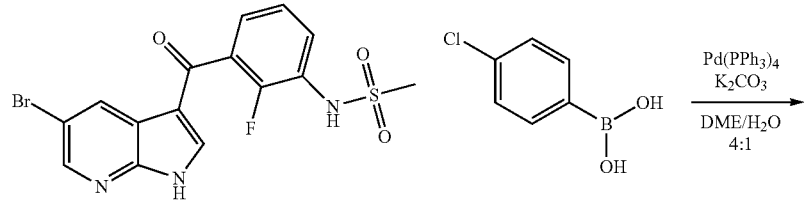

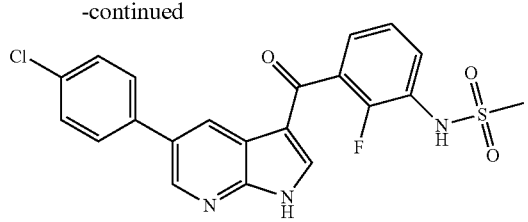

Procedure: The title compound was yielded by following GP ad.

Yield: 27 mg, 61 μmol, 31% (white solid).

TLC: DCM/MeOH 5%

$^1$H NMR (DMSO-d$_6$ 400 MHz, ppm): δ 12.88 (s, 1H), 9.79 (s, 1H), 8.68 (dd, J=7.3, 2.2 Hz, 2H), 8.06 (d, J=1.6 Hz, 1H), 7.77 (d, J=8.6 Hz, 2H), 7.63-7.53 (m, 3H), 7.49-7.41 (m, 1H), 7.34 (t, J=7.8 Hz, 1H), 3.10 (s, 3H). TLC-MS: m/z calculated for C$_{21}$H$_{15}$ClFN$_3$O$_3$S ([M-H]$^-$): 442.1, found: 442.0.

Example 36

N-(3-(5-(2,3-Dihydrobenzo[b][1,4]dioxin-6-yl)-1H-pyrrolo[2,3-b]pyridine-3-carbonyl)-2-fluorophenyl)methanesulfonamide

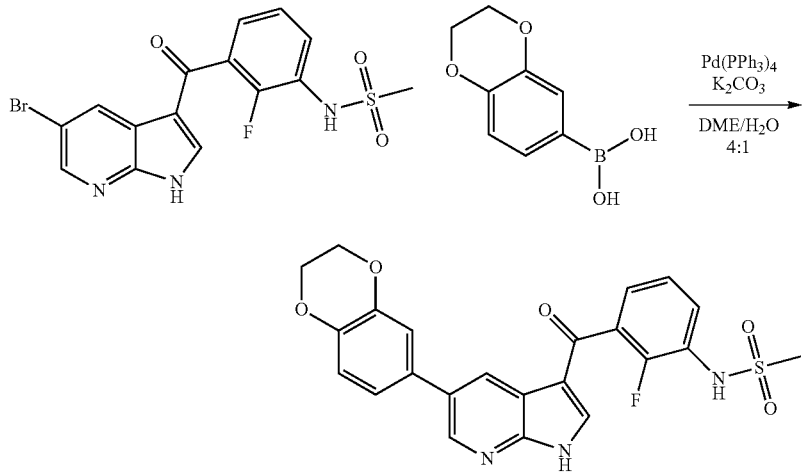

Procedure: The title compound was obtained by following GP ad.

Yield: 39 mg, 83 μmol, 43% (white solid).

TLC: DCM/MeOH 5%

$^1$H NMR (DMSO-d$_6$ 400 MHz, ppm): δ 12.80 (s, 1H), 9.79 (s, 1H), 8.60 (d, J=2.2 Hz, 1H), 8.56 (d, J=2.2 Hz, 1H), 8.01 (s, 1H), 7.59 (td, J=7.8, 1.5 Hz, 1H), 7.46-7.41 (m, 1H), 7.34 (t, J=7.8 Hz, 1H), 7.22-7.13 (m, 2H), 6.98 (d, J=8.2 Hz, 1H), 4.29 (s, 4H), 3.09 (s, 3H).

TLC-MS: m/z calculated for C$_{23}$H$_{18}$FN$_3$O$_5$S ([M-H]$^-$): 466.1, found: 466.1.

Example 37

N-(2-Fluoro-3-(5-(4-fluoro-2-methylphenyl)-1H-pyrrolo[2,3-b]pyridine-3-carbonyl)phenyl)methanesulfonamide

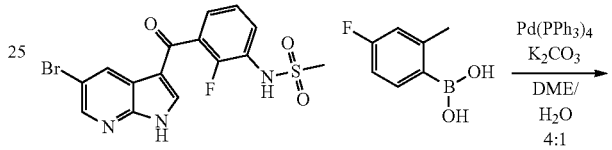

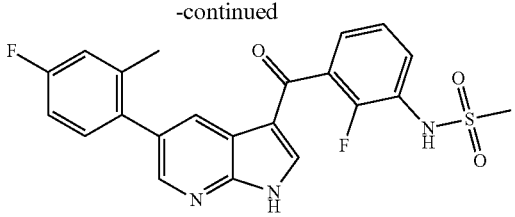

Procedure: The title compound was obtained by following GP ad.

Yield: 41 mg, 93 μmol, 48% (white solid).

TLC: DCM/MeOH 5%

¹H NMR (DMSO-d₆ 400 MHz, ppm): δ 12.87 (s, 1H), 9.78 (s, 1H), 8.36 (d, J=2.1 Hz, 1H), 8.34 (d, J=2.1 Hz, 1H), 8.06 (d, J=1.4 Hz, 1H), 7.59 (td, J=7.8, 1.6 Hz, 1H), 7.47-7.41 (m, 1H), 7.34 (dd, J=8.3, 6.1 Hz, 2H), 7.22 (dd, J=10.1, 2.5 Hz, 1H), 7.13 (td, J=8.5, 2.6 Hz, 1H), 3.09 (s, 3H), 2.26 (s, 3H). TLC-MS: m/z calculated for $C_{22}H_{17}F_2N_3O_3S$ ([M-H]⁻): 440.1, found: 440.1.

Example 38

N-(3-(5-(2-Chlorophenyl)-1H-pyrrolo[2,3-b]pyridine-3-carbonyl)-2-fluorophenyl) methanesulfonamide

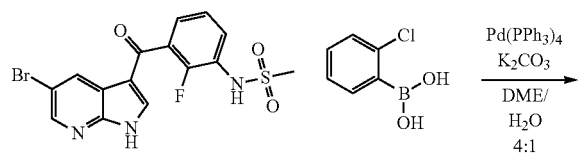

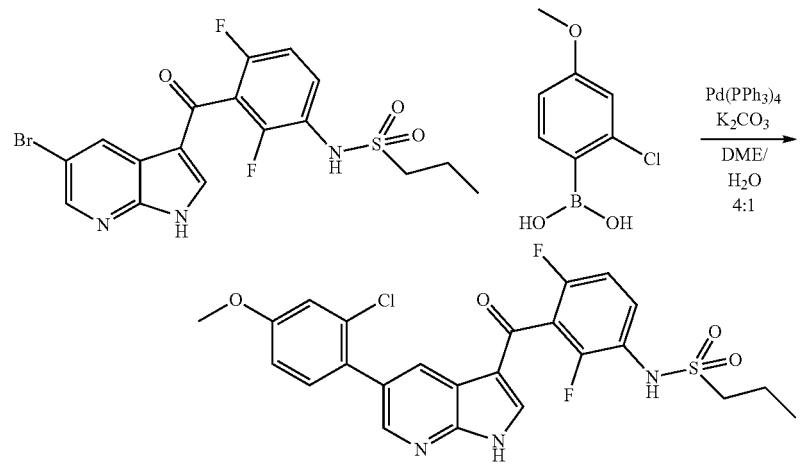

Procedure: The title compound was obtained by following GP ad.
Yield: 32 mg, 72 μmol, 46% (white solid).
TLC: DCM/MeOH 5%
¹H NMR (DMSO-d₆ 400 MHz, ppm): δ 12.93 (s, 1H), 9.79 (s, 1H), 8.52 (d, J=2.0 Hz, 1H), 8.44 (d, J=2.1 Hz, 1H), 8.10 (s, 1H), 7.66-7.42 (m, 6H), 7.34 (t, J=7.8 Hz, 1H), 3.09 (s, 3H). TLC-MS: m/z calculated for $C_{21}H_{15}ClFN_3O_3S$ ([M-H]⁻): 442.1, found: 442.1.

Example 39

N-(3-(5-(2-Chloro-4-methoxyphenyl)-1H-pyrrolo[2,3-b]pyridine-3-carbonyl)-2,4-difluorophenyl)propane-1-sulfonamide Procedure: The title compound was obtained by following GP ad.
Yield: 53 mg, 102 μmol, 59% (white solid).
TLC: DCM/MeOH 5%
¹H NMR (DMSO-d₆, 300 MHz, ppm): δ 13.03 (d, J=1.7 Hz, 1H), 9.77 (s, 1H), 8.44 (s, 1H), 8.41 (d, J=2.0 Hz, 1H), 8.25 (d, J=2.1 Hz, 1H), 7.58 (td, J=9.0, 6.0 Hz, 1H), 7.47 (d, J=8.5 Hz, 1H), 7.28 (t, J=8.4 Hz, 1H), 7.21 (d, J=2.5 Hz, 1H), 7.06 (dd, J=8.6, 2.5 Hz, 1H), 3.85 (s, 3H), 3.18-3.06 (m, 2H), 1.82-1.66 (m, 2H), 0.96 (t, J=7.4 Hz, 3H). TLC-MS: m/z calculated for $C_{24}H_{20}ClF_2N_3O_4S$ ([M-H]⁻): 518.1, found: 518.1.

Example 40

N-(3-(5-(2-Chloro-4-fluorophenyl)-1H-pyrrolo[2,3-b]pyridine-3-carbonyl)-2,4-difluorophenyl)propane-1-sulfonamide

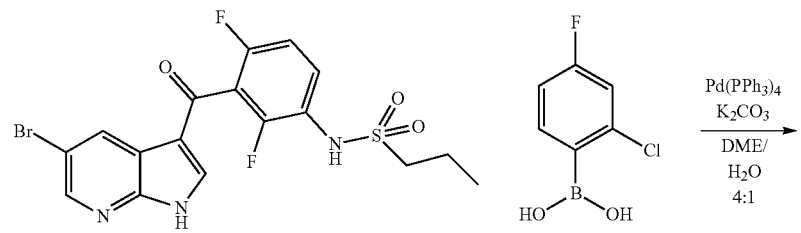

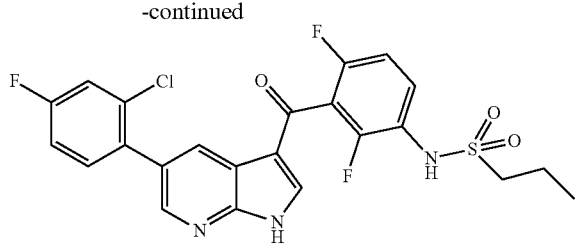

Procedure: The titled compound was yielded by following GP ad.

Yield: 36 mg, 71 μmol, 41% (white solid).

TLC: DCM/MeOH 5%

$^1$H NMR (DMSO-$d_6$ 300 MHz, ppm): δ 13.07 (s, 1H), 9.77 (s, 1H), 8.47 (s, 1H), 8.43 (d, J=2.1 Hz, 1H), 8.27 (s, 1H), 7.67-7.52 (m, 3H), 7.37 (td, J=8.5, 2.6 Hz, 1H), 7.28 (td, J=8.9, 1.3 Hz, 1H), 3.18-2.93 (m, 2H), 1.83-1.64 (m, 2H), 0.96 (t, J=7.4 Hz, 3H). TLC-MS: m/z calculated for $C_{23}H_{17}ClF_3N_3O_3S$ ([M-H]$^-$): 506.1, found: 505.9.

Example 41

N-(3-(5-(2,4-Dichlorophenyl)-1H-pyrrolo[2,3-b]pyridine-3-carbonyl)-2,4-difluorophenyl)propane-1-sulfonamide

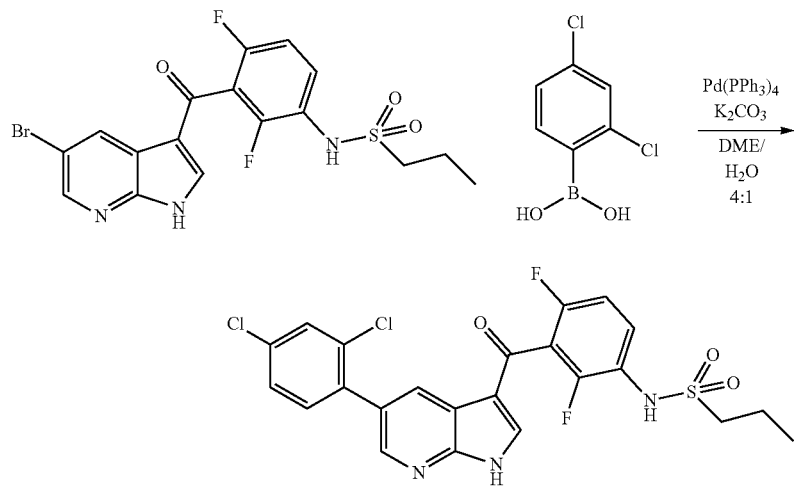

Procedure: The title compound was obtained by following GP ad.

Yield: 25 mg, 48 μmol, 27% (white solid).

TLC: DCM/MeOH 5%

$^1$H NMR (DMSO-$d_6$ 300 MHz, ppm): δ 13.08 (s, 1H), 9.77 (s, 1H), 8.48 (s, 1H), 8.45 (d, J=1.9 Hz, 1H), 8.28 (s, 1H), 7.80 (d, J=1.2 Hz, 1H), 7.59 (m, 3H), 7.28 (t, J=8.4 Hz, 1H), 3.18-3.04 (m, 2H), 1.81-1.65 (m, 2H), 0.96 (t, J=7.4 Hz, 3H). TLC-MS: m/z calculated for $C_{23}H_{17}Cl_2F_2N_3O_3S$ ([M-H]$^-$): 522.0, found: 521.9.

Example 42

N-(3-(5-(4-Chlorophenyl)-1H-pyrrolo[2,3-b]pyridine-3-carbonyl)-4-methylphenyl)propane-1-sulfonamide

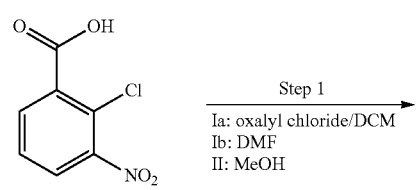

Step 1
Ia: oxalyl chloride/DCM
Ib: DMF
II: MeOH

-continued

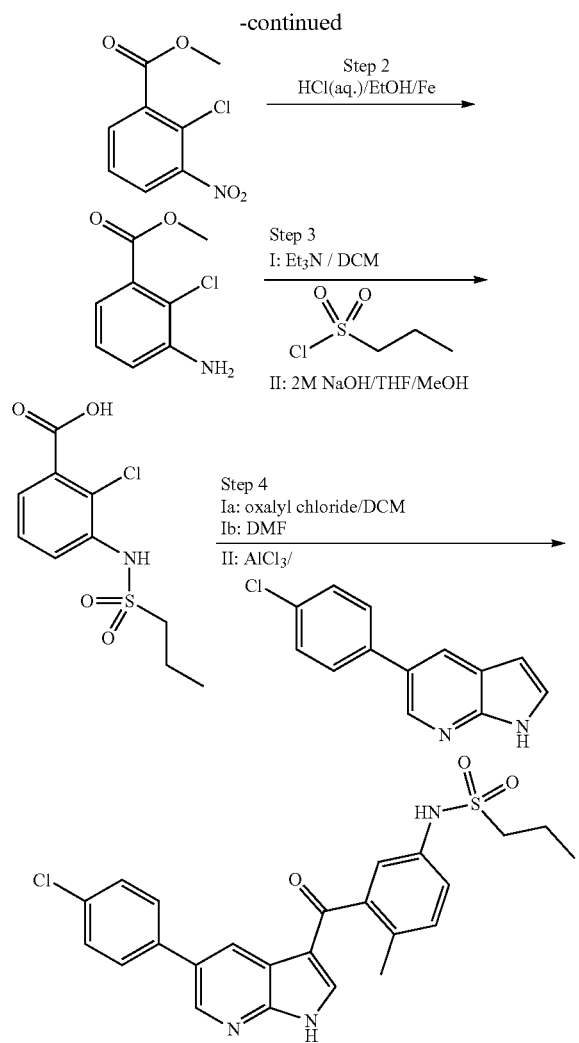

Step 1: Methyl 2-chloro-3-nitrobenzoate

Procedure: The title compound was obtained by following GP aa.
Yield: 1.06 g, 4.9 mmol, quantitative (pale yellow solid).
TLC: PE/EtOAc 25%
$^1$H NMR (DMSO-d$_6$, 200 MHz, ppm): δ 8.21 (dd, J=8.0, 1.5 Hz, 1H), 8.06 (dd, J=7.8, 1.5 Hz, 1H), 7.71 (t, J=7.9 Hz, 1H), 3.91 (s, 3H). $^{13}$C NMR (DMSO-d$_6$, 50 Hz, ppm): δ 164.4, 149.4, 133.7, 132.7, 128.9, 127.6, 123.0, 53.1.

Step 2: Methyl 3-amino-2-chlorobenzoate

Procedure: The ester (1.06 g, 4.9 mmol, 1 eq.) and HCl$^{aq}$. (1 m, 4.9 mL, 1 eq.) were dissolved in EtOH (0.25 m) and heated to reflux. Fine powdered iron (302 mg, 5.4 mmol, 1.1 eq.) was added in portions to the hot solution and the resulting mixture was refluxed until complete consumption of the starting material. The crude mixture was passed through a Celite pad, diluted with EtOAc and the organic layer was washed with water and brine. The combined organic layers were dried over Na$_2$SO$_4$, the solvent was removed under reduced pressure and the product was used without further purification.
Yield: 1.06 g, 4.8 mmol, 98% (brown oil).
TLC: PE/EtOAc 25%

Step 3: 2-Chloro-3-(propylsulfonamido)benzoic acid

Procedure: The title compound was obtained by following GP ac.
Yield: 402 mg, 1.5 mmol, 61% over 2 steps (off white solid).
TLC: PE/EtOAc 25%
$^1$H NMR (DMSO-d$_6$ 200 MHz, ppm): δ 13.50 (s, 1H), 9.58 (s, 1H), 7.64-7.52 (m, 2H), 7.40 (t, J=7.8 Hz, 1H), 3.20-3.03 (m, 2H), 1.87-1.63 (m, 2H), 0.97 (t, J=7.4 Hz, 3H). $^{13}$C NMR (DMSO-d$_6$, 50 Hz, ppm): δ 166.9, 135.3, 133.7, 129.3, 127.5, 127.2, 126.5, 54.7, 16.9, 12.7. TLC-MS: m/z calculated for C$_{10}$H$_{12}$ClNO$_4$S ([M-H]$^-$): 276.0, found: 275.9.

Step 4: N-(2-Chloro-3-(5-(4-chlorophenyl)-1H-pyrrolo[2,3-b]pyridine-3-carbonyl) phenyl)propane-1-sulfonamide Procedure: The title compound was obtained by following GP af.
Yield: 59 mg, 121 μmol, 46% (white solid).
TLC: DCM/MeOH 5%
$^1$H NMR (DMSO-d$_6$, 300 MHz, ppm): δ 12.88 (s, 1H), 9.61 (s, 1H), 8.69 (d, J=2.2 Hz, 1H), 8.53 (s, 1H), 7.95 (s, 1H), 7.76 (d, J=8.5 Hz, 2H), 7.63 (dd, J=8.0, 1.6 Hz, 1H), 7.55 (d, J=8.5 Hz, 2H), 7.49 (t, J=7.8 Hz, 1H), 7.40 (dd, J=7.5, 1.5 Hz, 1H), 3.16 (dd, J=8.7, 6.6 Hz, 2H), 1.85-1.68 (m, 2H), 0.97 (t, J=7.4 Hz, 3H). TLC-MS: m/z calculated for C$_{23}$H$_{19}$Cl$_2$N$_3$O$_3$S ([M-H]$^-$): 486.1, found: 486.1.

Example 43

N-(3-(5-(6-Chlorobenzo[d][1,3]dioxol-5-yl)-1H-pyrrolo[2,3-b]pyridine-3-carbonyl)-2,4-difluorophenyl)propane-1-sulfonamide

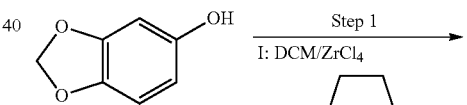

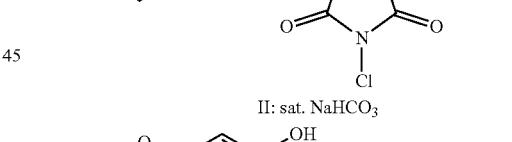

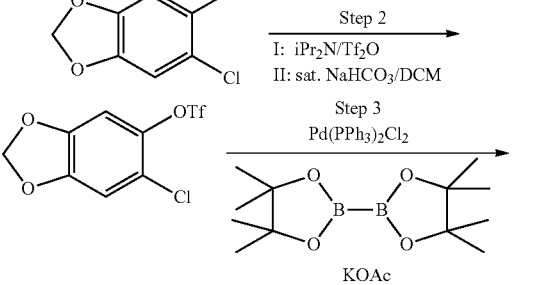

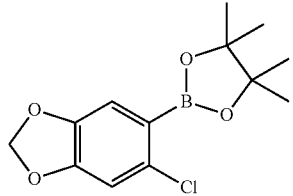

Step 4

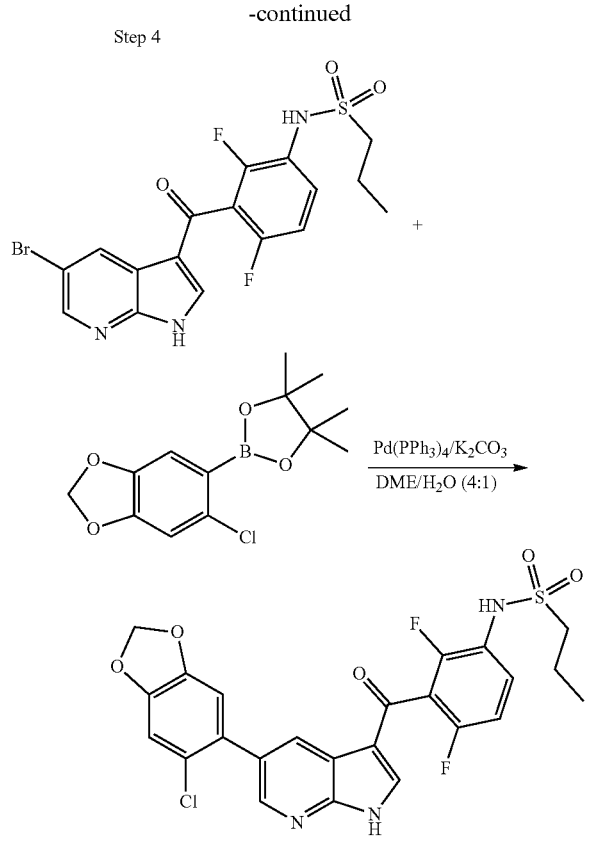

Step 1: 6-Chlorobenzo[d][1,3]dioxol-5-ol

Procedure: To a −78° C. cooled solution of N-chlorosuccinimide (967 mg, 7.2 mmol, 1 eq.) in DCM (0.125 m) was added ZrCl₄ (337 mg, 1.5 mmol, 0.2 eq.) and sesamol (1.0 g, 7.2 mmol, 1 eq.), successively. The reaction mixture was stirred at room temperature for 130 min and was quenched with saturated, aqueous NaHCO₃ solution. The crude was extracted with DCM, the combined organic layers were washed with brine and dried over Na₂SO₄. Then, the solvent was removed under reduced pressure and the product was purified via flash chromatography (SiO₂, nHex/EtOAc 10%).

Yield: 998 mg, 5.8 mmol, 80% (white solid).
TLC: PE/EtOAc 25%
¹H NMR (CDCl₃, 200 MHz, ppm): δ 6.77 (s, 1H), 6.57 (s, 1H), 5.92 (s, 2H), 5.22 (s, 1H). ¹³C NMR (CDCl₃, 50 Hz, ppm): δ 147.6, 146.5, 141.7, 110.3, 108.4, 101.8, 98.3. TLC-MS: m/z calculated for C₇H₅ClO₃ ([M-H]⁻): 171.0, found: 171.0.

Step 2: 6-Chlorobenzo[d][1,3]dioxol-5-yl trifluoromethanesulfonate

Procedure: A solution of 6-chlorobenzo[d][1,3]dioxol-5-ol (960 mg, 5.6 mmol, 1 eq.) in DCM (0.57 m) was cooled to 0° C. followed by the addition of iPr₂NH (782 µl, 5.6 mmol, 1 eq.) and Tf₂O (1.0 ml, 6.1 mmol, 1.1 eq.). The mixture was stirred at room temperature until complete consumption of the starting material was observed. Aqueous NaHCO₃ solution (5%) was used to quench the reaction, the resulting phases were separated and the aqueous phase was extracted with DCM. The combined organic layers were dried over Na₂SO₄ and the solvent was evaporated in vacuo. Flash chromatography (SiO₂, nHex/EtOAc 5%) yielded the purified product.

Yield: 1.1 g, 3.7 mmol, 67% (pale yellow oil).
TLC: PE/EtOAc 10%
¹H NMR (CDCl₃, 200 MHz, ppm): δ 6.92 (s, 1H), 6.82 (s, 1H), 6.07 (s, 2H).

Step 3: 2-(6-Chlorobenzo[d][1,3]dioxol-5-yl)-4,4,5,5-tetramethyl-1,3,2-dioxaborolane Procedure: Pd(PPh₃)₂Cl₂ (127 mg, 181 µmol, 0.05 eq.), B₂Pin₂ (1.4 g, 5.42 mmol, 1.5 eq.), KOAc (1.1 g, 10.8 mmol, 3 eq.) and 6-chlorobenzo[d][1,3]dioxol-5-yl trifluoromethanesulfonate (1.1 g, 3.6 mmol, 1 eq.) were placed in an oven dried flask under argon atmosphere. Dry 1,4-dioxane (0.5 m) was added and the mixture was degassed with argon. The reaction mixture was heated to 100° C. overnight and then passed through a Celite pad, which was washed with EtOAc. Flash chromatography (SiO₂, nHex/EtOAc 5%) yielded the purified product.

Yield: 887 mg, 3.1 mmol, 87% (white solid).
TLC: PE/EtOAc 10%
¹H NMR (CDCl₃, 200 MHz, ppm): δ 7.11 (s, 1H), 6.81 (s, 1H), 5.95 (s, 2H), 1.33 (s, 12H). ¹³C (CDCl₃, 50 Hz, ppm): δ 150.5, 146.3, 133.1, 114.9, 110.6, 101.8, 84.1, 83.6, 24.9.

Step 4: N-(3-(5-(6-Chlorobenzo[d][1,3]dioxol-5-yl)-1H-pyrrolo[2,3-b]pyridine-3-carbonyl)-2,4-difluorophenyl)propane-1-sulfonamide Procedure: The title compound was obtained by following GP ad.

Yield: 58 mg, 109 µmol, 50% (white solid).
TLC: DCM/MeOH 5%
¹H NMR (DMSO-d₆, 300 MHz, ppm): δ 13.03 (s, 1H), 9.77 (s, 1H), 8.43 (s, 1H), 8.39 (d, J=2.1 Hz, 1H), 8.25 (d, J=1.5 Hz, 1H), 7.59 (td, J=9.0, 5.9 Hz, 1H), 7.31-7.24 (m, 1H), 7.24 (s, 1H), 7.14 (s, 1H), 6.15 (s, 2H), 3.18-3.06 (m, 2H), 1.82-1.65 (m, 2H), 0.96 (t, J=7.4 Hz, 3H). TLC-MS: m/z calculated for C₂₄H₁₈ClF₂N₃O₅S ([M-H]⁻): 532.1, found: 532.2.

Example 44

N-(3-(5-(6-Chlorobenzo[d][1,3]dioxol-5-yl)-1H-pyrrolo[2,3-b]pyridine-3-carbonyl)-2,4-difluorophenyl)propane-1-sulfonamide

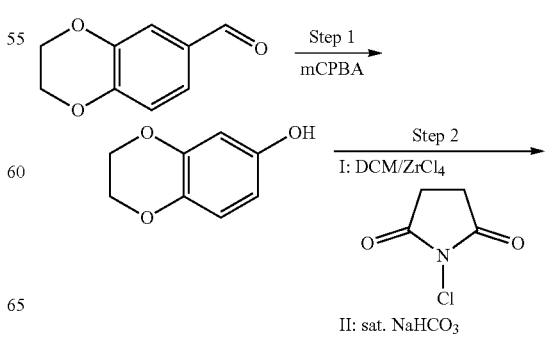

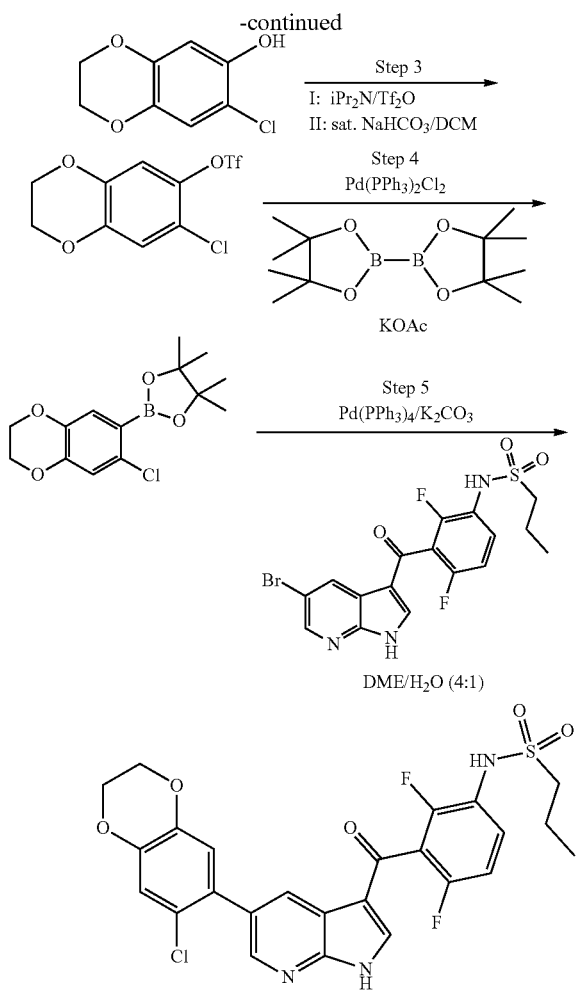

Step 1: 2,3-Dihydrobenzo[b][1,4]dioxin-6-ol

Procedure: 2,3-dihydrobenzo[b][1,4]dioxine-6-carbaldehyde (2 g, 12.2 mmol, 1 eq.) was placed in a mortar, mCPBA (4.5 g, 18.3 mmol, 1.5 eq.) was added and the solids were mixed with a pestle. The resulting paste left at room temperature for 5 min and then diluted with NaOH (10% in H$_2$O). The solution was washed with Et$_2$O, adjusted to pH 7 with HCl (2 m) and extracted with DCM. After the combined organic layers were dried over Na$_2$SO$_4$, the solvent was evaporated and the product was purified via flash chromatography (SiO$_2$, nHex/EtOAc/AcOH 79/20/1).

Yield: 1.7 g, 11.2 mmol, 92% (off white solid).
TLC: PE/EtOAc/AcOH 74/25/1
$^1$H NMR (CDCl$_3$, 200 MHz, ppm): δ 6.72 (dd, J=8.6, 0.4 Hz, 1H), 6.40 (dd, J=2.9, 0.4 Hz, 1H), 6.33 (dd, J=8.6, 2.9 Hz, 1H), 4.32-4.14 (m, 4H), 4.00 (s, 1H). $^{13}$C NMR (CDCl$_3$, 50 Hz, ppm): δ 150.1, 144.0, 137.7, 117.7, 108.5, 104.4, 64.7, 64.2.

Step 2: 7-Chloro-2,3-dihydrobenzo[b][1,4]dioxin-6-ol

Procedure: To a −78° C. cooled solution of N-chlorosuccinimide (1.9 g, 14.0 mmol, 1.05 eq.) in DCM (0.125 m) was added ZrCl$_4$ (619 mg, 2.7 mmol, 0.2 eq.) and 2,3-dihydrobenzo[b][1,4]dioxin-6-ol (2.0 g, 13.3 mmol, 1 eq.), successively. The reaction mixture was stirred at room temperature for 180 min and was quenched with saturated, aqueous NaHCO$_3$ solution. The crude was extracted with DCM, the combined organic layers were washed with brine and dried over Na$_2$SO$_4$. Then, the solvent was removed under reduced pressure and the product was purified via flash chromatography (SiO$_2$, nHex/EtOAc 10%).

Yield: 1.4 g, 7.3 mmol, 55% (pale green oil).
TLC: PE/EtOAc 25%
$^1$H NMR (CDCl$_3$, 200 MHz, ppm): δ 6.83 (s, 1H), 6.55 (s, 1H), 5.21 (s, 1H), 4.27-4.14 (m, 4H). $^{13}$C NMR (CDCl$_3$, 50 Hz, ppm): δ 145.9, 143.4, 137.8, 116.8, 111.5, 104.8, 64.6, 64.2.

Step 3: 7-Chloro-2,3-dihydrobenzo[b][1,4]dioxin-6-yl trifluoromethanesulfonate

Procedure: A solution of 7-chloro-2,3-dihydrobenzo[b][1,4]dioxin-6-ol (1.3 mg, 7.1 mmol, 1 eq.) in DCM (0.57 m) was cooled to 0° C. followed by the addition of iPr$_2$NH (994 μl, 7.1 mmol, 1 eq.) and Tf$_2$O (1.3 ml, 7.8 mmol, 1.1 eq.). The mixture was stirred at room temperature until complete consumption of the starting material was observed. Aqueous NaHCO$_3$ solution (5%) was used to quench the reaction, the resulting phases were separated and the aqueous phase was extracted with DCM. The combined organic layers were dried over Na$_2$SO$_4$ and the solvent was evaporated in vacuo. Flash chromatography (SiO$_2$, nHex/EtOAc 5%) yielded the purified product.

Yield: 1.5 g, 4.6 mmol, 64% (colorless oil).
TLC: PE/EtOAc 10%
$^1$H NMR (CDC$_3$, 200 MHz, ppm): δ 7.00 (s, 1H), 6.89 (s, 1H), 4.27 (s, 4H).

Step 4: 2-(7-Chloro-2,3-dihydrobenzo[b][1,4]dioxin-6-yl)-4,4,5,5-tetramethyl-1,3,2-dioxaborolane Procedure: Pd(PPh$_3$)$_2$Cl$_2$ (156 mg, 223 μmol, 0.05 eq.), B$_2$Pin$_2$ (1.7 g, 6.7 mmol, 1.5 eq.), KOAc (1.3 g, 13.4 mmol, 3 eq.) and 7-chloro-2,3-dihydrobenzo[b][1,4]dioxin-6-yltrifluoro methanesulfonate (1.4 g, 4.5 mmol, 1 eq.) were placed in an oven dried flask under argon atmosphere. Dry 1,4-dioxane (0.5 m) was added and the mixture was degassed with argon. The reaction mixture was heated to 100° C. overnight and then passed through a Celite pad, which was washed with EtOAc. Flash chromatography (SiO$_2$, nHex/EtOAc 5%) yielded the purified product.

Yield: 1.2 mg, 4.2 mmol, 94% (white solid).
TLC: PE/EtOAc 10%
$^1$H NMR (CDC$_3$, 200 MHz, ppm): δ 7.21 (s, 1H), 6.86 (s, 1H), 4.22 (s, 4H), 1.33 (s, 12H). $^{13}$C NMR (CDCl$_3$, 50 Hz, ppm): δ 146.2, 142.0, 131.8, 125.2, 118.3, 84.0, 64.7, 64.2, 24.9.

Step 5: N-(3-(5-(7-Chloro-2,3-dihydrobenzo[b][1,4]dioxin-6-yl)-1H-pyrrolo[2,3-b]pyridine-3-carbonyl)-2,4-difluorophenyl)propane-1-sulfonamide Procedure: The title compound was obtained by following GP ad.

Yield: 36 mg, 71 μmol, 41% (white solid).
TLC: DCM/MeOH 5%
$^1$H NMR (DMSO-d$_6$, 400 MHz, ppm): δ 13.02 (s, 1H), 9.77 (s, 1H), 8.43 (s, 1H), 8.39 (d, J=2.2 Hz, 1H), 8.24 (s, 1H), 7.58 (td, J=9.0, 5.9 Hz, 1H), 7.27 (td, J=9.0, 1.3 Hz, 1H), 7.14 (s, 1H), 7.05 (s, 1H), 4.31 (s, 4H), 3.16-3.07 (m, 2H), 1.80-1.67 (m, 2H), 0.96 (t, J=7.4 Hz, 3H). TLC-MS: m/z calculated for C$_{25}$H$_{20}$ClF$_2$N$_3$O$_5$S ([M-H]$^-$): 546.1, found: 546.6.

According to the general procedures outlined above, the compounds given in tables 2 and 3 were prepared:

TABLE 2

| Ex. | Chemical structure | MW |
|---|---|---|
| 45 | 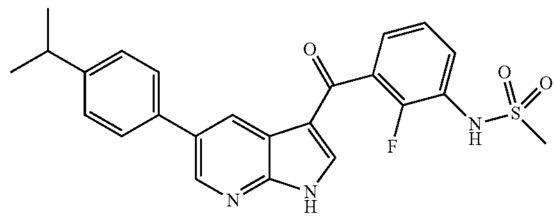 [SMILES: CC(C)c1ccc(-c2cnc3[nH]cc(C(=O)c4cccc(NS(C)(=O)=O)c4F)c3c2)cc1] | 451.52 |
| 46 | 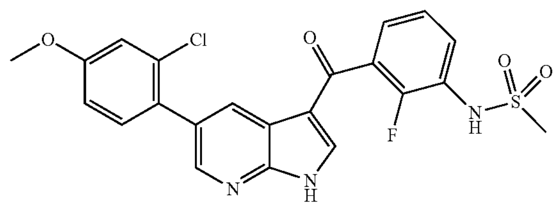 [SMILES: COc1ccc(-c2cnc3[nH]cc(C(=O)c4cccc(NS(C)(=O)=O)c4F)c3c2)c(Cl)c1] | 473.90 |
| 47 | 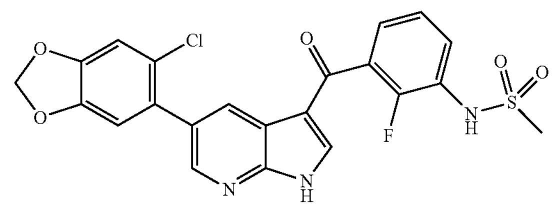 [SMILES: CS(=O)(=O)Nc1cccc(C(=O)c2c[nH]c3ncc(-c4cc5c(cc4Cl)OCO5)cc23)c1F] | 487.89 |
| 48 | 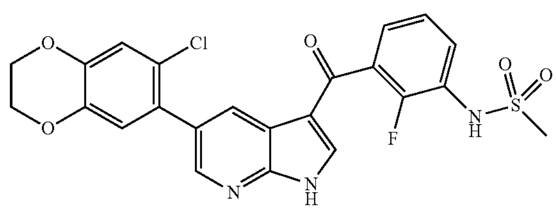 [SMILES: CS(=O)(=O)Nc1cccc(C(=O)c2c[nH]c3ncc(-c4cc5c(cc4Cl)OCCO5)cc23)c1F] | 501.91 |
| 49 | 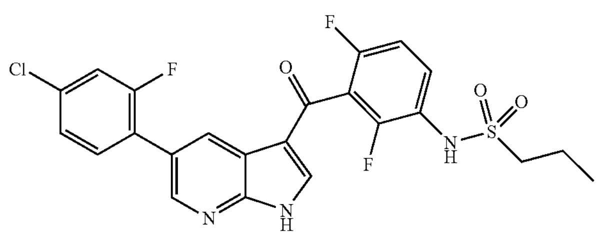 [SMILES: CCCS(=O)(=O)Nc1ccc(F)c(C(=O)c2c[nH]c3ncc(-c4ccc(Cl)cc4F)cc23)c1F] | 507.91 |
| 50 | 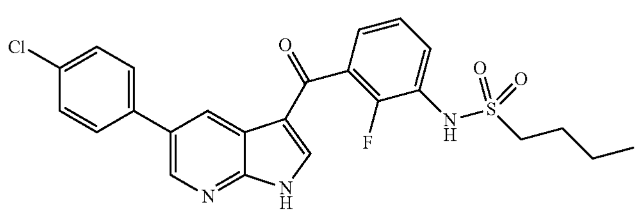 [SMILES: CCCCS(=O)(=O)Nc1cccc(C(=O)c2c[nH]c3ncc(-c4ccc(Cl)cc4)cc23)c1F] | 485.96 |
| 51 | 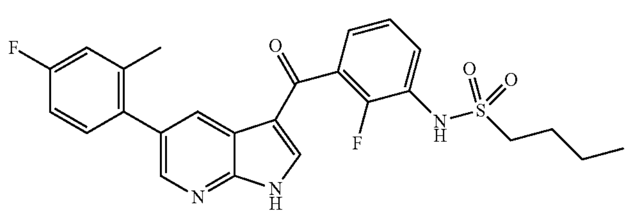 [SMILES: CCCCS(=O)(=O)Nc1cccc(C(=O)c2c[nH]c3ncc(-c4ccc(F)cc4C)cc23)c1F] | 483.53 |

TABLE 2-continued
| Ex. | Chemical structure | MW |
|---|---|---|
| 52 | 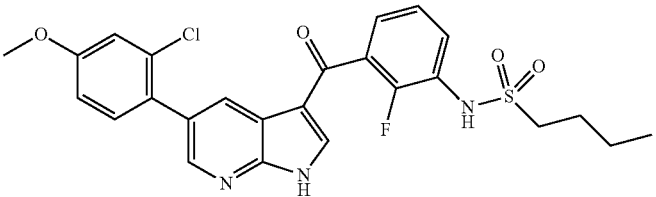 [SMILES: CCCCS(=O)(=O)Nc1cccc(C(=O)c2c[nH]c3ncc(-c4ccc(OC)cc4Cl)cc23)c1F] | 515.98 |
| 53 | 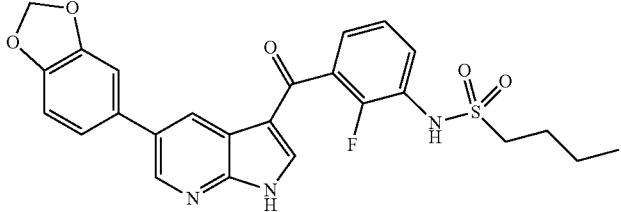 [SMILES: CCCCS(=O)(=O)Nc1cccc(C(=O)c2c[nH]c3ncc(-c4ccc5c(c4)OCO5)cc23)c1F] | 495.53 |
| 54 | 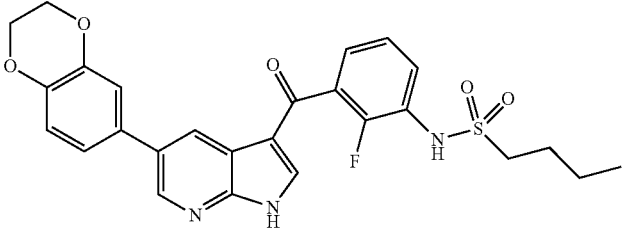 [SMILES: CCCCS(=O)(=O)Nc1cccc(C(=O)c2c[nH]c3ncc(-c4ccc5c(c4)OCCO5)cc23)c1F] | 509.55 |
| 55 | 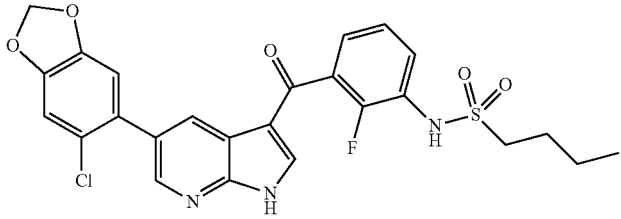 [SMILES: CCCCS(=O)(=O)Nc1cccc(C(=O)c2c[nH]c3ncc(-c4cc5c(cc4Cl)OCO5)cc23)c1F] | 529.97 |
| 56 | 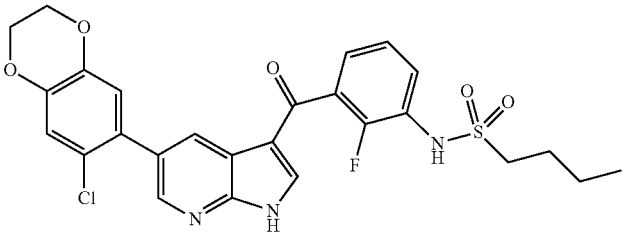 | 543.99 |
TABLE 3
| Ex. | Chemical structure | MW | Chemical name |
|---|---|---|---|
| 57 | 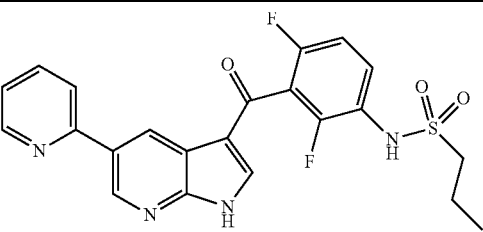 | 456.47 | N-(2,4-difluoro-3-(5-(pyridin-2-yl)-1H-pyrrolo[2,3-b]pyridine-3-carbonyl)phenyl)propane-1-sulfonamide |

TABLE 3-continued

| Ex. | Chemical structure | MW | Chemical name |
|---|---|---|---|
| 58 | 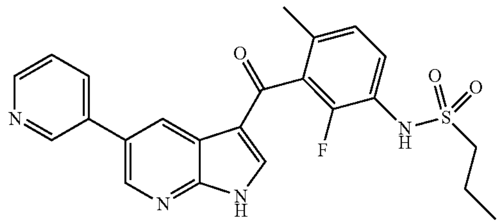 [SMILES: CCCS(=O)(=O)Nc1ccc(C)c(C(=O)c2c[nH]c3ncc(-c4cccnc4)cc23)c1F] | 452.50 | N-(2-fluoro-4-methyl-3-(5-(pyridin-3-yl)-1H-pyrrolo[2,3-b]pyridine-3-carbonyl)phenyl)propane-1-sulfonamide |
| 59 | 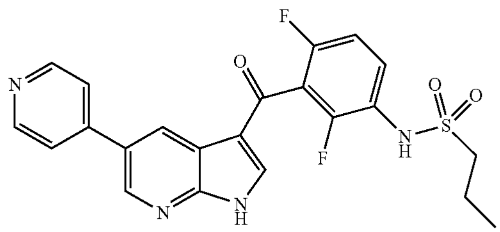 | 456.47 | N-(2,4-difluoro-3-(5-(pyridin-4-yl)-1H-pyrrolo[2,3-b]pyridine-3-carbonyl)phenyl)propane-1-sulfonamide |
| 60 | 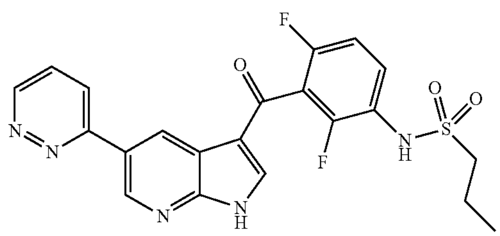 [SMILES: CCCS(=O)(=O)Nc1ccc(F)c(C(=O)c2c[nH]c3ncc(-c4cccnn4)cc23)c1F] | 457.46 | N-(2,4-difluoro-3-(5-(pyridazin-3-yl)-1H-pyrrolo[2,3-b]pyridine-3-carbonyl)phenyl)propane-1-sulfonamide |
| 61 | 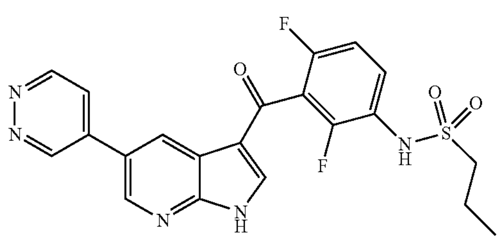 [SMILES: CCCS(=O)(=O)Nc1ccc(F)c(C(=O)c2c[nH]c3ncc(-c4ccnnc4)cc23)c1F] | 457.46 | N-(2,4-difluoro-3-(5-(pyridazin-4-yl)-1H-pyrrolo[2,3-b]pyridine-3-carbonyl)phenyl)propane-1-sulfonamide |
| 62 | 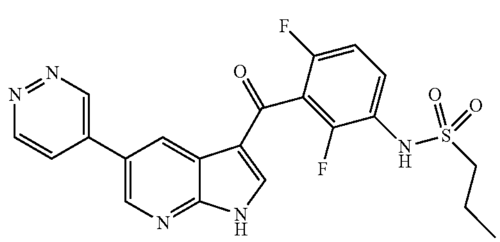 [SMILES: CCCS(=O)(=O)Nc1ccc(F)c(C(=O)c2c[nH]c3ncc(-c4ccnnc4)cc23)c1F] | 457.46 | N-(2,4-difluoro-3-(5-(pyridazin-4-yl)-1H-pyrrolo[2,3-b]pyridine-3-carbonyl)phenyl)propane-1-sulfonamide |
| 63 | 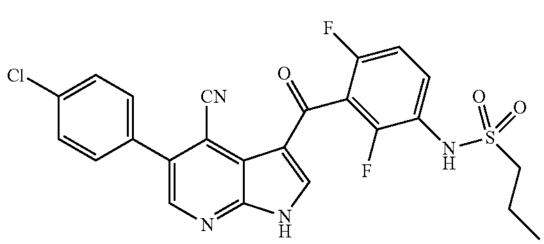 [SMILES: CCCS(=O)(=O)Nc1ccc(F)c(C(=O)c2c[nH]c3ncc(-c4ccc(Cl)cc4)c(C#N)c23)c1F] | 514.93 | N-(3-(5-(4-chlorophenyl)-4-cyano-1H-pyrrolo[2,3-b]pyridine-3-carbonyl)-2,4-difluorophenyl)propane-1-sulfonamide |

TABLE 3-continued

| Ex. | Chemical structure | MW | Chemical name |
|---|---|---|---|
| 64 | 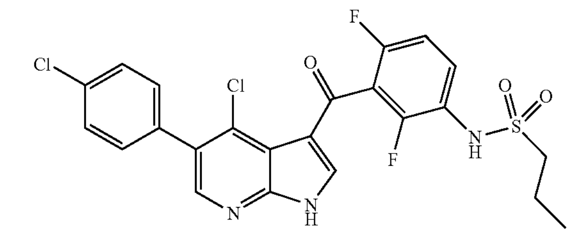 [SMILES: CCCS(=O)(=O)Nc1ccc(F)c(C(=O)c2c[nH]c3ncc(-c4ccc(Cl)cc4)c(Cl)c23)c1F] | 524.36 | N-(3-(4-chloro-5-(4-chlorophenyl)-1H-pyrrolo[2,3-b]pyridine-3-carbonyl)-2,4-difluorophenyl)propane-1-sulfonamide |
| 65 | 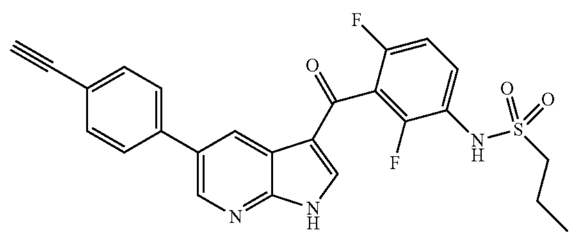 [SMILES: C#Cc1ccc(-c2cnc3[nH]cc(C(=O)c4c(F)ccc(NS(=O)(=O)CCC)c4F)c3c2)cc1] | 479.50 | N-(3-(5-(4-ethynylphenyl)-1H-pyrrolo[2,3-b]pyridine-3-carbonyl)-2,4-difluorophenyl)propane-1-sulfonamide |
| 66 | 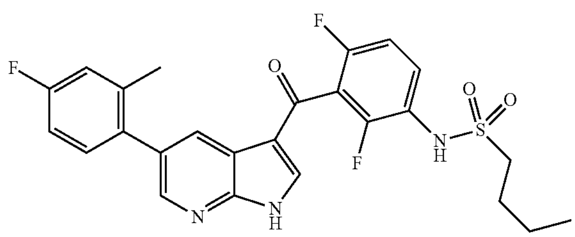 [SMILES: CCCCS(=O)(=O)Nc1ccc(F)c(C(=O)c2c[nH]c3ncc(-c4ccc(F)cc4C)cc23)c1F] | 501.52 | N-(2,4-difluoro-3-(5-(4-fluoro-2-methylphenyl)-1H-pyrrolo[2,3-b]pyridine-3-carbonyl)phenyl)butane-1-sulfonamide |
| 67 | 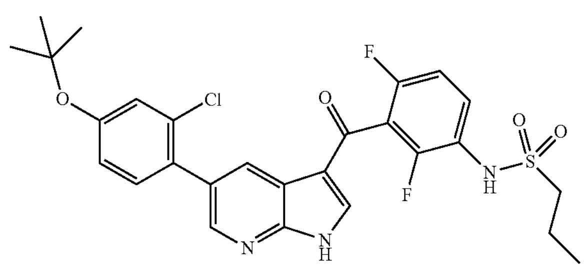 [SMILES: CCCS(=O)(=O)Nc1ccc(F)c(C(=O)c2c[nH]c3ncc(-c4ccc(OC(C)(C)C)cc4Cl)cc23)c1F] | 562.03 | N-(3-(5-(4-tert-butoxy-2-chlorophenyl)-1H-pyrrolo[2,3-b]pyridine-3-carbonyl)-2,4-difluorophenyl)propane-1-sulfonamide |
| 68 | 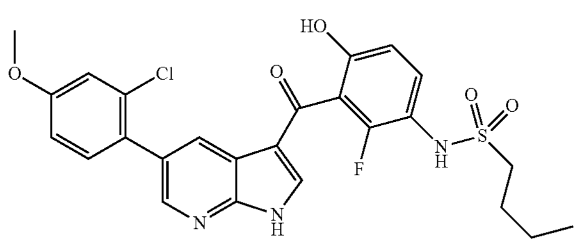 [SMILES: CCCCS(=O)(=O)Nc1ccc(O)c(C(=O)c2c[nH]c3ncc(-c4ccc(OC)cc4Cl)cc23)c1F] | 531.98 | N-(3-(5-(2-chloro-4-methoxyphenyl)-1H-pyrrolo[2,3-b]pyridine-3-carbonyl)-2-fluoro-4-hydroxyphenyl)butane-1-sulfonamide |
| 69 | 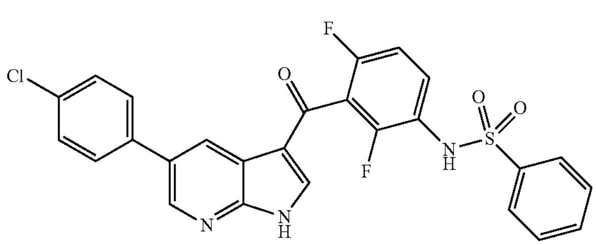 [SMILES: O=C(c1c(F)ccc(NS(=O)(=O)c2ccccc2)c1F)c1c[nH]c2ncc(-c3ccc(Cl)cc3)cc12] | 523.94 | N-(3-(5-(4-chlorophenyl)-1H-pyrrolo[2,3-b]pyridine-3-carbonyl)-2,4-difluorophenyl)(phenyl)methanesulfonamide |

TABLE 3-continued

| Ex. | Chemical structure | MW | Chemical name |
|---|---|---|---|
| 70 | 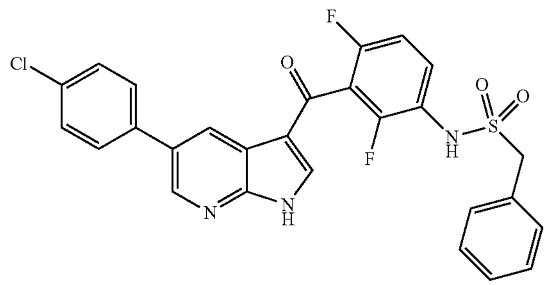 [SMILES: O=C(c1c(F)ccc(NS(=O)(=O)Cc2ccccc2)c1F)c1c[nH]c2ncc(-c3ccc(Cl)cc3)cc12] | 537.97 | N-(3-(5-(4-chlorophenyl)-1H-pyrrolo[2,3-b]pyridine-3-carbonyl)-2,4-difluorophenyl)cyclohexanesulfonamide |
| 71 | 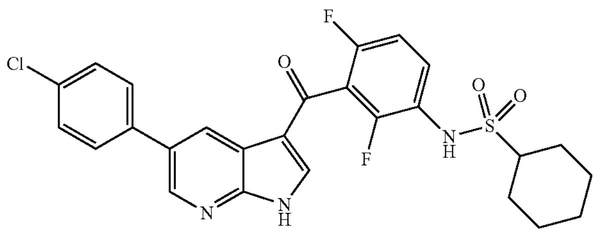 [SMILES: O=C(c1c(F)ccc(NS(=O)(=O)C2CCCCC2)c1F)c1c[nH]c2ncc(-c3ccc(Cl)cc3)cc12] | 529.99 | N-(3-(5-(4-chlorophenyl)-1H-pyrrolo[2,3-b]pyridine-3-carbonyl)-2,4-difluorophenyl)cyclopentanesulfonamide |
| 72 | 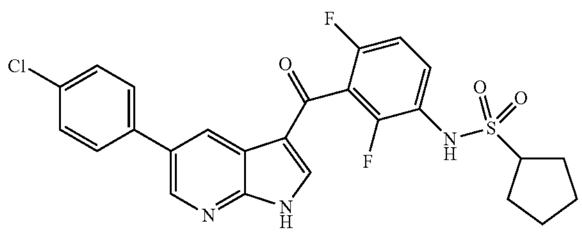 [SMILES: O=C(c1c(F)ccc(NS(=O)(=O)C2CCCC2)c1F)c1c[nH]c2ncc(-c3ccc(Cl)cc3)cc12] | 515.96 | N-(3-(5-(4-chlorophenyl)-1H-pyrrolo[2,3-b]pyridine-3-carbonyl)-2,4-difluorophenyl)cyclopropanesulfonamide |
| 73 | 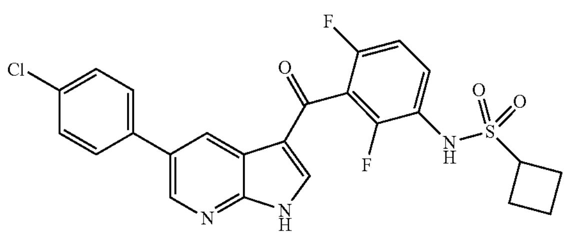 [SMILES: O=C(c1c(F)ccc(NS(=O)(=O)C2CCC2)c1F)c1c[nH]c2ncc(-c3ccc(Cl)cc3)cc12] | 501.93 | N-(3-(5-(4-chlorophenyl)-1H-pyrrolo[2,3-b]pyridine-3-carbonyl)-2,4-difluorophenyl)pentane-2-sulfonamide |
| 74 | 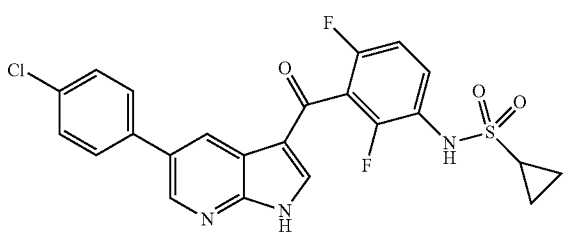 [SMILES: O=C(c1c(F)ccc(NS(=O)(=O)C2CC2)c1F)c1c[nH]c2ncc(-c3ccc(Cl)cc3)cc12] | 487.91 | N-(3-(5-(4-chlorophenyl)-1H-pyrrolo[2,3-b]pyridine-3-carbonyl)-2,4-difluorophenyl)-2-methylbutane-1-sulfonamide |
| 75 | 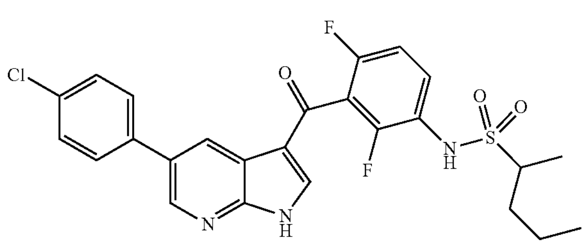 [SMILES: CCCC(C)S(=O)(=O)Nc1ccc(F)c(C(=O)c2c[nH]c3ncc(-c4ccc(Cl)cc4)cc23)c1F] | 517.98 | N-(3-(5-(4-chlorophenyl)-1H-pyrrolo[2,3-b]pyridine-3-carbonyl)-2,4-difluorophenyl)pentane-2-sulfonamide |

TABLE 3-continued

| Ex. | Chemical structure | MW | Chemical name |
|---|---|---|---|
| 76 | 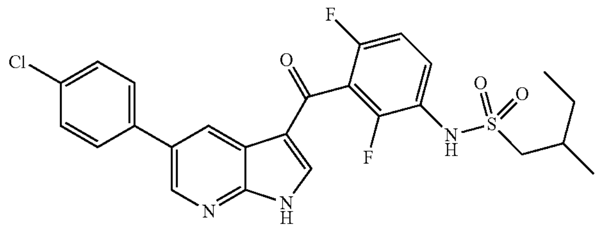 [SMILES: CCC(C)CS(=O)(=O)Nc1ccc(F)c(C(=O)c2c[nH]c3ncc(-c4ccc(Cl)cc4)cc23)c1F] | 517.98 | N-(3-(5-(4-chlorophenyl)-1H-pyrrolo[2,3-b]pyridine-3-carbonyl)-2,4-difluorophenyl)-2-methylbutane-1-sulfonamide |
| 77 | 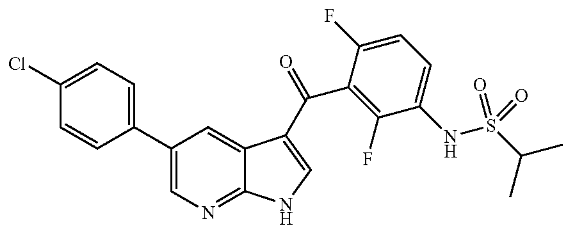 [SMILES: CC(C)S(=O)(=O)Nc1ccc(F)c(C(=O)c2c[nH]c3ncc(-c4ccc(Cl)cc4)cc23)c1F] | 489.92 | N-(3-(5-(4-chlorophenyl)-1H-pyrrolo[2,3-b]pyridine-3-carbonyl)-2,4-difluorophenyl)propane-2-sulfonamide |
| 78 | 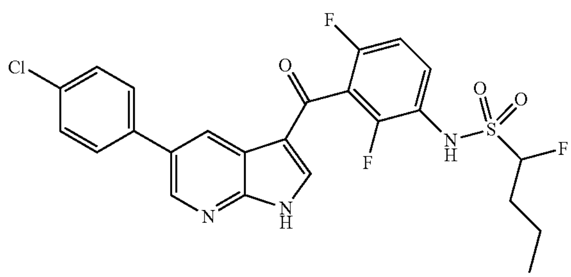 [SMILES: CCCC(F)S(=O)(=O)Nc1ccc(F)c(C(=O)c2c[nH]c3ncc(-c4ccc(Cl)cc4)cc23)c1F] | 521.94 | N-(3-(5-(4-chlorophenyl)-1H-pyrrolo[2,3-b]pyridine-3-carbonyl)-2,4-difluorophenyl)-1-fluorobutane-1-sulfonamide |
| 79 | 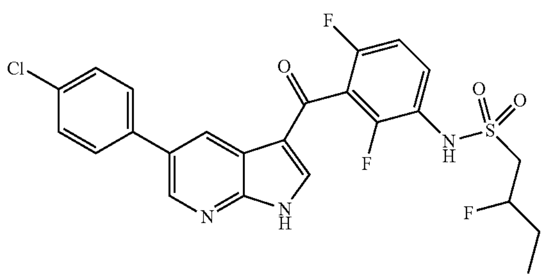 [SMILES: CCC(F)CS(=O)(=O)Nc1ccc(F)c(C(=O)c2c[nH]c3ncc(-c4ccc(Cl)cc4)cc23)c1F] | 521.94 | N-(3-(5-(4-chlorophenyl)-1H-pyrrolo[2,3-b]pyridine-3-carbonyl)-2,4-difluorophenyl)-2-fluorobutane-1-sulfonamide |
| 80 | 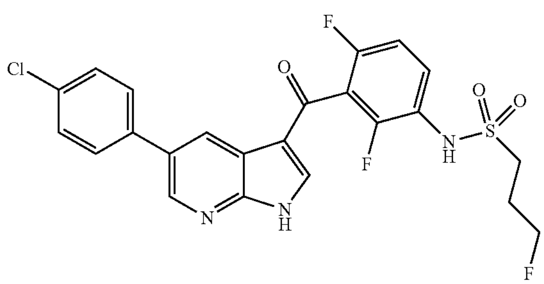 [SMILES: O=C(c1c(F)ccc(NS(=O)(=O)CCCF)c1F)c1c[nH]c2ncc(-c3ccc(Cl)cc3)cc12] | 507.91 | N-(3-(5-(4-chlorophenyl)-1H-pyrrolo[2,3-b]pyridine-3-carbonyl)-2,4-difluorophenyl)-3-fluoropropane-1-sulfonamide |
| 81 | 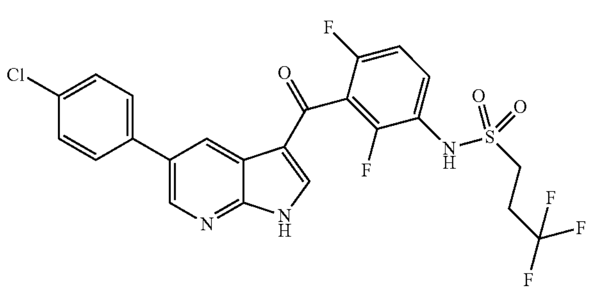 [SMILES: O=C(c1c(F)ccc(NS(=O)(=O)CCC(F)(F)F)c1F)c1c[nH]c2ncc(-c3ccc(Cl)cc3)cc12] | 543.89 | N-(3-(5-(4-chlorophenyl)-1H-pyrrolo[2,3-b]pyridine-3-carbonyl)-2,4-difluorophenyl)-3,3,3-trifluoropropane-1-sulfonamide |

TABLE 3-continued

| Ex. | Chemical structure | MW | Chemical name |
|---|---|---|---|
| 82 | 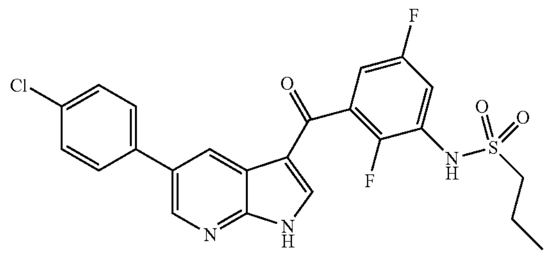 [SMILES: CCCS(=O)(=O)Nc1cc(F)cc(C(=O)c2c[nH]c3ncc(-c4ccc(Cl)cc4)cc23)c1F] | 489.92 | N-(3-(5-(4-chlorophenyl)-1H-pyrrolo[2,3-b]pyridine-3-carbonyl)-2,5-difluorophenyl)propane-1-sulfonamide |
| 83 | 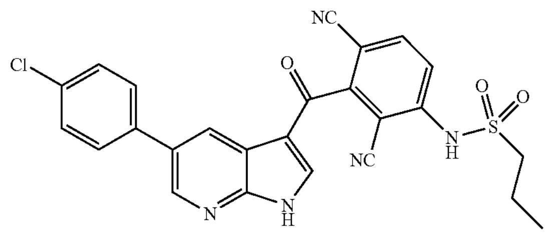 [SMILES: CCCS(=O)(=O)Nc1ccc(C#N)c(C(=O)c2c[nH]c3ncc(-c4ccc(Cl)cc4)cc23)c1C#N] | 503.96 | N-(3-(5-(4-chlorophenyl)-1H-pyrrolo[2,3-b]pyridine-3-carbonyl)-2,4-dicyanophenyl)propane-1-sulfonamide |
| 84 | 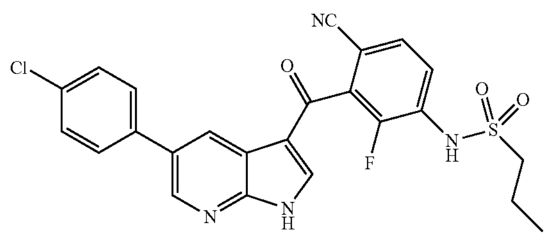 [SMILES: CCCS(=O)(=O)Nc1ccc(C#N)c(C(=O)c2c[nH]c3ncc(-c4ccc(Cl)cc4)cc23)c1F] | 496.94 | N-(3-(5-(4-chlorophenyl)-1H-pyrrolo[2,3-b]pyridine-3-carbonyl)-4-cyano-2-fluorophenyl)propane-1-sulfonamide |
| 85 | 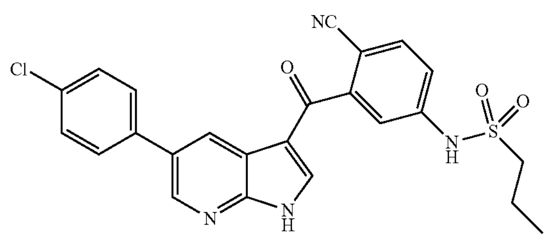 [SMILES: CCCS(=O)(=O)Nc1ccc(C#N)c(C(=O)c2c[nH]c3ncc(-c4ccc(Cl)cc4)cc23)c1] | 478.95 | N-(3-(5-(4-chlorophenyl)-1H-pyrrolo[2,3-b]pyridine-3-carbonyl)-4-cyanophenyl)propane-1-sulfonamide |
| 86 | 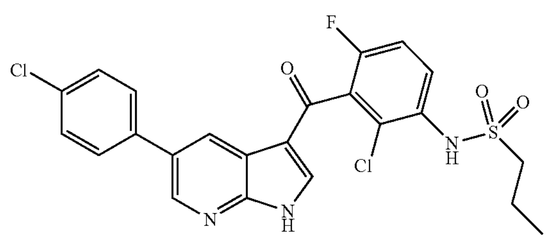 [SMILES: CCCS(=O)(=O)Nc1ccc(F)c(C(=O)c2c[nH]c3ncc(-c4ccc(Cl)cc4)cc23)c1Cl] | 506.37 | N-(2-chloro-3-(5-(4-chlorophenyl)-1H-pyrrolo[2,3-b]pyridine-3-carbonyl)-4-fluorophenyl)propane-1-sulfonamide |
| 87 | 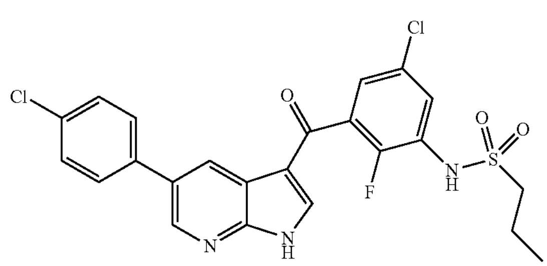 | 506.37 | N-(5-chloro-3-(5-(4-chlorophenyl)-1H-pyrrolo[2,3-b]pyridine-3-carbonyl)-2-fluorophenyl)propane-1-sulfonamide |

TABLE 3-continued

| Ex. | Chemical structure | MW | Chemical name |
|---|---|---|---|
| 88 | 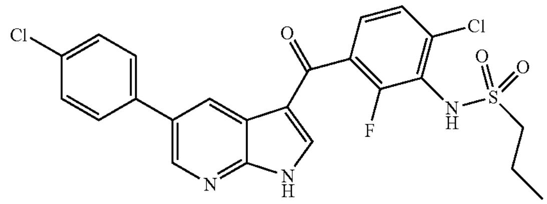 [SMILES: CCCS(=O)(=O)Nc1c(Cl)ccc(C(=O)c2c[nH]c3ncc(-c4ccc(Cl)cc4)cc23)c1F] | 506.37 | N-(6-chloro-3-(5-(4-chlorophenyl)-1H-pyrrolo[2,3-b]pyridine-3-carbonyl)-2-fluorophenyl)propane-1-sulfonamide |
| 89 | 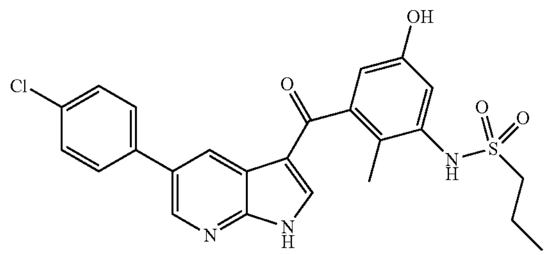 [SMILES: CCCS(=O)(=O)Nc1cc(O)cc(C(=O)c2c[nH]c3ncc(-c4ccc(Cl)cc4)cc23)c1C] | 483.97 | N-(3-(5-(4-chlorophenyl)-1H-pyrrolo[2,3-b]pyridine-3-carbonyl)-5-hydroxy-2-methylphenyl)propane-1-sulfonamide |
| 90 | 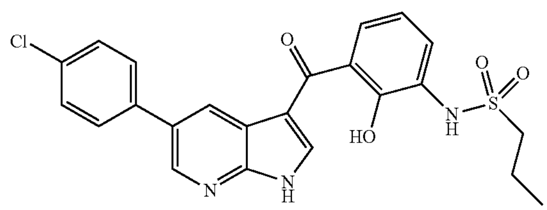 [SMILES: CCCS(=O)(=O)Nc1cccc(C(=O)c2c[nH]c3ncc(-c4ccc(Cl)cc4)cc23)c1O] | | N-(3-(5-(4-chlorophenyl)-1H-pyrrolo[2,3-b]pyridine-3-carbonyl)-2-hydroxyphenyl)propane-1-sulfonamide |
| 91 | 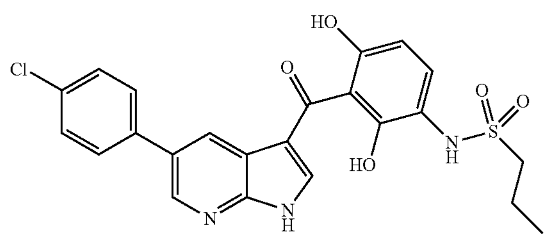 [SMILES: CCCS(=O)(=O)Nc1ccc(O)c(C(=O)c2c[nH]c3ncc(-c4ccc(Cl)cc4)cc23)c1O] | 485.94 | N-(3-(5-(4-chlorophenyl)-1H-pyrrolo[2,3-b]pyridine-3-carbonyl)-2,4-dihydroxyphenyl)propane-1-sulfonamide |
| 92 | 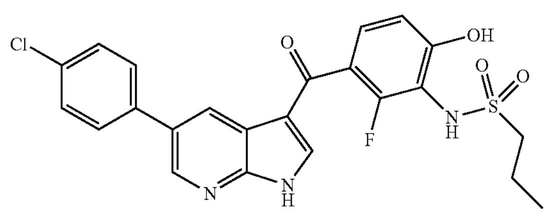 [SMILES: CCCS(=O)(=O)Nc1c(O)ccc(C(=O)c2c[nH]c3ncc(-c4ccc(Cl)cc4)cc23)c1F] | 487.93 | N-(3-(5-(4-chlorophenyl)-1H-pyrrolo[2,3-b]pyridine-3-carbonyl)-2-fluoro-6-hydroxyphenyl)propane-1-sulfonamide |
| 93 | 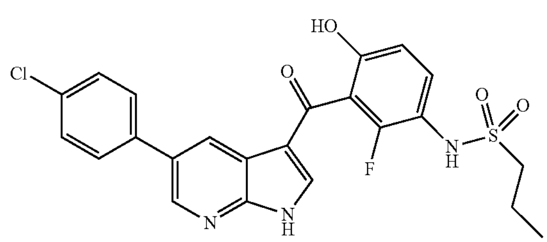 | 487.93 | N-(3-(5-(4-chlorophenyl)-1H-pyrrolo[2,3-b]pyridine-3-carbonyl)-2-fluoro-4-hydroxyphenyl)propane-1-sulfonamide |
| 94 | 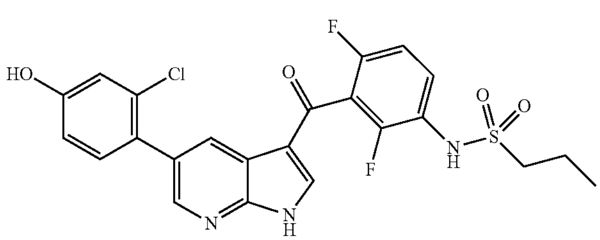 [SMILES: CCCS(=O)(=O)Nc1ccc(F)c(C(=O)c2c[nH]c3ncc(-c4ccc(O)cc4Cl)cc23)c1F] | 505.92 | N-(3-(5-(2-chloro-4-hydroxyphenyl)-1H-pyrrolo[2,3-b]pyridine-3-carbonyl)-2,4-difluorophenyl)propane-1-sulfonamide |

TABLE 3-continued

| Ex. | Chemical structure | MW | Chemical name |
|---|---|---|---|
| 95 | 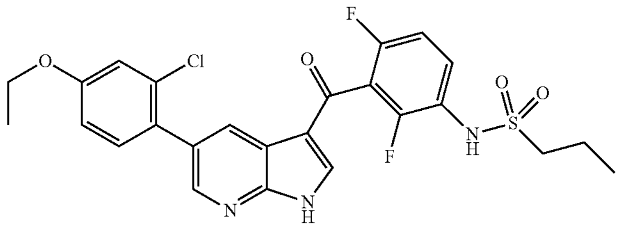 [SMILES: CCCS(=O)(=O)Nc1ccc(F)c(C(=O)c2c[nH]c3ncc(-c4ccc(OCC)cc4Cl)cc23)c1F] | 533.97 | N-(3-(5-(2-chloro-4-ethoxy-phenyl)-1H-pyrrolo[2,3-b]pyridine-3-carbonyl)-2,4-difluorophenyl)-propane-1-sulfonamide |
| 96 | 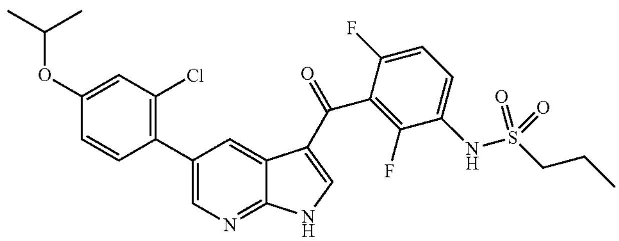 [SMILES: CCCS(=O)(=O)Nc1ccc(F)c(C(=O)c2c[nH]c3ncc(-c4ccc(OC(C)C)cc4Cl)cc23)c1F] | 548.00 | N-(3-(5-(2-chloro-4-isopropoxy-phenyl)-1H-pyrrolo[2,3-b]pyridine-3-carbonyl)-2,4-difluorophenyl)-propane-1-sulfonamide |
| 97 | 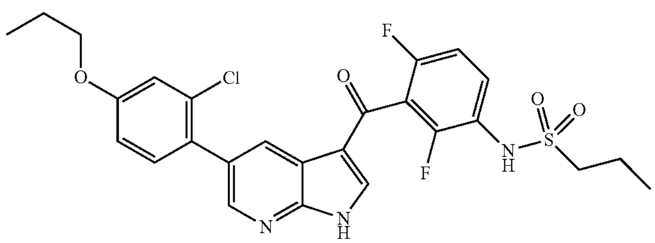 [SMILES: CCCOc1ccc(-c2cnc3[nH]cc(C(=O)c4c(F)ccc(NS(=O)(=O)CCC)c4F)c3c2)c(Cl)c1] | 548.00 | N-(3-(5-(2-chloro-4-propoxy-phenyl)-1H-pyrrolo[2,3-b]pyridine-3-carbonyl)-2,4-difluorophenyl)-propane-1-sulfonamide |
| 98 | 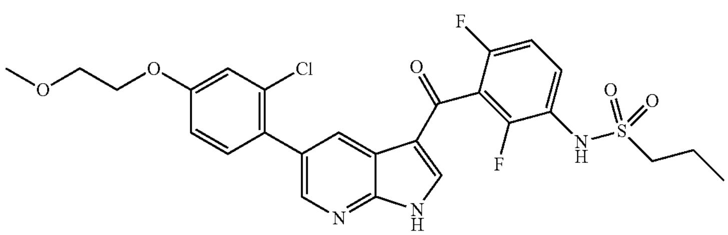 [SMILES: CCCS(=O)(=O)Nc1ccc(F)c(C(=O)c2c[nH]c3ncc(-c4ccc(OCCOC)cc4Cl)cc23)c1F] | 564.00 | N-(3-(5-(2-chloro-4-(2-methoxy-ethoxy)phenyl)-1H-pyrrolo[2,3-b]pyridine-3-carbonyl)-2,4-difluorophenyl)propane-1-sulfonamide |
| 99 | 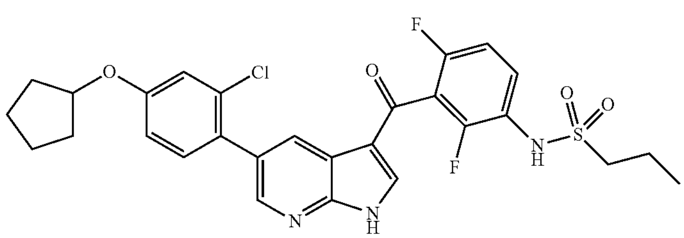 [SMILES: CCCS(=O)(=O)Nc1ccc(F)c(C(=O)c2c[nH]c3ncc(-c4ccc(OC5CCCC5)cc4Cl)cc23)c1F] | 574.04 | N-(3-(5-(2-chloro-4-(cyclopentyl-oxy)phenyl)-1H-pyrrolo[2,3-b]pyridine-3-carbonyl)-2,4-difluorophenyl)propane-1-sulfonamide |
| 100 | 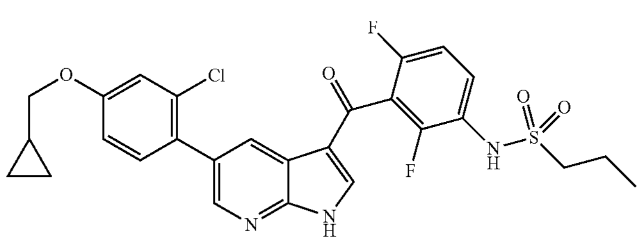 [SMILES: CCCS(=O)(=O)Nc1ccc(F)c(C(=O)c2c[nH]c3ncc(-c4ccc(OCC5CC5)cc4Cl)cc23)c1F] | 560.01 | N-(3-(5-(2-chloro-4-(cyclopropyl-methoxy)phenyl)-1H-pyrrolo[2,3-b]pyridine-3-carbonyl)-2,4-difluorophenyl)propane-1-sulfonamide |

TABLE 3-continued

| Ex. | Chemical structure | MW | Chemical name |
|---|---|---|---|
| 101 | 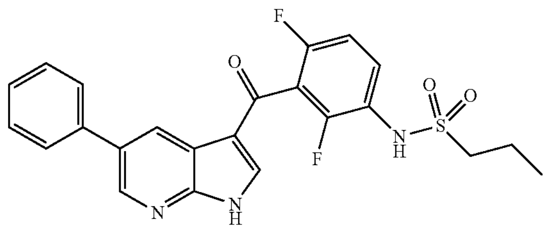 [SMILES: CCCS(=O)(=O)Nc1ccc(F)c(C(=O)c2c[nH]c3ncc(-c4ccccc4)cc23)c1F] | 455.48 | N-(2,4-difluoro-3-(5-phenyl-1H-pyrrolo[2,3-b]pyridine-3-carbonyl)phenyl)propane-1-sulfonamide |
| 102 | 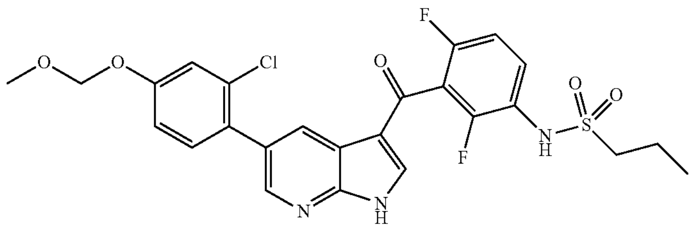 [SMILES: CCCS(=O)(=O)Nc1ccc(F)c(C(=O)c2c[nH]c3ncc(-c4ccc(OCOC)cc4Cl)cc23)c1F] | 549.97 | N-(3-(5-(2-chloro-4-(methoxymethoxy)phenyl)-1H-pyrrolo[2,3-b]pyridine-3-carbonyl)-2,4-difluorophenyl)propane-1-sulfonamide |
| 103 | 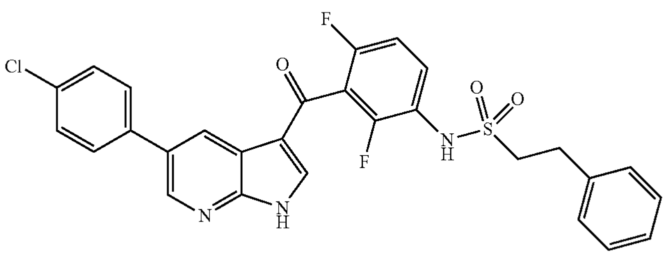 [SMILES: O=C(c1c(F)ccc(NS(=O)(=O)CCc2ccccc2)c1F)c1c[nH]c2ncc(-c3ccc(Cl)cc3)cc12] | 551.99 | N-(3-(5-(4-chlorophenyl)-1H-pyrrolo[2,3-b]pyridine-3-carbonyl)-2,4-difluorophenyl)-2-phenylethane-1-sulfonamide |

The following compounds were prepared according to the reaction sequences given below using conventional methods:

Example 104: Synthesis of N-(3-(2-(5-(4-chlorophenyl)-1H-pyrrolo[2,3-b]pyridin-3-yl)-1,3-dioxolan-2-yl)-2,4-difluorophenyl)propane-1-sulfonamide

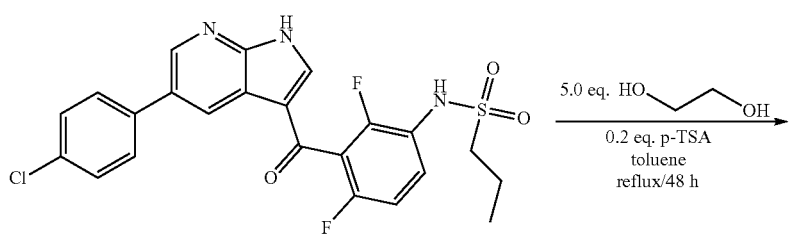

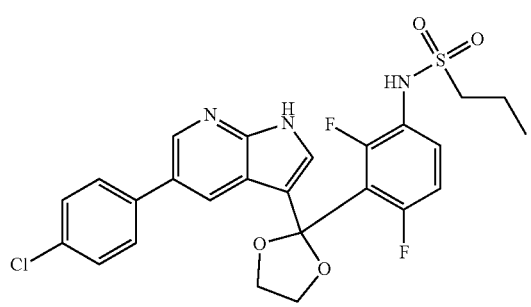

Example 105: Synthesis of N-(3-((5-(4-chlorophenyl)-1H-pyrrolo[2,3-b]pyridin-3-yl)methyl)-2,4-difluorophenyl)propane-1-sulfonamide

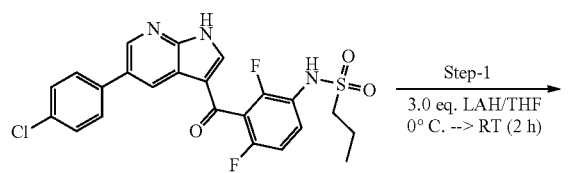

Step-1
3.0 eq. LAH/THF
0° C. --> RT (2 h)

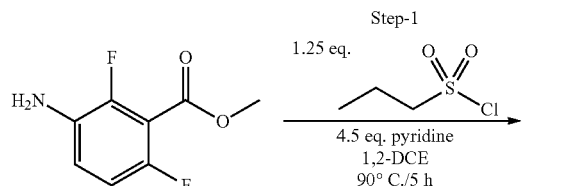

Step-2
1.5 eq. Et₃SiH
2.0 eq. TfOH
DCM/
0° C. --> RT (16 h)

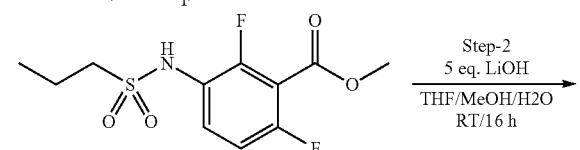

Example 106: Synthesis of N-(5-(4-chlorophenyl)-1H-pyrrolo[2,3-b]pyridin-3-yl)-2,6-difluoro-3-(propylsulfonamido)benzamide Synthesis of Intermediates E (used for Example 106) and F (used for Example 107)

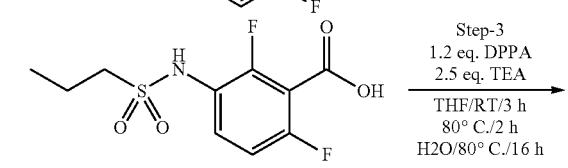

Step-1
1.25 eq.
4.5 eq. pyridine
1,2-DCE
90° C./5 h

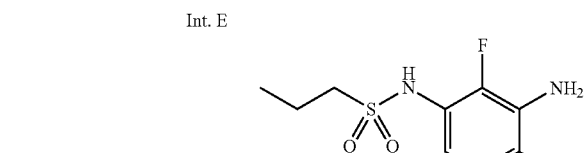

Step-2
5 eq. LiOH
THF/MeOH/H2O
RT/16 h

Step-3
1.2 eq. DPPA
2.5 eq. TEA
THF/RT/3 h
80° C./2 h
H2O/80° C./16 h

Int. E

Int. F

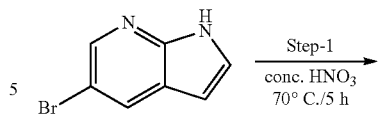

Step-1
conc. HNO₃
70° C./5 h

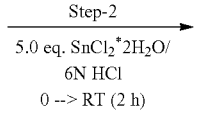

Step-2
5.0 eq. SnCl₂·2H₂O/
6N HCl
0 --> RT (2 h)

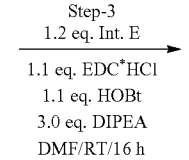

Step-3
1.2 eq. Int. E
1.1 eq. EDC·HCl
1.1 eq. HOBt
3.0 eq. DIPEA
DMF/RT/16 h

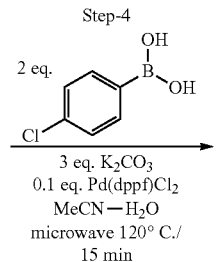

Step-4
2 eq.
3 eq. K₂CO₃
0.1 eq. Pd(dppf)Cl₂
MeCN—H₂O
microwave 120° C./
15 min

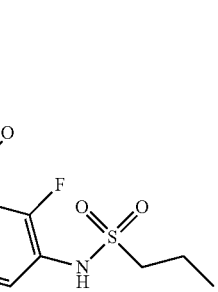

Example 107: Synthesis of 5-(4-chlorophenyl)-N-(2,6-difluoro-3-(propylsulfonamido)phenyl)-1H-pyrrolo[2,3-b]pyridine-3-carboxamide

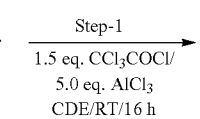

Step-1
1.5 eq. CCl₃COCl/
5.0 eq. AlCl₃
CDE/RT/16 h

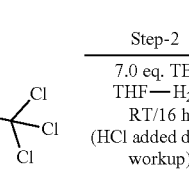

Step-2
7.0 eq. TEA
THF—H₂O
RT/16 h
(HCl added during workup)

-continued
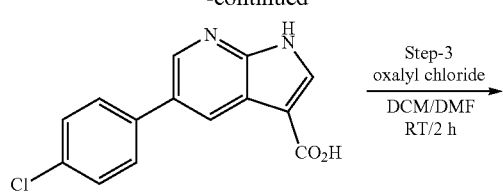
Step-3
oxalyl chloride
DCM/DMF
RT/2 h
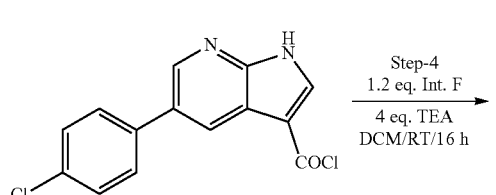
Step-4
1.2 eq. Int. F
4 eq. TEA
DCM/RT/16 h
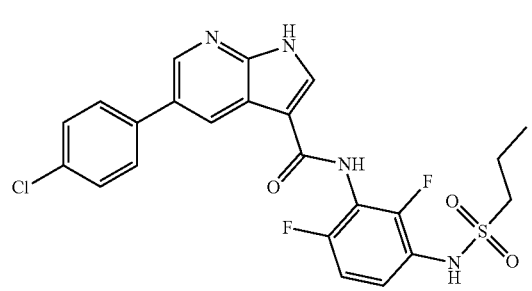
Examples 108-110
Synthesis of Intermediate C:
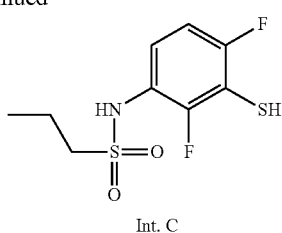
Int. C
Step-1
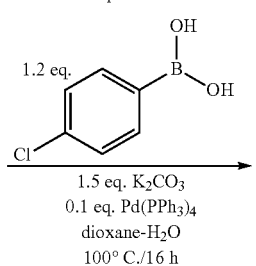
1.2 eq.
1.5 eq. K₂CO₃
0.1 eq. Pd(PPh₃)₄
dioxane-H₂O
100° C./16 h
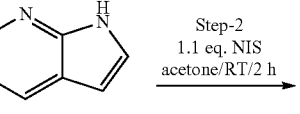
Step-2
1.1 eq. NIS
acetone/RT/2 h
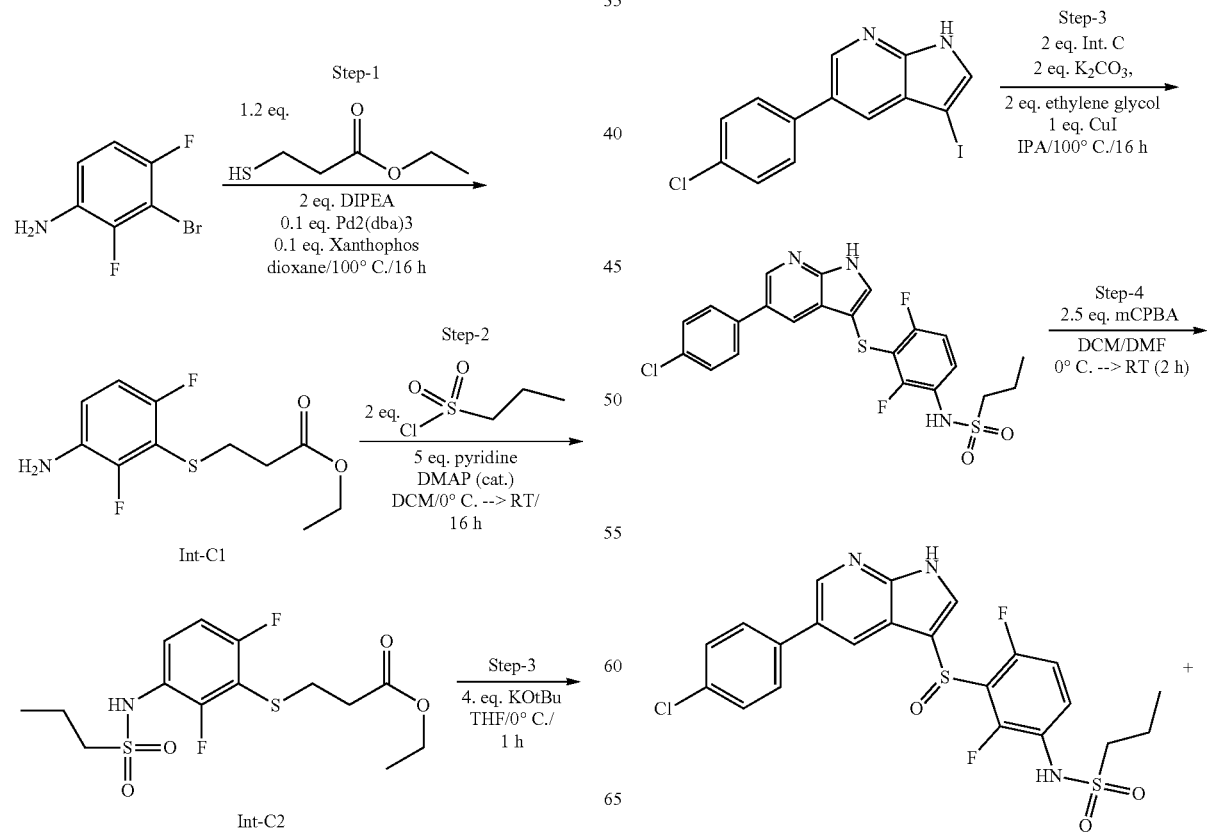

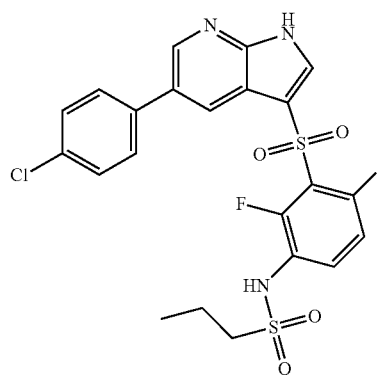
Example 111: Synthesis of N-(4-(5-(4-chlorophenyl)-1H-pyrrolo[2,3-b]pyridine-3-carbonyl)thiazol-2-yl)propane-1-sulfonamide
Synthesis of Intermediate G
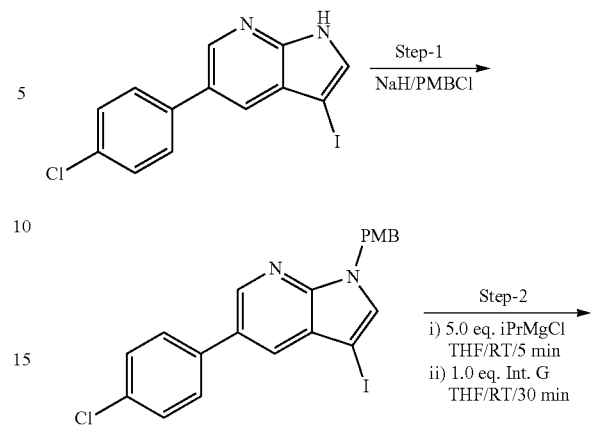
Example 112: Synthesis of N-(3-(5-(4-chlorophenyl)-1H-pyrrolo[2,3-b]pyridine-3-carbonyl)-2,4-difluorophenyl)propane-1-sulfonimidamide
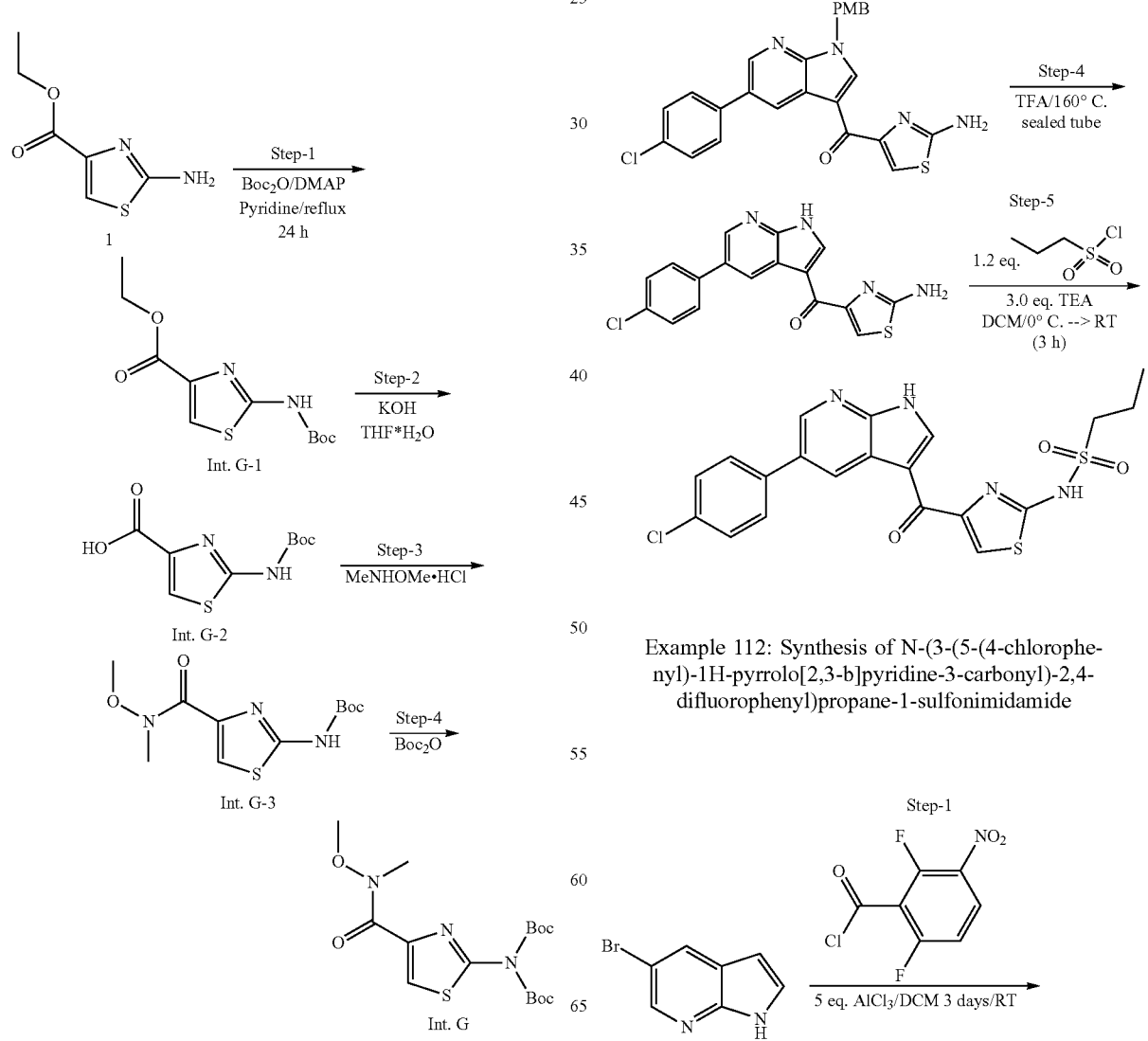

-continued

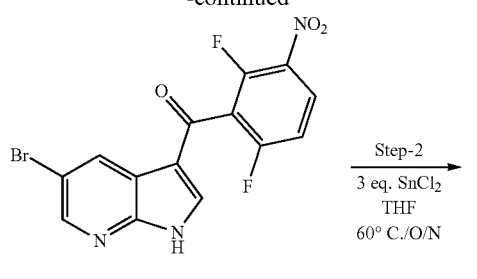

Step-2
3 eq. SnCl₂
THF
60° C./O/N

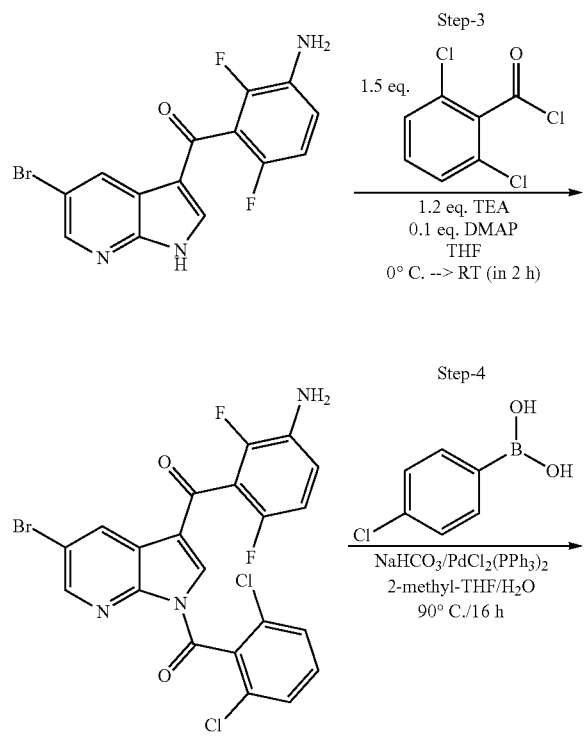

Step-3
1.5 eq.
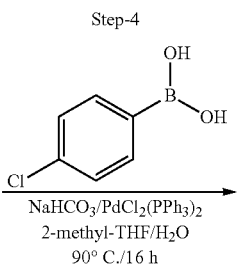
1.2 eq. TEA
0.1 eq. DMAP
THF
0° C. --> RT (in 2 h)

Step-4
NaHCO₃/PdCl₂(PPh₃)₂
2-methyl-THF/H₂O
90° C./16 h

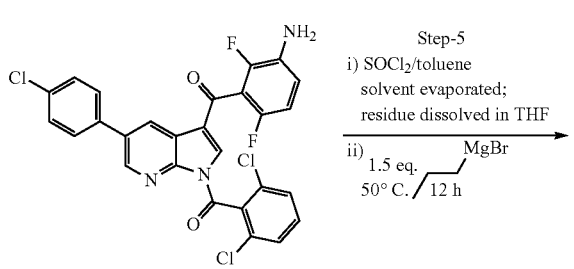

Step-5
i) SOCl₂/toluene
  solvent evaporated;
  residue dissolved in THF
ii) 1.5 eq. MgBr
   50° C./12 h

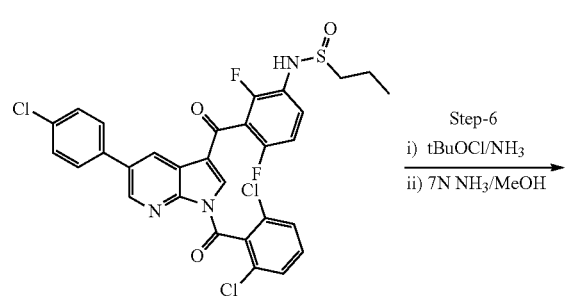

Step-6
i) tBuOCl/NH₃
ii) 7N NH₃/MeOH

-continued

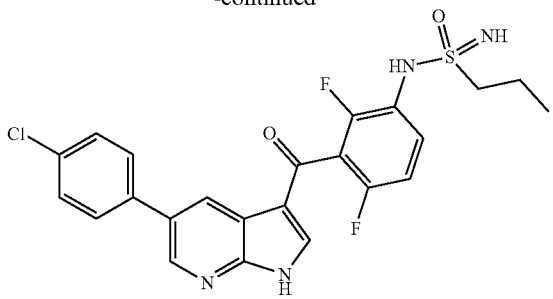

Example 113: Biological Activity

Example 113-1: Binding Assays

The kinase activities of the compounds of the invention were measured using KINOMEscan™ Profiling Service at DiscoveRx Corporation, 42501 Albrae St. Fremont, Calif. 94538, USA which is based on a competition binding assay that quantitatively measures the ability of a compound to compete with an immobilized, active-site directed ligand. The assay was performed by combining three components: DNA-tagged kinase; immobilized ligand; and a test compound. The ability of the test compound to compete with the immobilized ligand was measured via quantitative PCR of the DNA tag. The technology is described in detail in Fabian, M. A. et al. A small molecule-kinase interaction map for clinical kinase inhibitors. Nat. Biotechnol., 23, 329-336 (2005) and in Karaman, M. W. et al. A quantitative analysis of kinase inhibitor selectivity. Nat. Biotechnol., 26, 127-132 (2008).

For investigation of the affinity to MKK4, MKK7 and JNK1, the kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SEABLOCK™ (Pierce), 1% BSA, 0.05% TWEEN®20, 1 mM DTT) to remove unbound ligand and to reduce nonspecific binding. Binding reactions were assembled by combining kinases, liganded affinity beads, and test compounds in 1× binding buffer (20% SEABLOCK™, 0.17×PBS, 0.05% TWEEN®20, 6 mM DTT). All reactions were performed in polystyrene 96-well plates in a final volume of 0.135 mL. The assay plates were incubated at room temperature with shaking for 1 hour and the affinity beads were washed with wash buffer (1×PBS, 0.05% TWEEN®20). The beads were then re-suspended in elution buffer (1×PBS, 0.05% TWEEN®20, 0.5 11M non-biotinylated affinity ligand) and incubated at room temperature with shaking for 30 minutes. The kinase concentration in the eluates was measured by qPCR.

Average Z' values and standard deviations were calculated for each kinase based on fourteen control wells per experiment in over 135 independent experiments spanning a period of sixteen months. Average Z'=0.71.

Potency of Test Compounds:

The compounds were screened at the indicated concentrations and results for binding interactions are reported as [% of control], where lower numbers indicate stronger binding, i.e. higher potency.

Details regarding the kinases tested are given in table 4 below.

The test compounds were provided as 10 mM stock solutions. The test solutions at indicated final concentrations were prepared at DiscoverX. The results are given in tables 5 to 7 below.

TABLE 4

| Group | MKK4 STE | MKK7 7 STE | JNK1 CMCG |
|---|---|---|---|
| Kinase Construct | Partial Length | Full Length | Full length |
| Accession Number | NP_003001.1 | NP_660186.1 | NP_002741.1 |
| Species | Human | Human | Human |
| Kinase Form | Wild Type | Wild Type | Wild Type |
| Expression System | Mammalian | Mammalian | Mammalian |
| Amino Acid Start/Stop | S84/D399 | M1/R419 | M1/Q384 |
| Average Z' Panel | 0.67 | 0.78 | 0.79 |

TABLE 5

MKK4 potency

| Example | Test conc. [μM] | Potency* MKK4 |
|---|---|---|
| 1 | 1.0 | + |
| 2 | 1.0 | ++ |
| 3 | 0.1 | + |
| 4 | 0.1 | + |
| 5 | 0.1 | + |
| 6 | 0.1 | O |
| 7 | 0.1 | O |
| 8 | 0.1 | O |
| 9 | 0.1 | O |
| 10 | 0.1 | ++ |
| 11 | 0.1 | + |
| 12 | 0.1 | + |
| 13 | 0.1 | + |
| 14 | 0.1 | + |
| 15 | 0.1 | + |
| 16 | 0.1 | O |
| 17 | 0.1 | + |
| 18 | 0.1 | O |
| 19 | 0.1 | + |
| 20 | 0.1 | + |
| 21 | 0.1 | + |
| 22 | 0.1 | + |
| 23 | 0.1 | + |
| 24 | 0.1 | O |
| 25 | 0.1 | O |
| 26 | 0.1 | O |
| 27 | 0.1 | + |
| 28 | 0.1 | O |
| 29 | 0.1 | O |
| 30 | 0.1 | O |
| 31 | 0.1 | O |
| 32 | 0.1 | O |
| 33 | 0.1 | + |
| 34 | 0.1 | ++ |
| 35 | 0.1 | + |
| 36 | 0.1 | ++ |
| 37 | 0.1 | ++ |
| 38 | 0.1 | + |
| 39 | 0.1 | ++ |
| 40 | 0.1 | + |
| 41 | 0.1 | O |
| 42 | 0.1 | + |
| 43 | 0.1 | N/D |
| 44 | 0.1 | ++ |
| 45 | 0.1 | O |
| 46 | 0.1 | ++ |
| 47 | 0.1 | ++ |
| 48 | 0.1 | + |
| 49 | 0.1 | ++ |
| 50 | 0.1 | + |
| 51 | 0.1 | ++ |
| 52 | 0.1 | ++ |
| 53 | 0.1 | ++ |
| 54 | 0.1 | ++ |
| 55 | 0.1 | ++ |
| 56 | 0.1 | ++ |
| 69 | 0.1 | ++ |
| 70 | 0.1 | ++ |
| 71 | 0.1 | + |
| 74 | 0.1 | O |
| 81 | 0.1 | ++ |
| 94 | 0.1 | ++ |
| 95 | 0.1 | ++ |
| 96 | 0.1 | + |
| 97 | 0.1 | + |
| 98 | 0.1 | ++ |
| 99 | 0.1 | O |
| 100 | 0.1 | O |
| 101 | 0.1 | ++ |
| 102 | 0.1 | ++ |
| 103 | 0.1 | + |
| 104 | 1 | O |
| 105 | 1 | O |
| 106 | 1 | O |
| 107 | 1 | O |
| 108 | 1 | O |
| 109 | 1 | O |
| 110 | 1 | O |
| 111 | 1 | O |
| 112 | 0.1 | + |

*potency derived from [% of control] values (PoC) according to the following classification rule:

| Test conc. | PoC <1% | >1-10% | >10-30% | >30% |
|---|---|---|---|---|
| 10 μM | + | + | o | o |
| 1 μM | ++ | + | o | o |
| 0.1 μM | ++ | ++ | + | o |

TABLE 6

Selectivity against JNK1

| Example | Test conc [μM] | Selectivity JNK1/MKK4 |
|---|---|---|
| 1 | 10 | N/D |
| 2 | 10 | >50 |
| 3 | 10 | >400 |
| 4 | 10 | >400 |
| 5 | 10 | >100 |
| 6 | 10 | >100 |
| 7 | 10 | >100 |
| 8 | 10 | >100 |
| 9 | 10 | >10 |
| 10 | 10 | >100 |
| 11 | 10 | >100 |
| 12 | 10 | >100 |
| 13 | 10 | >100 |
| 14 | 10 | 23 |
| 15 | 10 | >100 |
| 16 | 10 | >100 |
| 17 | 10 | 8 |
| 18 | 10 | 40 |
| 19 | 10 | 1 |

TABLE 6-continued

Selectivity against JNK1

| Example | Test conc [μM] | Selectivity JNK1/MKK4 |
|---|---|---|
| 20 | 0.1 | N/E* |
| 21 | 0.1 | N/E* |
| 22 | 0.1 | N/E* |
| 23 | 0.1 | N/E* |
| 24 | 0.1 | N/E* |
| 25 | 0.1 | N/E* |
| 26 | 0.1 | N/E* |
| 27 | 0.1 | N/E* |
| 28 | 0.1 | N/E* |
| 29 | 0.1 | N/E* |
| 30 | 0.1 | N/E* |
| 31 | 0.1 | N/E* |
| 32 | 0.1 | N/E* |
| 33 | 0.1 | N/E* |
| 34 | 0.1 | N/E* |
| 35 | 0.1 | N/E* |
| 36 | 0.1 | N/E* |
| 37 | 0.1 | N/E* |
| 38 | 0.1 | N/E* |
| 39 | 0.1 | N/E* |
| 40 | 0.1 | N/E* |
| 41 | 0.1 | N/E* |
| 42 | 0.1 | N/E* |
| 43 | 0.1 | N/E* |
| 44 | 0.1 | N/E* |
| 45 | 0.1 | N/E* |
| 46 | 0.1 | N/E* |
| 47 | 0.1 | 10 |
| 48 | 0.1 | 8.4 |
| 49 | 0.1 | 7.1 |
| 50 | 0.1 | N/E* |
| 51 | 0.1 | N/E* |
| 52 | 0.1 | 17 |
| 53 | 0.1 | N/E* |
| 54 | 0.1 | 55 |
| 55 | 0.1 | 14 |
| 56 | 0.1 | 24 |
| 69 | 0.1 | N/E* |
| 70 | 0.1 | N/E* |
| 71 | 0.1 | N/E* |
| 74 | 0.1 | N/E* |
| 81 | 0.1 | N/E* |
| 94 | 0.1 | 25 |
| 95 | 0.1 | 8.6 |
| 96 | 0.1 | 8.7 |
| 97 | 0.1 | 8.6 |
| 98 | 0.1 | 16 |
| 99 | 0.1 | 2.0 |
| 100 | 0.1 | 2.2 |
| 101 | 0.1 | 28 |
| 102 | 0.1 | N/E* |
| 103 | 0.1 | N/E* |
| 104 | 0.1 | N/E* |
| 105 | 0.1 | N/E* |
| 106 | 0.1 | N/E* |
| 107 | 0.1 | N/E* |
| 108 | 0.1 | <1 |
| 109 | 0.1 | N/E* |
| 110 | 0.1 | N/E* |
| 111 | 0.1 | N/E* |
| 112 | 0.1 | 3.5 |

N/E*: PoC for JNK1 = 100;

Due to the value of PoC for JNK1=100 it is clear that the compounds 20 to 43 of the invention inhibit MKK4 with high selectivity over JNK1.

TABLE 7

MKK4 potency and Selectivity against MKK7

| Example | Test conc. [μM] | Selectivity MKK7/MKK4 |
|---|---|---|
| 1 | 10 | 86 |
| 2 | 10 | >500 |
| 3 | 0.1 | 10 |
| 4 | 0.1 | 25 |
| 5 | 0.1 | 22 |
| 6 | 0.1 | 5.6 |
| 7 | 0.1 | 3.0 |
| 8 | 0.1 | 7.6 |
| 9 | 0.1 | 6.7 |
| 10 | 0.1 | 270 |
| 11 | 0.1 | 25 |
| 12 | 0.1 | 10 |
| 13 | 0.1 | 10 |
| 14 | 0.1 | 10 |
| 15 | 0.1 | 30 |
| 16 | 0.1 | 8 |
| 17 | 0.1 | 13 |
| 18 | 0.1 | 3 |
| 19 | 0.1 | 60 |
| 20 | 0.1 | 4.3 |
| 21 | 0.1 | 5.4 |
| 22 | 0.1 | 8.3 |
| 23 | 0.1 | 4.3 |
| 24 | 0.1 | 1.0 |
| 25 | 0.1 | 1.0 |
| 26 | 0.1 | 1.4 |
| 27 | 0.1 | 5.8 |
| 28 | 0.1 | 0.9 |
| 29 | 0.1 | 2.0 |
| 30 | 0.1 | 1.8 |
| 31 | 0.1 | 3.2 |
| 32 | 0.1 | 1.6 |
| 33 | 0.1 | 3.1 |
| 34 | 0.1 | 28.4 |
| 35 | 0.1 | 2.9 |
| 36 | 0.1 | 19.6 |
| 37 | 0.1 | 14.1 |
| 38 | 0.1 | 5.3 |
| 39 | 0.1 | 37.0 |
| 40 | 0.1 | 5.6 |
| 41 | 0.1 | 3.3 |
| 42 | 0.1 | 1.3 |
| 43 | 0.1 | 9.1 |
| 44 | 0.1 | 18 |
| 45 | 0.1 | N/E* |
| 46 | 0.1 | 10 |
| 47 | 0.1 | 9.7 |
| 48 | 0.1 | 8.7 |
| 49 | 0.1 | N/E* |
| 50 | 0.1 | N/E* |
| 51 | 0.1 | N/E* |
| 52 | 0.1 | N/E* |
| 53 | 0.1 | N/E* |
| 54 | 0.1 | 61 |
| 55 | 0.1 | N/E* |
| 56 | 0.1 | N/E* |
| 69 | 0.1 | 25 |
| 70 | 0.1 | N/E* |
| 71 | 0.1 | N/E* |
| 74 | 0.1 | N/E* |
| 81 | 0.1 | N/E* |
| 94 | 0.1 | 22 |
| 95 | 0.1 | N/E* |
| 96 | 0.1 | N/E* |
| 97 | 0.1 | N/E* |
| 98 | 0.1 | 20 |
| 99 | 0.1 | 2.0 |
| 100 | 0.1 | N/E* |
| 101 | 0.1 | N/E* |
| 102 | 0.1 | N/E* |
| 103 | 0.1 | 4.0 |
| 104 | 0.1 | <1 |
| 105 | 0.1 | <1 |
| 106 | 0.1 | <1 |
| 107 | 0.1 | <1 |

TABLE 7-continued

MKK4 potency and Selectivity against MKK7

| Example | Test conc. [μM] | Selectivity MKK7/MKK4 |
|---|---|---|
| 108 | 0.1 | N/E* |
| 109 | 0.1 | N/E* |
| 110 | 0.1 | N/E* |
| 111 | 0.1 | <1 |
| 112 | 0.1 | 3.8 |

N/E*: PoC for JNK1 = 100;

TABLE 8

MKK4 potency and Selectivity against BRaf

| Example | Test conc. [μM] | Selectivity BRaf/MKK4 |
|---|---|---|
| 1 | 10 | |
| 2 | 10 | |
| 3 | 0.1 | 1.0 |
| 4 | 0.1 | 2.8 |
| 5 | 0.1 | 2.9 |
| 6 | 0.1 | 0.1 |
| 7 | 0.1 | 0.9 |
| 8 | 0.1 | 0.5 |
| 9 | 0.1 | 4.2 |
| 10 | 0.1 | 4.2 |
| 11 | 0.1 | 6.3 |
| 12 | 0.1 | 7.8 |
| 13 | 0.1 | 10.5 |
| 14 | 0.1 | 1.5 |
| 15 | 0.1 | 2.0 |
| 16 | 0.1 | 2.5 |
| 17 | 0.1 | 1.2 |
| 18 | 0.1 | 1.6 |
| 19 | 0.1 | 3.4 |
| 20 | 0.1 | 4.5 |
| 21 | 0.1 | 5.8 |
| 22 | 0.1 | 5.5 |
| 23 | 0.1 | 2.4 |
| 24 | 0.1 | 0.9 |
| 25 | 0.1 | 1.0 |
| 26 | 0.1 | 1.1 |
| 27 | 0.1 | 1.9 |
| 28 | 0.1 | 0.8 |
| 29 | 0.1 | 1.8 |
| 30 | 0.1 | 2.1 |
| 31 | 0.1 | 3.1 |
| 32 | 0.1 | 1.9 |
| 33 | 0.1 | 3.3 |
| 34 | 0.1 | 34.8 |
| 35 | 0.1 | 3.3 |
| 36 | 0.1 | 18.8 |
| 37 | 0.1 | 13.2 |
| 38 | 0.1 | 5.3 |
| 39 | 0.1 | 25.9 |
| 40 | 0.1 | 4.7 |
| 41 | 0.1 | 3.3 |
| 42 | 0.1 | 0.4 |
| 43 | 0.1 | 7.7 |
| 44 | 0.1 | 14 |
| 45 | 0.1 | N/E* |
| 46 | 0.1 | N/E* |
| 47 | 0.1 | N/E* |
| 48 | 0.1 | N/E* |
| 49 | 0.1 | 8.9 |
| 50 | 0.1 | 7.0 |
| 51 | 0.1 | N/E* |
| 52 | 0.1 | N/E* |
| 53 | 0.1 | 56 |
| 54 | 0.1 | 36 |
| 55 | 0.1 | N/E* |
| 56 | 0.1 | N/E* |
| 69 | 0.1 | 6.7 |
| 70 | 0.1 | N/E* |
| 71 | 0.1 | 4.5 |
| 74 | 0.1 | 1.9 |
| 81 | 0.1 | 11 |
| 94 | 0.1 | 20 |
| 95 | 0.1 | 6.5 |
| 96 | 0.1 | 8.0 |
| 97 | 0.1 | 6.5 |
| 98 | 0.1 | 8.4 |
| 99 | 0.1 | 1.9 |
| 100 | 0.1 | 17 |
| 101 | 0.1 | 7.2 |
| 102 | 0.1 | 17 |
| 103 | 0.1 | 4.1 |
| 104 | 0.1 | 1 |
| 105 | 0.1 | N/E* |
| 106 | 0.1 | <1 |
| 107 | 0.1 | N/E* |
| 108 | 0.1 | N/E* |
| 109 | 0.1 | N/E* |
| 110 | 0.1 | N/E* |
| 111 | 0.1 | N/E* |
| 112 | 0.1 | 1.4 |

N/E*: PoC for JNK1 = 100;

Example 113-2: Functional Enzyme Assays (a) Material

Recombinant kinase proteins (commercially available)

MEKK2, recombinant, active: ProQinase product #0583-0000-1

MKK4, recombinant, activated: ProQinase product #0948-0000-1

MKK4, recombinant, non-activated: ProQinase product #0948-0000-2

Substrate proteins

Casein (Sigma C-4765)

JNK1 K55R/K56R, recombinant, inactive: ProQinase product #0524-0000-1

(b) Methods (b-1) MEKK2 dependent MKK4 activation

MKK4 (non activated) is incubated with MEKK2 (active) in a ratio of 10:1 (w/w), corresponding to a molar ratio of 20:1, in the presence of compound or vehicle and 20 μM ATP for 30 min at 30° C. The activation step is done in 50 mM HEPES pH 7.5, 50 mM NaCl, 3.8 mM $MgCl_2$, 2.5 mM DTT, 10% (v/v) glycerol. Final DMSO concentration is 1%. The activation mixture is pipetted in the following order:

2.5 μl compound in 4% DMSO 2.5 μl ATP/MgCl2 mix

5 μl premixed kinase solution MKK4:MEKK2 10:1 (w/w)

Protein concentrations in the activation mix are 1 μM MKK4 and 50 nM MEKK2.

(b-2) Protein Kinase Assay

A radiometric protein kinase assay was used for measuring the kinase activity of the respective protein kinases. All kinase assays were performed in 96-well polypropylene plates. After the reactions were stopped, the assay mixtures were transferred to 96-well MSFC filter-plates (Millipore). The reaction mix was passed through the filter membrane by aspiration, the membrane was washed 3 times with 150 mM $H_3PO_4$, once with ethanol, dried and liquid scintillation cocktail was added. Radioactivity was determined by counting of the samples in a Microbeta multiwell scintillation counter (Wallac). The reactions were pipetted in the following order:

a) MEKK2-MKK4 activation mix
20 µl standard assay buffer
10 µl MEKK2-MKK4 activation mix
5 µl radioactive $^{33}P$-γ-ATP solution (typically $10^6$ cpm/well)
10 µl of substrate solution
b) Single Kinases
20 µl standard assay buffer
5 µl compound in 10% DMSO
20 µl enzyme-substrate mix
10 µl of substrate solution The assay contained 70 mM HEPES-NaOH pH 7.5, 3 mM $MgCl_2$, 3 mM $MnCl_2$, 3 µM Na-orthovanadate, 1.2 mM DTT, ATP (variable amounts, corresponding to the apparent ATP-$K_m$ of the respective kinase, see Table 1), [$^{33}P$-γ-ATP] (approx. $8 \times 10^{05}$ cpm per well), protein kinase (variable amounts; see Table 1), and substrate (variable amounts; see Table below).

TABLE

Enzymes, substrates, and assay conditions (amounts/well)

| # | Kinase Name | Kinase Conc. ng/50 µl | Kinase Conc. nM | ATP Conc. µM | Substrate Name | µg/50 µl | nM |
|---|---|---|---|---|---|---|---|
| 1 | MKK4-MEKK2 mix | 25 | 10 | 0.2 | JNK1 KRKR | 1 | 430 |
| 2 | MKK4 active | 25 | 10 | 0.2 | JNK1 KRKR | 1 | 430 |
| 3 | MEKK2 | 150 | 30 | 0.2 | Casein | 1 | 870 |

The reaction cocktails were incubated at 30° C. for 30 minutes.

Potency of Test Compounds:

| Expl | Cascade | MKK4 | MEKK2 |
|---|---|---|---|
| 7 | + | ++ | o |
| 10 | o | o | o |
| 12 | + | ++ | o |
| 13 | + | +++ | + |
| 19 | + | +++ | + |
| 22 | o | o | o |
| 27 | o | + | o |
| 34 | + | +++ | o |
| 36 | + | o | o |
| 37 | + | ++ | o |
| 39 | + | +++ | + |
| 32 | + | +++ | o |
| 38 | + | +++ | + |
| 40 | + | +++ | + |
| 43 | + | +++ | + |
| 44 | ++ | +++ | + |
| 45 | + | + | o |
| 46 | + | +++ | + |
| 47 | + | +++ | + |
| 48 | + | + | o |
| 50 | + | +++ | o |
| 52 | + | +++ | o |
| 53 | ++ | +++ | + |
| 54 | + | +++ | + |
| 55 | ++ | +++ | o |
| 56 | +++ | +++ | o |
| 86 | + | + | o |
| 103 | +++ | +++ | +++ |
| 104 | + | + | o |
| 105 | + | + | o |
| 106 | o | + | o |
| 107 | + | +++ | + |
| 110 | ++ | ++ | o |
| 112 | + | + | o |

*potency derived from IC50-values (PoC) according to the following classification rule:

| $IC_{50} \geq$ 10 µM | $10 > IC_{50} \geq$ 1 µM | $1 > IC_{50} \geq$ 0.5 µM | $IC_{50} <$ 0.5 µM |
|---|---|---|---|
| o | + | ++ | +++ |

Example 113-3: In Vivo Study

Animals

C57BL/6N female mice, age 6-9 weeks, purchased from Charles River Laboratories, Research Models and Services, Germany GmbH (Sulzfeld), were housed in accordance with the institutional guidelines of the University of TObingen, Germany. All animal experiments were approved by the German legal authorities.

Animal Experiments and Survival Studies.

Three experiments with n=3, n=4 and n=6 animals per group were performed. At time point t=–1 h), mice were dosed by oral gavage with either 30 mg/kg of compound, mixed in 2% hydroxymethylcellulose, pH 4.0) or vehicle only. One hour later (t=0 h), all animals were intraperitoneally (i.p.) injected with 0.8 µg/g mouse weight of Jo2 antibody (BD Pharmingen, San Diego, Calif.) diluted in 0.9% NaCl.

Mice were continuously monitored and survival was monitored all 15 min. After 24 h, all surviving animals were sacrificed.

Results:

The Kaplan-Meier plot illustrates the survival rate of animals after i.p. injection of 0.8 µg/g Jo2 antibody, which received either 30 mg/kg of compound according to Example 2 or vehicle only. The survival rate of the animals upon administration of the compound of example 2 is significantly higher than that with the vehicle only. The results are shown in FIG. 1.

Example 113-4: Cellular Phenotype Assay

Hepatocyte Isolation and Cultivation

Mice were anesthetized and livers were perfused through the intrahepatic vena cava first with a Liver perfusion medium (Invitrogen, Darmstadt, Germany) for 15 min and then with collagenase (Serva) and $Ca^{2+}$-supplemented medium Williams E Medium (PAN Biotech, Aidenbach Germany) containing Collagenase 400-480 mg/L Serva Collagenase NB 4 G Proved Grades (Serva Electrophoresis GmbH, Heidelberg, Germany) for about 15 min. Livers were excised, and the liver cell suspension was centrifuged at 50 g for 5 min. The supernatant was discarded and the pellet containing parenchymal cells was collected and washed once with collagenase-free Williams' E medium (PAN Biotech). The liver parenchymal cell suspension was further centrifuged using two-step Percoll gradient (24%+50%) and 98%-pure viable hepatocytes were collected from the pellet, washed once and plated on collagen (Roche)—coated 12 well plates at a concentration of 2×10⁶ cells/well in HCM medium (Lonza; Germany) supplemented with 5% FCS, glutamine and antibiotics.

Isolated primary hepatocytes were incubated with compound supplemented medium.

Medium was refreshed all 24 h. Compounds were added to the medium in a concentration 1 uM and DMSO in equivalent volume.

Labelling with BrdU 10 ug/ml was effected overnight (5-bromo-2'-deoxyuridine Sigma B9285-250 mg)

BrdU antibody (Abcam cat no. AB6326)

Stastistical significance was evaluated with student t-test *P<0.05, P<0.005 and *P<0.0005.

Counting was done with ImageJ software 10 hpf/well (high power field).

Figure 2:
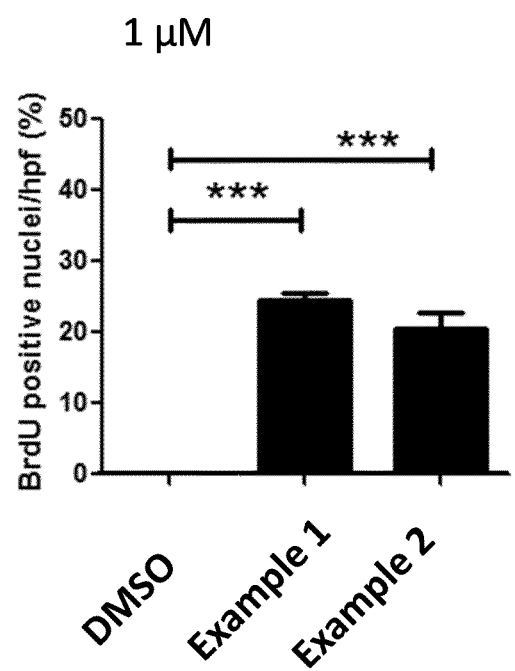
FIG. 2 is a diagram showing the percentage of BrdU-positive cells after co-incubation of compounds according to Example 1 and 2 in cultured primary mouse hepatocytes.

Results:

FIG. 2 illustrates the percentage of BrdU-positive cells after co-incubation of compounds according to Example 1 and 2 in cultured primary mouse hepatocytes.

The invention claimed is:

1. A compound which is selected from the group consisting of:
- N-(3-(5-(Benzo[d][1,3]dioxol-5-yl)-1H-pyrrolo[2,3-b]pyridine-3-carbonyl)-2,4-difluorophenyl)propane-1-sulfonamide;
- N-(2,4-Difluoro-3-(5-(4-fluoro-2-methylphenyl)-1H-pyrrolo[2,3-b]pyridine-3-carbonyl)phenyl)propane-1-sulfonamide;
- N-(3-(5-(2,3-dihydrobenzo[b][1,4]dioxin-6-yl)-1H-pyrrolo[2,3-b]pyridine-3-carbonyl)-2-fluorophenyl)methanesulfonamide;
- N-(2-fluoro-3-(5-(4-fluoro-2-methylphenyl)-1H-pyrrolo[2,3-b]pyridine-3-carbonyl)phenyl)methanesulfonamide;
- N-(3-(5-(2-chloro-4-methoxyphenyl)-1H-pyrrolo[2,3-b]pyridine-3-carbonyl)-2,4-difluorophenyl)propane-1-sulfonamide;
- N-(3-(5-(7-chloro-2,3-dihydrobenzo[b][1,4]dioxin-6-yl)-1H-pyrrolo[2,3-b]pyridine-3-carbonyl)-2,4-difluorophenyl)propane-1-sulfonamide;
- N-(2-fluoro-4-methyl-3-(5-(pyridin-3-yl)-1H-pyrrolo[2,3-b]pyridine-3-carbonyl)phenyl)propane-1-sulfonamide;
- N-(2,4-difluoro-3-(5-(4-fluoro-2-methylphenyl)-1H-pyrrolo[2,3-b]pyridine-3-carbonyl)phenyl)butane-1-sulfonamide;
- N-(3-(5-(2-chloro-4-methoxyphenyl)-1H-pyrrolo[2,3-b]pyridine-3-carbonyl)-2-fluoro-4-hydroxyphenyl)butane-1-sulfonamide;
- N-(3-(5-(4-chlorophenyl)-1H-pyrrolo[2,3-b]pyridine-3-carbonyl)-2,4-difluorophenyl) benzylsulfonamide;
- N-(3-(5-(2-chloro-4-hydroxy-phenyl)-1H-pyrrolo[2,3-b]pyridine-3-carbonyl)-2,4-difluoro-phenyl)propane-1-sulfonamide;
- N-(3-(5-(2-chloro-4-methoxyphenyl)-1H-pyrrolo[2,3-b]pyridine-3-carbonyl)-2-fluorophenyl)methane-1-sulfonamide;
- N-(3-(5-(5-chloro-benzo[d][1,3]dioxol-6-yl)-1H-pyrrolo[2,3-b]pyridine-3-carbonyl)-2-fluorophenyl)methane-1-sulfonamide;
- N-(2-fluoro-3-(5-(4-fluoro-2-methylphenyl)-1H-pyrrolo[2,3-b]pyridine-3-carbonyl)phenyl)butanesulfonamide;
- N-(2-fluoro-3-(5-(2-chloro-4-methoxyphenyl)-1H-pyrrolo[2,3-b]pyridine-3-carbonyl)phenyl)butanesulfonamide;
- N-(3-(5-(benzo[d][1,3]dioxol-5-yl)-1H-pyrrolo[2,3-b]pyridine-3-carbonyl)-2,4-difluorophenyl)propane-1-sulfonamide;
- N-(3-(5-(2,3-dihydrobenzo[d][1,3]dioxin-6-yl)-1H-pyrrolo[2,3-b]pyridine-3-carbonyl)-2-difluorophenyl)butane-1-sulfonamide;
- N-(3-(5-(5-chloro-benzo[d][1,3]dioxol-6-yl)-1H-pyrrolo[2,3-b]pyridine-3-carbonyl)-2-fluorophenyl)butane-1-sulfonamide;
- N-(3-(5-(7-chloro-2,3-dihydrobenzo[b][1,4]dioxin-6-yl)-1H-pyrrolo[2,3-b]pyridine-3-carbonyl)-2-fluorophenyl)propane-1-sulfonamide;
- N(3-(5-(2-chloro-4-(methoxymethoxy)phenyl)-1H-pyrrolo[2,3-b]pyridine-3-carbonyl)-2,4-difluorophenyl) propane-1-sulfonamide; and
- N-(2,4-difluoro-3-(5-pyridin-4-yl)-1H-pyrrolo[2,3-b]pyridine-3-carbonyl)phenyl)propane-1-sulfonamide;

and pharmaceutically acceptable salts, solvates, and optical isomers thereof.

2. The compound of claim 1, which is selected from the group consisting of:
- N-(3-(5-(2,3-dihydrobenzo[b][1,4]dioxin-6-yl)-1H-pyrrolo[2,3-b]pyridine-3-carbonyl)-2-fluorophenyl)methanesulfonamide;
- N-(2-fluoro-3-(5-(4-fluoro-2-methylphenyl)-1H-pyrrolo[2,3-b]pyridine-3-carbonyl)phenyl)methanesulfonamide;
- N-(3-(5-(2-chloro-4-methoxyphenyl)-1H-pyrrolo[2,3-b]pyridine-3-carbonyl)-2,4-difluorophenyl)propane-1-sulfonamide;
- N-(3-(5-(7-chloro-2,3-dihydrobenzo[b][1,4]dioxin-6-yl)-1-H-pyrrolo[2,3-b]pyridine-3-carbonyl)-2,4-difluorophenyl)propane-1-sulfonamide;
- N-(2-fluoro-4-methyl-3-(5-(pyridin-3-yl)-1H-pyrrolo[2,3-b]pyridine-3-carbonyl)phenyl)propane-1-sulfonamide;
- N-(2,4-difluoro-3-(5-(4-fluoro-2-methylphenyl)-1H-pyrrolo[2,3-b]pyridine-3-carbonyl)phenyl)butane-1-sulfonamide;
- N-(3-(5-(2-chloro-4-methoxyphenyl)-1H-pyrrolo[2,3-b]pyridine-3-carbonyl)-2-fluoro-4-hydroxyphenyl)butane-1-sulfonamide;
- N-(3-(5-(4-chlorophenyl)-1H-pyrrolo[2,3-b]pyridine-3-carbonyl)-2,4-difluorophenyl)benzylsulfonamide;
- N-(3-(5-(2-chloro-4-hydroxy-phenyl)-1H-pyrrolo[2,3-b]pyridine-3-carbonyl)-2,4-difluoro-phenyl)propane-1-sulfonamide;
- N-(3-(5-(2-chloro-4-methoxyphenyl)-1H-pyrrolo[2,3-b]pyridine-3-carbonyl)-2-fluorophenyl)methane-1-sulfonamide;
- N-(3-(5-(5-chloro-benzo[d][1,3]dioxol-6-yl)-1H-pyrrolo[2,3-b]pyridine-3-carbonyl)-2-fluorophenyl)methane-1-sulfonamide;
- N-(2-fluoro-3-(5-(4-fluoro-2-methylphenyl)-1H-pyrrolo[2,3-b]pyridine-3-carbonyl)phenyl)butanesulfonamide;
- N-(2-fluoro-3-(5-(2-chloro-4-methoxyphenyl)-1H-pyrrolo[2,3-b]pyridine-3-carbonyl)phenyl)butanesulfonamide;
- N-(3-(5-(benzo[d][1,3]dioxol-5-yl)-1H-pyrrolo[2,3-b]pyridine-3-carbonyl)-2,4-difluorophenyl)propane-1-sulfonamide;
- N-(3-(5-(2,3-dihydrobenzo[d][1,3]dioxin-6-yl)-1H-pyrrolo[2,3-b]pyridine-3-carbonyl)-2-difluorophenyl)butane-1-sulfonamide;

N-(3-(5-(5-chloro-benzo[d][1,3]dioxol-6-yl)-1H-pyrrolo[2,3-b]pyridine-3-carbonyl)-2-fluorophenyl)butane-1-sulfonamide;

N-(3-(5-(7-chloro-2,3-dihydrobenzo[b][1,4]dioxin-6-yl)-1H-pyrrolo[2,3-b]pyridine-3-carbonyl)-2-fluorophenyl)propane-1-sulfonamide;

N-(3-(5-(2-chloro-4-(methoxymethoxy)phenyl)-1H-pyrrolo[2,3-b]pyridine-3-carbonyl)-2,4-difluorophenyl)propane-1-sulfonamide; and N-(2,4-difluoro-3-(5-(5-pyridin-4-yl)-1H-pyrrolo[2,3-b]pyridine-3-carbonyl)phenyl)propane-1-sulfonamide;

and pharmaceutically acceptable salts, solvates, and optical isomers thereof.

3. A pharmaceutical composition comprising a therapeutically effective amount for treatment of liver in a subject in need thereof of a compound or a pharmaceutically acceptable salt[s], solvate[s], or optical isomer[s] thereof of claim 1 and a pharmaceutically acceptable carrier.

4. A pharmaceutical composition comprising a compound or a pharmaceutically acceptable salt[s], solvate[s], or optical isomer[s] thereof of claim 1 and a pharmaceutically acceptable carrier.

5. A method of treatment of liver in a subject in need thereof, wherein the treatment is selected from the group consisting of selectively inhibiting protein kinase MKK4 over protein kinases JNK1 and MKK7, promoting liver regeneration, preventing hepatocyte death, treating acute liver disease, treating chronic liver disease, and treating acute on chronic liver disease, which comprises administering to the subject in need thereof a therapeutically effective amount of a compound or a pharmaceutically acceptable salt, solvate, or optical isomer thereof of claim 1.

6. The method of claim 5, wherein the acute liver disease, chronic liver disease, or acute on chronic liver disease is selected from the group consisting of acute and chronic viral hepatitis, autoimmune hepatitis, primary sclerosing hepatitis, alcoholic hepatitis, metabolic liver diseases, liver cirrhosis, acute (fulminant)liver failure, chronic toxic liver failure, acute toxic liver failure, liver disease due to vascular diseases, acute liver failure of unknown origin, chronic liver disease due to right heart failure, galactosemia, cystic fibrosis, *porphyria*, hepatic ischemia perfusion injury, small for size syndrome after liver transplantation, primary sclerosing cholangitis and hepatic encephalopathy.

7. The method of claim 5, wherein the acute liver disease, chronic liver disease, or acute on chronic liver disease is selected from the group consisting of hepatitis B, hepatitis C, hepatitis E, hepatitis caused by Epstein-Barr virus, hepatitis caused by cytomegalovirus, hepatitis caused by herpes simplex virus, metabolic syndrome, fatty liver like non-alcoholic fatty liver (NAFL), non-alcoholic steatohepatitis (NASH), alcoholic steatohepatitis (ASH), Morbus Wilson, hemochromatosis, alpha-antitrypsin deficiency, glycogen storage diseases, primary biliary cirrhosis, ethyl toxic liver cirrhosis, cryptogenic cirrhosis; acetaminophen (paracetamol)-induced liver failure, alpha-amanitin-induced liver failure, hepatotoxicity/liver failure induced by antibiotics, hepatotoxicity/liver failure induced by nonsteroidal anti-inflammatory drugs, hepatotoxicity/liver failure induced by anticonvulsants, acute liver failure induced by kava, acute liver failure induced by ephedra, acute liver failure induced by skullcap, acute liver failure induced by pennyroyal, and liver disease caused by Budd-Chiari syndrome.

8. A packaged pharmaceutical comprising the pharmaceutical composition of claim 3 and instructions for use.

9. A packaged pharmaceutical comprising the pharmaceutical composition of claim 4 and instructions for use.

10. The method of treatment of liver in the subject in need thereof of claim 5, wherein the treatment is selectively inhibiting protein kinase MKK4 over protein kinases JNK1 and MKK7.

11. The method of treatment of liver in the subject in need thereof of claim 5, wherein the treatment is selected from the group consisting of promoting liver regeneration and preventing hepatocyte death.

12. The method of treatment of liver in the subject in need thereof of claim 5, wherein the treatment is selected from the group consisting of treating acute liver disease, treating chronic liver disease, and treating acute on chronic liver disease.

13. The method of treatment of liver in the subject in need thereof of claim 12, wherein the acute liver disease, chronic liver disease, or acute on chronic liver disease is selected from the group consisting of acute and chronic viral hepatitis, autoimmune hepatitis, primary sclerosing hepatitis, alcoholic hepatitis, metabolic liver diseases, liver cirrhosis, acute (fulminant)liver failure, chronic toxic liver failure, acute toxic liver failure, liver disease due to vascular diseases, acute liver failure of unknown origin, chronic liver disease due to right heart failure, galactosemia, cystic fibrosis, porphyria, hepatic ischemia perfusion injury, small for size syndrome after liver transplantation, primary sclerosing cholangitis and hepatic encephalopathy.

14. The method of treatment of liver in the subject in need thereof of claim 12, wherein the acute liver disease, chronic liver disease, or acute on chronic liver disease is selected from the group consisting of hepatitis B, hepatitis C, hepatitis E, hepatitis caused by Epstein-Barr virus, hepatitis caused by cytomegalovirus, hepatitis caused by herpes simplex virus, metabolic syndrome, fatty liver like non-alcoholic fatty liver (NAFL), non-alcoholic steatohepatitis (NASH), alcoholic steatohepatitis (ASH), Morbus Wilson, hemochromatosis, alpha1-antitrypsin deficiency, glycogen storage diseases, primary biliary cirrhosis, ethyl toxic liver cirrhosis, cryptogenic cirrhosis; acetaminophen (paracetamol)-induced liver failure, alpha-amanitin-induced liver failure, hepatotoxicity/liver failure induced by antibiotics, hepatotoxicity/liver failure induced by nonsteroidal anti-inflammatory drugs, hepatotoxicity/liver failure induced by anticonvulsants, acute liver failure induced by kava, acute liver failure induced by ephedra, acute liver failure induced by skullcap, acute liver failure induced by pennyroyal, and liver disease caused by Budd-Chiari syndrome.

15. The method of treatment of liver in the subject in need thereof of claim 5, wherein the compound or a pharmaceutically acceptable salt, solvate or optical isomer thereof is administered at a dosage or 0.2 to 15 mg/kg of the subject over 1 to 12 weeks.

* * * * *